United States Patent
Hill

(10) Patent No.: US 7,095,508 B2
(45) Date of Patent: Aug. 22, 2006

(54) CATOPTRIC AND CATADIOPTRIC IMAGING SYSTEMS WITH PELLICLE AND APERTURE-ARRAY BEAM-SPLITTERS AND NON-ADAPTIVE AND ADAPTIVE CATOPTRIC SURFACES

(76) Inventor: Henry A. Hill, 340 S. Avenida de Palmas, Tucson, AZ (US) 85716

( * ) Notice: Subject to any disclaimer, the term of this patent is extended or adjusted under 35 U.S.C. 154(b) by 0 days.

(21) Appl. No.: 11/231,485

(22) Filed: Sep. 21, 2005

(65) Prior Publication Data

US 2006/0092429 A1    May 4, 2006

Related U.S. Application Data

(63) Continuation of application No. 10/948,959, filed on Sep. 24, 2004.

(60) Provisional application No. 60/506,715, filed on Sep. 26, 2003.

(51) Int. Cl.
*G01B 9/02* (2006.01)
(52) U.S. Cl. .................................... 356/512
(58) Field of Classification Search ................ 356/450, 356/511, 512, 513, 514, 521; 359/570, 571
See application file for complete search history.

(56) References Cited

U.S. PATENT DOCUMENTS

| | | |
|---|---|---|
| 3,628,027 A | 12/1971 | Brauss |
| 3,748,015 A | 7/1973 | Offner |
| 4,011,011 A | 3/1977 | Hemstreet et al. |
| 4,226,501 A | 10/1980 | Shafer |
| 4,272,684 A | 6/1981 | Seachman |
| 4,408,884 A | 10/1983 | Kleinknecht et al. |
| 4,672,196 A | 6/1987 | Canino |
| 4,685,803 A | 8/1987 | Sommargren |
| 4,733,967 A | 3/1988 | Sommargren |
| 5,220,403 A | 6/1993 | Batchelder et al. |
| 5,241,423 A | 8/1993 | Chiu et al. |
| 5,327,223 A | 7/1994 | Korth |
| 5,384,639 A | 1/1995 | Wickramasinghe |
| 5,392,118 A | 2/1995 | Wickramasinghe |
| 5,485,317 A | 1/1996 | Perissinotto |
| 5,602,643 A | 2/1997 | Barrett |
| 5,614,763 A | 3/1997 | Womack |
| 5,633,972 A | 5/1997 | Walt |
| 5,659,420 A | 8/1997 | Wakai |
| 5,699,201 A | 12/1997 | Lee |
| 5,757,493 A | 5/1998 | Vaknerkhove |
| 5,760,901 A | 6/1998 | Hill |
| 5,828,455 A | 10/1998 | Smith |

(Continued)

OTHER PUBLICATIONS

U.S. Appl. No. 60/442,858, filed Jan. 27, 2003, Hill.

(Continued)

*Primary Examiner*—Hwa (Andrew) Lee
*Assistant Examiner*—Michael A. Lyons

(57) ABSTRACT

An interferometric system including: an interferometer that directs a measurement beam at an object point to produce a return measurement beam, focuses the return measurement beam to an image point in an image plane, and mixes the return measurement beam with a reference beam at the image point to form a mixed beam; a beam combining layer located at the image plane which is responsive to the mixed beam and produces an optical beam therefrom, wherein the layer comprises a thin film with an array of transmissive openings formed therein and further comprises a fluorescent material associated with each of the openings of the array of openings; a detector that is responsive to the optical beam from the beam combining layer; and an imaging system that directs the optical beam from the beam combining layer onto the detector.

20 Claims, 35 Drawing Sheets

U.S. PATENT DOCUMENTS

| | | | |
|---|---|---|---|
| 5,894,195 | A | 4/1999 | McDermott |
| 5,915,048 | A | 6/1999 | Hill et al. |
| 5,923,423 | A | 7/1999 | Sawatari et al. |
| 6,011,654 | A | 1/2000 | Schweizer Juergen et al. |
| 6,480,285 | B1 | 3/2000 | Hill |
| 6,052,231 | A | 4/2000 | Rosenbluth |
| 6,091,496 | A | 7/2000 | Hill |
| 6,445,453 | B1 | 8/2000 | Hill |
| 6,606,159 | B1 | 8/2000 | Hill |
| 6,124,931 | A | 9/2000 | Hill |
| 6,552,805 | B1 | 7/2001 | Hill |
| 6,667,809 | B1 | 7/2001 | Hill |
| 6,775,009 | B1 | 7/2001 | Hill |
| 6,847,029 | B1 | 7/2001 | Hill |
| 6,271,923 | B1 | 8/2001 | Hill |
| 6,330,065 | B1 | 12/2001 | Hill |
| 6,552,852 | B1 | 12/2001 | Hill |
| 6,018,391 | A1 | 1/2002 | Yoshida |
| 6,714,349 | B1 | 3/2002 | Nam |
| 6,447,122 | B1 | 9/2002 | Kobayashi et al. |
| 6,469,788 | B1 | 10/2002 | Boyd et al. |
| 6,753,968 | B1 | 1/2003 | Hill |
| 6,847,452 | B1 | 3/2003 | Hill |
| 6,597,721 | B1 | 7/2003 | Hutchinson et al. |
| 6,707,561 | B1 | 3/2004 | Budach et al. |
| 6,717,736 | B1 | 4/2004 | Hill |
| 6,771,374 | B1 | 8/2004 | Rangarajan et al. |
| 6,806,959 | B1 | 10/2004 | Tukker |
| 2002/0074493 | A1 | 6/2002 | Hill |
| 2002/0131179 | A1 | 9/2002 | Hill |
| 2003/0174992 | A1 | 9/2003 | Levene |
| 2004/0201852 | A1 | 10/2004 | Hill |
| 2004/0201853 | A1 | 10/2004 | Hill |
| 2004/0201854 | A1 | 10/2004 | Hill |
| 2004/0201855 | A1 | 10/2004 | Hill |
| 2004/0202426 | A1 | 10/2004 | Hill |
| 2004/0227950 | A1 | 11/2004 | Hill |
| 2004/0227951 | A1 | 11/2004 | Hill |
| 2004/0228008 | A1 | 11/2004 | Hill |
| 2004/0246486 | A1 | 12/2004 | Hill |
| 2004/0257577 | A1 | 12/2004 | Hill |
| 2005/0036149 | A1 | 2/2005 | Hill |
| 2005/0111006 | A1 | 5/2005 | Hill |
| 2005/0111007 | A1 | 5/2005 | Hill |

OTHER PUBLICATIONS

U.S. Appl. No. 60/442,982, filed Jan. 29, 2003, Hill.
U.S. Appl. No. 60/443,980, filed Jan. 31, 2003, Hill.
U.S. Appl. No. 60/444,707, filed Feb. 4, 2003, Hill.
U.S. Appl. No. 60/445,739, filed Feb. 7, 2003, Hill.
U.S. Appl. No. 60/447,254, filed Feb. 13, 2003, Hill.
U.S. Appl. No. 60/448,360, filed Feb. 19, 2003, Hill.
U.S. Appl. No. 60/448,250, filed Feb. 19, 2003, Hill.
U.S. Appl. No. 60/459,493, filed Apr. 1, 2003, Hill.
U.S. Appl. No. 60/460,129, filed Apr. 3, 2003, Hill.
U.S. Appl. No. 60/459,425, filed Apr. 11, 2003, Hill.
U.S. Appl. No. 60/485,255, filed Jul. 7, 2003, Hill.
U.S. Appl. No. 60/485,507, filed Jul. 7, 2003, Hill.
U.S. Appl. No. 60/501,666, filed Sep. 10, 2003, Hill.
U.S. Appl. No. 60/506,715, filed Sep. 26, 2003, Hill.
U.S. Appl. No. 60/507,675, filed Oct. 1, 2003, Hill.
U.S. Appl. No. 60/568,774, filed May 6, 2004, Hill.
U.S. Appl. No. 60/569,807, filed May 11, 2004, Hill.
U.S. Appl. No. 60/571,967, filed May 18, 2004, Hill.
U.S. Appl. No. 60/573,196, filed May 21, 2004, Hill.

CATOPTRIC AND CATADIOPTRIC IMAGING SYSTEMS WITH PELLICLE AND APERTURE-ARRAY BEAM-SPLITTERS AND NON-ADAPTIVE AND ADAPTIVE CATOPTRIC SURFACES

This application is a continuation of application Ser. No. 10/948,959, filed Sep. 24, 2004. This application also claims the benefit of U.S. Provisional Application No. 60/506,715, filed Sep. 26, 2003.

BACKGROUND OF THE INVENTION

A number of different applications of catadioptric imaging systems for far-field and near-field interferometric confocal and non-confocal microscopy have been described such as in commonly owned U.S. Pat. No. 6,552,852 entitled "Catoptric And Catadioptric Imaging Systems" and U.S. Pat. No. 6,717,736 entitled "Catoptric And Catadioptric Imaging Systems;" U.S. Provisional Patent Applications No. 60/447,254, filed Feb. 13, 2003, entitled "Transverse Differential Interferometric Confocal Microscopy,"; No. 60/448,360, filed Feb. 19, 2003, entitled "Longitudinal Differential Interferometric Confocal Microscopy for Surface Profiling,"; No. 60/448,250, filed Feb. 19, 2003, entitled "Method and Apparatus for Dark Field Interferometric Confocal Microscopy,"; No. 60/442,982, filed Jan. 28, 2003, entitled "Interferometric Confocal Microscopy Incorporating Pinhole Array Beam-Splitter,"; No. 60/459,425, filed Apr. 1, 2003, entitled "Apparatus and Method for Joint Measurement Of Fields Of Scattered/Reflected Orthogonally Polarized Beams By An Object In Interferometry,"; No. 60/485,507, filed Jul. 7, 2003, entitled "Apparatus And Method For High Speed Scan For Sub-Wavelength Defects And Artifacts In Semiconductor Metrology,"; No. 60/485,255, filed Jul. 7, 2003, entitled "Apparatus and Method for Ellipsometric Measurements with High Spatial Resolution,"; No. 60/501,666, filed Sep. 10, 2003, entitled "Catoptric And Catadioptric Imaging Systems With Adaptive Catoptric Surfaces,"; No. 60/602,046, filed Aug. 16, 2004, entitled "Apparatus And Method For Joint And Time Delayed Measurements Of Components Of Conjugated Quadratures Of Fields Of Reflected/Scattered Beams By An Object In Interferometry,"; and U.S. patent applications Ser. No. 10/778,371, filed Feb. 13, 2004, entitled "Transverse Differential Interferometric Confocal Microscopy,"; Ser. No. 10/782,057, filed Feb. 19, 2004, entitled "Longitudinal Differential Interferometric Confocal Microscopy for Surface Profiling,"; Ser. No. 10/782,058, filed Feb. 19, 2004, entitled "Method and Apparatus for Dark Field Interferometric Confocal Microscopy,"; Ser. No. 10/765,229, filed Jan. 27, 2004, entitled "Interferometric Confocal Microscopy Incorporating Pinhole Array Beam-Splitter,"; Ser. No. 10/816,180, filed Apr. 1, 2004, entitled "Apparatus and Method for Joint Measurement Of Fields Of Scattered/Reflected or Transmitted Orthogonally Polarized Beams By An Object In Interferometry,"; Ser. No. 10/886,010, filed Jul. 7, 2004, entitled "Apparatus And Method For High Speed Scan For Sub-Wavelength Defects And Artifacts In Semiconductor Metrology,"; Ser. No. 10/886,157, filed Jul. 7, 2004, entitled "Apparatus and Method for Ellipsometric Measurements with High Spatial Resolution,"; and Ser. No. 10/218,408, filed Sep. 10, 2004, entitled "Catoptric And Catadioptric Imaging Systems With Adaptive Catoptric Surfaces,". In addition, U.S. patent application Ser. No. 10/218,201, entitled "Method for Constructing a Catadioptric Lens System," filed Apr. 1, 2004 described one way to make some of these catadioptric lens systems. These patents, patent applications, and provisional patent applications are all by Henry A. Hill and the contents of each are incorporated herein in their entirety by reference.

In each of the applications of catadioptric imaging systems for each of the cited U.S. patents, U.S. patent applications, and U.S. Provisional Patent Applications, a beam-splitter is incorporated in generating an image of an object with zero optical aberrations for a measurement object located on the optic axis of the imaging system. The beam-splitter is located at an interface between relatively thick optical elements of the catadioptric imaging systems. The optical elements contribute off-axis aberrations and cause a significant portion of optical paths in the catadioptric imaging systems to comprise a transmitting refractive medium such as fused silica or $CaF_2$.

In each of the applications of catadioptric imaging systems for each of the cited U.S. patents, U.S. patent applications, and U.S. Provisional Patent Applications, tight tolerances are generally placed on the manufacture of optical elements. In addition to the tolerances normally encountered in designing a diffraction limited imaging system, there are additional tolerances imposed in interferometric confocal and non-confocal microscopy applications. The additional tolerances are for example on surfaces of certain elements with respect to radii of curvature and on relative locations of centers of curvature of the surfaces of the certain elements.

The additional tolerances lead to improved performance of a catoptric or a catadioptric imaging system, e.g., with respect to increasing the average intensity of desired images by a factor of approximately 2 and reduced intensity of spurious beams by one or more order of magnitudes, and in addition make it possible to realize interferometric reduction of background fields. The interferometric reduction of background fields leads to a reduction of statistical errors. The increase in intensity of desired images and the reduction of statistical errors lead to an increase in signal-to-noise ratios and to a concomitant increase in throughput of a metrology tool using the catoptric or catadioptric imaging system. The interferometric reduction of background fields further leads to a reduction of systematic errors. A consequence of the reduction of systematic errors is a reduction of the computational task required to invert arrays of measured interference signal values to a multi-dimensional image of a measurement object.

The cited U.S. patents, U.S. patent applications, and U.S. Provisional Patent Applications further teach the use of adaptive catoptric surfaces in a catoptric or catadioptric imaging system. The use of adaptive catoptric surfaces in a catoptric or catadioptric imaging system makes it possible to relax tolerances on the surface figures of elements, to relax tolerances on locations of surfaces of the elements in the catoptric or catadioptric imaging system, and to compensate for certain optical aberrations such as may be introduced by the pellicle or aperture-array beam-splitter. The factor by which the tolerances may be relaxed on the surface figures is of the order of 5 for certain of the elements. The use of adaptive catoptric surfaces in a catoptric or catadioptric imaging system further makes it possible to introduce a vertical or lateral scan of a measurement object or substrate being imaged at slew rates higher than possible and/or practical when the vertical or lateral scan must otherwise be introduced either by translations of an entire catoptric or catadioptric imaging system and associated optics and detector systems or translations of the measurement object or substrate, e.g., a 300 mm wafer, and the measurement object or substrate support system.

The cited U.S. patents, U.S. patent applications, and U.S. Provisional Patent Applications further teach the replacement of a beam combining beam-splitter in an interferometric imaging system with a thin fluorescent layer or interface.

The cited U.S. patents, U.S. patent applications, and U.S. Provisional Patent Applications also teach the use of an N-dimensional bi- and quad-homodyne detection methods.

SUMMARY OF THE INVENTION

Taught herein is the use of a thin beam-splitter in a catoptric or catadioptric imaging system to generate an image of a measurement object with zero or substantially zero optical aberrations for an object located on the optic axis of the imaging system. The use of the thin beam-splitter reduces the magnitude of off-axis aberrations that may or may not be compensated, increases the field of view that may be used, and reduces the optical path length in a transmitting refractive medium which is particularly important when working in the IR, VUV, or EUV.

As taught herein, the use of multi-element adaptive catoptric surfaces in catoptric and catadioptric imaging systems also makes it possible to compensate for optical aberrations such as may be introduced by a pellicle or aperture-array beam-array beam-splitter or such as introduced when imaging a plane section of a substrate wherein one or more plane refracting surfaces are located for example in the object space of the catoptric or catadioptric imaging system near and in front of the plane section of the substrate. The compensation of the optical aberrations corresponds to the conversion of one or more spherical catoptric surfaces to one or more aspherical catoptric surfaces.

As is also taught herein, the replacement of a beam combining beam-splitter in interferometric imaging system with a beam combining thin fluorescent layer or interface or with the array of thin fluorescent spots of the present invention impacts on the performance specifications required of optical elements of the interferometric imaging system and/or detector that follow the beam combining function to achieve a certain end use performance. The thin fluorescent layer, e.g., lumogen, absorbs light at one wavelength, e.g., the UV, VUV, or EUV, and emits light at a longer wave length, e.g., in the visible, to generate an optical interference signal. The optical interference signal is subsequently converted to an electrical interference signal when the longer wavelength light is detected by a detector. Thus there is a concomitant reduction in the required performance specifications of the optical elements because the optical elements serve only to transmit beams and generate optical images at the longer wavelength instead of at the shorter wavelength beam in the UV, VUV, or EUV. The shorter wavelength beam that is absorbed is a mixed beam which comprises a measurement beam component and a reference beam component in the same polarization state.

In the case where a beam-splitter is used for the beam combining function, the measurement beam component and the reference beam component of the combined beam may have subsequent to the beam-splitter different paths in the optical elements which introduces the possibility of non-common path phase errors. The possibility of non-common path phase errors is not present when a thin fluorescent layer serves the beam combining function.

When the shorter wavelength beam has a wavelength in the UV, VUV, or EUV and a thin fluorescent layer serves the beam combining function, there is a significant change in the required performance of the detector because it has to serve to only detect the longer wavelength optical beam instead of the shorter wavelength mixed beam. The advantage of the present invention with respect to the reduction on the required performance specifications of the optical elements and the detector is valid for measurement and reference beams comprising either UV, VUV, or EUV wavelengths.

The implementation of the N-dimensional bi- and quad-homodyne detection methods make it possible to extend the advantages of the bi- and quad-homodyne detection methods for measuring conjugated quadratures of fields jointly to homodyne methods for measuring conjugated quadratures of fields when measuring jointly N different properties of the fields.

In general, in one aspect, the invention features an interferometric system including: an interferometer that directs a measurement beam at an object point to produce a return measurement beam, focuses the return measurement beam to an image point in an image plane, and mixes the return measurement beam with a reference beam at the image point to form a mixed beam; a beam combining layer located at the image plane which is responsive to the mixed beam and produces an optical beam therefrom, wherein the layer includes a thin film with an array of transmissive openings formed therein and further includes a fluorescent material associated with each of the openings of the array of openings; a detector that is responsive to the optical beam from the beam combining layer; and an imaging system that directs the optical beam from the beam combining layer onto the detector.

Other embodiments include one or more of the following features. The beam combining layer includes a first layer in which the array of openings is formed and a second layer behind the first layer and includes the fluorescent material. The beam combining layer further includes a third layer including an array of microlenses, each of which is aligned with a different one of the openings in the array of openings. Alternatively, the fluorescent material is in each of the openings of the array of openings. Each of the openings in the array of openings is conically shaped. The fluorescent material is lumogen. The fluorescent material is sensitive to UV or VUV. The fluorescent material is responsive to radiation at a first wavelength and the detector is responsive to light at a second wavelength, wherein the first and second wavelengths are different. The fluorescent material is responsive to radiation in the UV or VUV region and the detector is responsive to light in the visible region. The fluorescent material absorbs radiation at a first wavelength and emits radiation at a second wavelength, wherein the second wavelength is longer than the first wavelength. The imaging system is a low power microscope. The interferometer includes a catadioptric imaging system. The interferometer includes: a beam splitter positioned to receive the return measurement beam from the object point and separate each of a plurality of rays into a transmitted portion and a reflected portion, the transmitted portions defining a first set of rays and the reflected portions defining a second set of rays; and a reflecting surface positioned to receive one of the sets of rays from the beam splitter and focus that set of rays towards the image point via the beam splitter. The beam splitter has an array of transmitting apertures formed therein and wherein the one set of rays travels along a path contacting on one end the beam splitter and on another end the concave reflecting surface and at least most of which passes through a gas or vacuum. The interferometer includes an array of independently positionable reflecting elements forming the reflecting surface. The reflecting surface is positioned to receive the first set of rays and reflect the first set of rays back to the beam splitter, and wherein the beam splitter is positioned to reflect at least a portion of each ray received from the reflecting surface to the image point.

In general, in another aspect, the invention features an imaging system for imaging an object point to an image point, the system including: a beam splitter positioned to receive light rays from the object point and separate each of a plurality of rays into a transmitted portion and a reflected portion, the transmitted portions defining a first set of rays and the reflected portions defining a second set of rays; and an optical structure forming a concave reflecting surface positioned to receive one of the sets of rays from the beam splitter and focus that set of rays towards the image point via the beam splitter, wherein the beam splitter has an array of transmitting apertures formed therein and wherein the one set of rays travels along a path contacting on one end the beam splitter and on another end the concave reflecting surface and at least most of which passes through a gas or vacuum.

Other embodiments include one or more of the following features. The beam splitter is a self-supporting structure. The beam splitter includes a thin reflective layer in which the array of transmitting apertures are formed. The thin reflective layer is highly reflective. The thin reflective layer is made of aluminum. The beam splitter includes a pellicle on which the thin reflective layer is formed. The beam splitter includes a first pellicle and a second pellicle with the thin reflective layer sandwiched between the first and second pellicles. The pellicle is made of a refractive material, e.g. UV grade fused silica, F—$SiO_2$, $CaF_2$, or LiF. The beam splitter is a vertically oriented, planar structure. The size of the apertures is larger than the wavelength of the light rays being imaged onto the image point. The beam splitter includes a grid of conducting wires which defines the array of transmitting apertures. The reflecting surface is positioned to receive the first set of rays and reflect the first set of rays back to the beam splitter, and wherein the beam splitter is positioned to reflect at least a portion of each ray received from the reflecting surface to the image point. The reflecting surface is substantially concentric with the object point. Alternatively, the reflecting surface is positioned to receive the second set of rays and reflect the second set of rays back to the beam splitter, wherein the beam splitter is positioned to transmit at least a portion of each ray received from the reflecting surface to the image point. In that case, the reflecting surface is substantially concentric with the image point. The optical structure includes an array of independently positionable reflecting elements forming the reflecting surface.

In general, in yet another aspect, the invention features an imaging system for imaging an object point to an image point. The system includes: a beam splitter positioned to receive light rays from the object point and separate each of a plurality of rays into a transmitted portion and a reflected portion, the transmitted portions defining a first set of rays and the reflected portions defining a second set of rays; and an array of independently positionable reflecting elements arranged to form a Fresnel reflecting surface that is positioned to receive one of the sets of rays from the beam splitter and focus that set of rays towards the image point via the beam splitter.

Other embodiments include one or more of the following features. The array of independently positionable reflecting elements form corresponding portions of the Fresnel reflecting surface and wherein the corresponding portions of the reflecting surface have a common center of curvature and different radii of curvature. The imaging system also includes a plurality of position control elements, each of which is connected to a corresponding one of the reflecting elements in the array. Each of the position control elements of the plurality of position control elements includes a transducer. Each transducer of the plurality of transducers controls a radial position of its corresponding reflecting element. Each transducer of the plurality of transducers controls an orientation of the corresponding reflecting element relative to an optical axis for that reflecting element. The imaging system also includes a servo control system which controls the plurality of transducers. The reflecting surface is positioned to receive the first set of rays and reflect the first set of rays back to the beam splitter, and wherein the beam splitter is positioned to reflect at least a portion of each ray received from the reflecting surface to the image point. Alternatively, the reflecting surface is positioned to receive the second set of rays and reflect the second set of rays back to the beam splitter, wherein the beam splitter is positioned to transmit at least a portion of each ray received from the reflecting surface to the image point.

In general, in still yet another aspect, the invention features an interferometric system including: an interferometer that directs a measurement beam at an object point to produce a return measurement beam, focuses the return measurement beam to an image point in an image plane, and mixes the return measurement beam with a reference beam at the image point to form a mixed beam; and a detector system that generates an electrical interference signal from the mixed beam, wherein the interferometer includes a source for generating an input beam and an apodizing filter through which the input beams passes to generate a conditioned beam, and wherein the measurement beam is derived from the conditioned beam.

Other embodiments include one or more of the following features. The interferometer further includes a focusing optic for focusing the measurement beam as a spot on the object. The apodizing filter includes an aperture that is apodized. The apodizing filter includes an aperture and a coating that has a transmission coefficient that depends on the position within the aperture.

In general, in still yet another aspect, the invention features an imaging system for imaging an object point to an image point. The imaging system includes: a beam splitter positioned to receive light rays from the object point and separate each of a plurality of rays into a transmitted portion and a reflected portion, the transmitted portions defining a first set of rays and the reflected portions defining a second set of rays; and an optical structure forming a concave reflecting surface positioned to receive one of the sets of rays from the beam splitter and focus that set of rays towards the image point via the beam splitter, wherein the beam splitter has an array of transmitting apertures formed therein and wherein the one set of rays travels along a path contacting on one end the beam splitter and on another end the concave reflecting surface and at least most of which passes through a gas or vacuum.

Other embodiments include one or more of the following features. The density of apertures is such that the beam splitter is characterized by net reflection and transmission coefficients that are nominally equal at each location within a working area of the beam splitter. The beam splitter has a central axis and wherein each aperture in the array of transmitting apertures has a dimension in a radial direction relative the central axis that is an increasing function of that apertures distance from the central axis. In addition, each aperture in the array of transmitting apertures has a dimension in an azimuthal direction relative the central axis that is an increasing function of that apertures distance from the central axis.

An advantage of at least one embodiment of the present invention is the reduction of the magnitude of optical aberrations introduced by different elements of a catoptric or catadioptric imaging system.

Another advantage of at least one embodiment of the present invention is a reduction of optical path length for reference and/or measurement beams in a refractive medium in a catoptric or catadioptric imaging system.

Another advantage of at least one embodiment of the present invention is the extension of the range of wavelengths that may be used in a catoptric or catadioptric imaging system.

Another advantage of at least one embodiment of the present invention is that a catoptric or catadioptric imaging system may be employed in interferometric or non-interferometric imaging systems.

Another advantage of at least one embodiment of the present invention is that a catoptric or catadioptric imaging system may be employed in an interferometric or non-interferometric imaging system operating in a reflecting mode to measure properties of fields reflected/scattered by a substrate.

Another advantage of at least one embodiment of the present invention is that a catoptric or catadioptric imaging system may be employed in an interferometric or non-interferometric imaging system operating in a transmitting mode to measure properties of fields transmitted/scattered by a substrate.

Another advantage of at least one embodiment of the present invention is that multiple catoptric and/or catadioptric imaging systems may be employed simultaneously to image an object to achieve a large numerical aperture of ≈0.9 or larger with no central obstruction of fields scattered/reflected or transmitted/scattered by the object.

Another advantage of at least one embodiment of the present invention is that use of multi-element adaptive catoptric surfaces makes it possible to introduce a mode of operation such that the image of a plane section of an object is fixed in an image plane for a short period of time that covers the duration of a beam pulse generating the image although the plane section of the object is moving in the object space at either a low or high slew rate.

Another advantage of the present invention is that a catoptric or catadioptric imaging system may be used with a large working distance.

Another advantage of at least one embodiment of the present invention is the generation of diffraction limited images of plane sections embedded in a substrate.

Another advantage of at least one embodiment of the present invention is high speed vertical scans with diffraction limited imaging of plane sections embedded in a substrate.

Another advantage of at least one embodiment of the present invention is high speed lateral scans with diffraction limited imaging of a plane section embedded in a substrate.

Another advantage of at least one embodiment of the present invention is a high speed approach to and acquisition of a substrate surface.

Another advantage of at least one embodiment of the present invention is lateral differential interferometric measurements of a plane section embedded in a substrate.

Another advantage of at least one embodiment of the present invention is differential measurements of spatial Fourier components of a plane section embedded in a substrate.

Another advantage of at least one embodiment of the present invention is high speed lateral differential interferometric scans of an embedded plane section of a substrate.

Another advantage of at least one embodiment of the present invention is the use of high speed N-dimensional bi- and quad-homodyne detection methods.

Another advantage of the present invention is a phase modulating mode of operation.

Another advantage of at least one embodiment of the present invention is an optical switching mode of operation.

Another advantage of at least one embodiment of the present invention is the option to rapidly switch between far-field and evanescent-field interferometric confocal microscopy imaging of a substrate.

Another advantage of at least one embodiment of the present invention is the option to use an array of thin fluorescent spots as a beam combining beam-splitter in an interferometer system to increase the resolution of the imaging system used in the interferometer system and/or to reduce the magnitude of the contribution of background to a measured electrical interference signal.

DETAILED DESCRIPTION

Figure 1A:
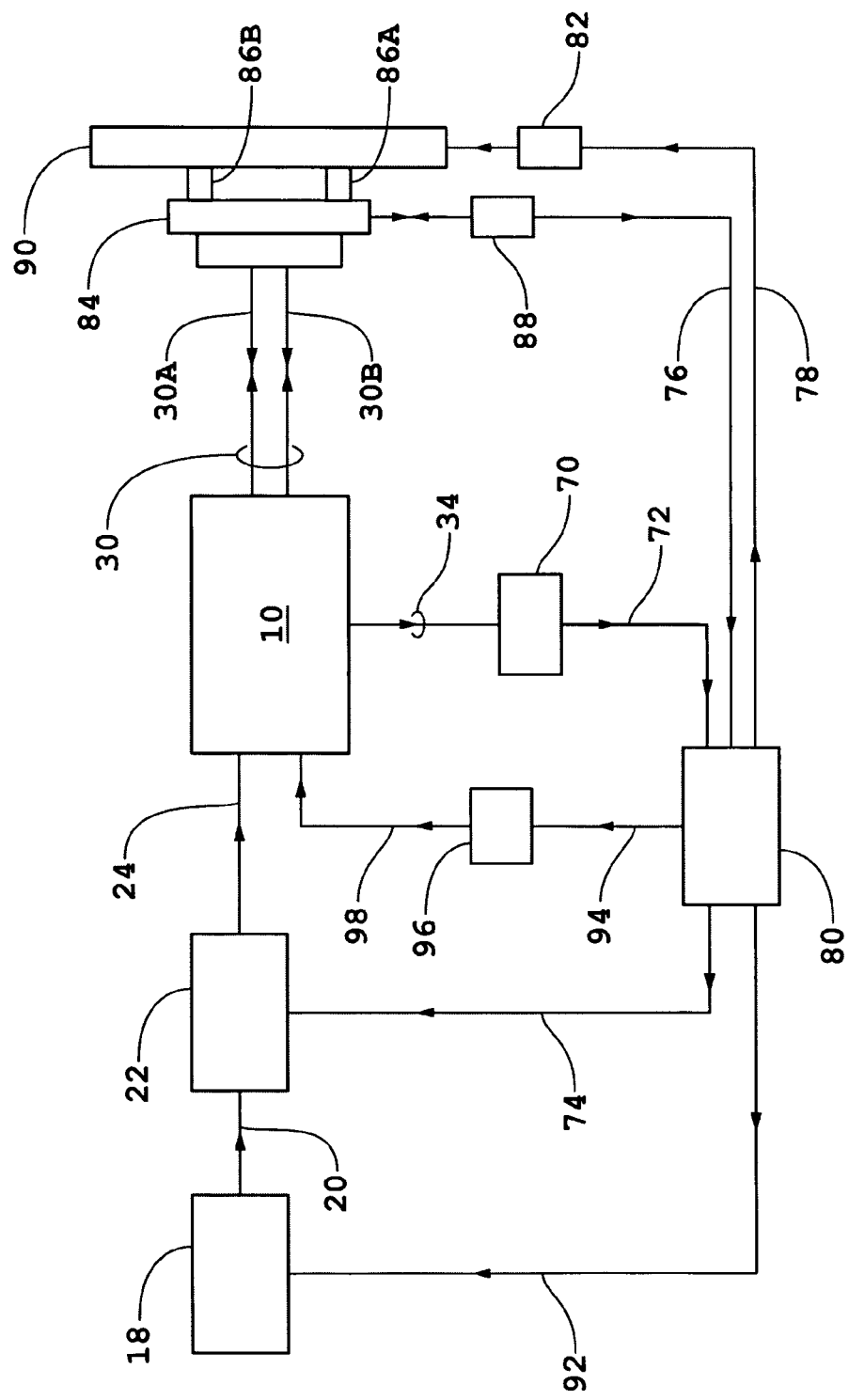
FIG. 1a is a schematic diagram of an interferometric system operating in a reflecting mode.

To be described herein is a catoptric or a catadioptric imaging system incorporates a thin beam-splitter, thin with respect to generation of optical aberrations and/or internal absorption, or an aperture-array beam-splitter in generating an image of a measurement object with zero or substantially zero optical aberrations for an object located on the optic axis of the imaging system configured with a large numerical aperture. The catoptric surfaces of the catoptric or catadioptric imaging system may comprise spherical surfaces. In addition, the catoptric surfaces of the catoptric or catadioptric imaging system may comprise convex surfaces of a medium having an index of refraction greater than one, or alternatively, one or more catoptric surfaces of a catoptric or catadioptric imaging system may comprise adaptive catoptric surfaces wherein each of the one or more adaptive catoptric surfaces are generated by an array of reflecting elements. The thin beam-splitter may be a pellicle beam-splitter comprising a stack of one or more thin layers of dielectrics and conductors, e.g., aluminum, and the aperture-array beam-splitter may comprise a thin reflective layer with an array of transmitting apertures or an array or grid of conducting wires wherein the size of the apertures is generally larger than the wavelength of an optical beam being focused by the imaging system.

In comparison to certain catoptric and catadioptric imaging systems that comprise a non-thin beam-splitter, the use of a thin beam-splitter reduces the magnitude of off-axis aberrations and further reduces the optical path length of measurement beams in a refractive medium which is particularly important when working in the IR, VUV, or EUV. For a catoptric imaging system comprising a pellicle or aperture-array beam-splitter, the EUV range includes wavelengths shorter than 100 nm and for a catadioptric imaging system comprising a pellicle or aperture-array beam-splitter, the VUV range includes wavelengths down to approximately 120 nm. The catoptric or catadioptric imaging system may be configured to have a large working distance, e.g., 6 mm.

The catoptric or catadioptric imaging system may be employed in interferometric or non-interferometric imaging systems operating in a reflecting mode to measure properties of fields reflected/scattered by a measurement object or substrate or in a transmission mode to measure properties of fields transmitted/scattered by a measurement object or substrate, e.g., a reticle mask. Multiple catoptric and/or catadioptric imaging systems may be employed simultaneously to image a measurement object to achieve a large numerical aperture of ≈0.9 or larger with substantially no central obstruction of fields reflected/scattered or transmitted/scattered by the measurement object.

The positions and orientations of the reflecting elements of the one or more adaptive surfaces are controlled by transducers and a servo control system. The use of multi-element adaptive catoptric surfaces makes it possible to relax tolerances on the surface figures and locations of surfaces of the reflecting elements in the catoptric or catadioptric imaging system, makes it possible to introduce a mode of operation such that the image of a plane section of a measurement object is fixed in an image plane for a short period of time that covers the duration of a beam pulse generating the image although the plane section of the measurement object is moving in the object space at a high slew rate, makes it possible to introduce modes of operation that increases the speed at which lateral and vertical scans of a substrate may be implemented, makes it possible to introduce modes of operation that increase the signal-to-noise ratios for image information generated with the catoptric or catadioptric imaging system, makes it possible to operate in either a differential or non-differential interferometric mode with the option of switching rapidly between either of the differential or the non-differential modes of operation, and makes it possible to rapidly switch between two other different modes of operation wherein in one mode conjugated quadratures of reflected/scattered or transmitted/scattered fields of fields that have far-field properties are measured and in the second mode conjugated quadratures of reflected/scattered fields or transmitted/scattered fields of fields that have evanescent-field properties are measured.

A general description of embodiments incorporating the present invention will first be given for interferometer systems wherein either a N-dimensional bi- or quad-homodyne detection method is used where N is an integer. Referring to FIG. 1a, an interferometer system is shown diagrammatically comprising an interferometer 10, a source 18, a beam-conditioner 22, a detector 70, an electronic processor and controller 80, and a measurement object shown as substrate 60. Source 18 generates input beam 20. The interferometer system shown in FIG. 1a is for the case of an imaging system operating in a reflecting mode to measure properties of fields reflected/scattered by substrate 60. For the case of operation in a transmission mode, a portion of beam 24 split off as a measurement beam is incident on substrate 60 from the backside of substrate 60 such as shown diagrammatically in FIG. 3a. Source 18 is preferably a pulsed source that generates beam 20 with a single frequency component. Beam 20 is incident on and exits beam-conditioner 22 as input beam 24 that has the one or more frequency components. Alternatively, source 18 generates beam 20 with two frequency components that may have different polarization states wherein input beam 24 has one or more frequency components for each of the different polarization states. The different frequency components of the measurement beam components of input beam 24 are coextensive in space, the different frequency components of the reference beam components of input beam 24 are coextensive in space, and the different frequency components of both the reference and measurement beam components have the same temporal window function. Further description of source 18 and beam-conditioner 22 is the same as the corresponding description in commonly owned U.S. Provisional Patent Application 60/602,046 filed Aug. 16, 2004 entitled "Apparatus and Method for Joint And Time Delayed Measurements of Components of Conjugated Quadratures of Fields of Reflected/Scattered and Transmitted/Scattered Beams by an Object in Interferometry" by Henry A. Hill of which the contents are herein incorporated in their entirety by reference.

The interferometric type embodiments of the present invention operating in either the reflecting or transmitting mode are all of the type wherein conjugated quadratures of fields reflected/scattered or transmitted/scattered, respectively, are measured. For each of the embodiments, non-interferometric variants are obtained by the omission of the reference beam wherein only the intensity of fields reflected/scattered or transmitted/scattered, respectively, are measured.

Interferometer 10 comprises a catadioptric imaging system that may have one or more adaptive reflecting surfaces. The shapes of the one or more adaptive reflecting surfaces are controlled by a signal 98 from servo controller 96 according to error signal 94 from electronic processor and controller 80.

Reference and measurement beams are generated in either beam-conditioner 22 or interferometer 10 for each of the frequency components of input beam 24. The measurement or probe beam generated in either beam-conditioner 22 or interferometer 10 is one component of beam 30, beam 30A. Beam 30 further comprises a return reflected/scattered measurement beam 30B that is generated by the reflection/scattering of the measurement beam component 30A by substrate 60. The return measurement beam component 30B is combined with the reference beam in interferometer 10 to form a mixed beam. In certain embodiments, the mixed beam is incident on a thin fluorescent layer and output beam 34 comprises an optical interference beam generated by fluorescence. In certain other embodiments, output beam 34 comprises the mixed optical beam.

Output beam 34 is detected by detector 70 to generate an electrical interference signal 72 from either the optical interference beam generated by fluorescence from the mixed output beam in the certain embodiments or from the mixed optical beam in the certain other embodiments. The composition of the thin fluorescent layer is selected such that the decay time of the fluorescence is much shorter than the read out time of detector 70.

Detector 70 may comprise in the certain other embodiments an analyzer to select common polarization states of the reference and return measurement beam components of beam 34 to form a mixed beam in lieu of beam 34 being formed as a mixed beam.

Substrate 60 is translated by stage 90 wherein substrate 60 is mounted on wafer chuck 84 with wafer chuck 84 mounted on stage 90. The position of stage 90 is controlled by transducer 82 according to servo control signal 78 from electronic processor and controller 80. The position of stage 90 is measured by metrology system 88 and position information acquired by metrology system 88 is transmitted as signal 76 to electronic processor and controller 80 to generate an error signal for use in the position control of stage 90. Metrology system 88 may comprise for example linear displacement and angular displacement interferometers and cap gauges. The elevation and angular orientation of substrate 60 is controlled by transducers 86A and 86B according to servo control signal 78.

In the practice of the present invention wherein bi- or quad-homodyne detection methods are used, known phase shifts are introduced by either of two techniques between the reference and measurement beam components of mixed beam 34 generated by interferometer system 10. In one technique, phase shifts are introduced between the reference and measurement beam components for each of the frequency components by beam-conditioner 22 as controlled by signal 74 from electronic processor and controller 80. In the second technique, phase shifts are introduced between the reference and measurement beam components of mixed beam 34 for each of the frequency components as a consequence of frequency shifts introduced to the frequency components of input beam 24 by beam-conditioner 22 as controlled by signal 74 from electronic processor and controller 80.

In the practice of the present invention wherein N-dimensional bi- and quad-homodyne detection methods are used, additional phase shifts are introduced between each corresponding reference and measurement beam portion of N portions of the mixed beam generated by interferometer 10. The additional phase shifts are in addition to those introduced in the implementation of bi- or quad-homodyne detection methods. The additional phase shifts are generated in interferometer 10 by causing changes in the locations of elements of the adaptive catoptric surfaces.

Figure 1B:
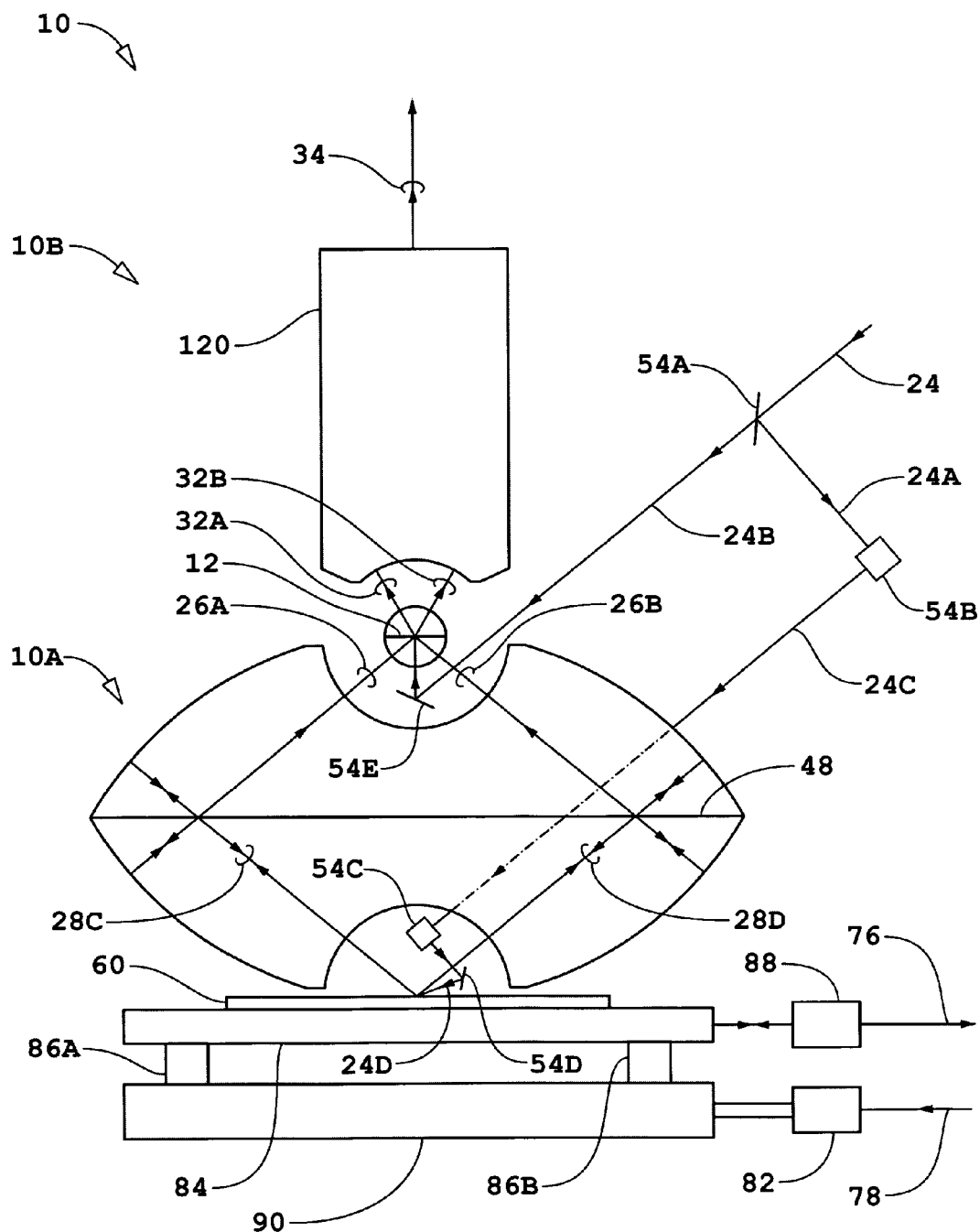
FIG. 1b is a schematic diagram of an interferometric non-confocal microscope system that uses a catadioptric imaging system.

Interferometer 10 of the first embodiment of the present invention is shown schematically in FIG. 1b. Interferometer 10 of the first embodiment comprises a first imaging system generally indicated as numeral 10A, thin fluorescent layer 12, and a second imaging system generally indicated as numeral 10B. The second imaging system 10B may comprise a low power microscope having a large working distance, e.g. Nikon ELWD and SLWD and Olympus LWD, ULWD, and ELWD objectives or a high resolution catadioptric imaging system such as described in cited U.S. Pat. No. 6,552,852 and U.S. Pat. No. 6,717,736.

The first imaging system 10A is a catadioptric imaging system such as described in cited U.S. Pat. No. 6,552,852 and U.S. Pat. No. 6,717,736; U.S. Provisional Patent Applications No. 60/447,254, No. 60/448,360, No. 60/448,250, No. 60/442,982, No. 60/459,425, No. 60/485,255, and No. 60/501,666; U.S. patent applications Ser. No. 10/778,371 entitled "Transverse Differential Interferometric Confocal Microscopy," Ser. No. 10/782,057 entitled "Longitudinal Differential Interferometric Confocal Microscopy," Ser. No. 10/782,058 entitled "Thin Film Metrology Using Interferometric Confocal Microscopy," Ser. No. 10/765,229 entitled "Interferometric Confocal Microscopy Incorporating Pinhole Array Beam-Splitter," and Ser. No. 10/816,180 entitled "Apparatus and Method for Joint Measurement Of Fields Of Orthogonally Polarized Beams Scattered/Reflected By An Object In Interferometry;" and U.S. Patent Application 60/485,255 filed Jul. 7, 2004 entitled "Apparatus and Method for Ellipsometric Measurements with High Spatial Resolution." Catadioptric imaging system 10A is shown schematically in FIG. 1c with adaptive reflective surfaces 42A-1, 42A-2, 42A-3, 42C-1, 42C-2, 42C-3, 46A-1, 46A-2, 46C-1, and 46C-2. The adaptive reflective surfaces with transducers and servo control signals are shown schematically in FIG. 1d. Catadioptric imaging system 10A comprises catadioptric elements 40 and 44, beam-splitter 48, and convex lens 50. Surfaces 42A and 42C comprise a first single convex spherical surface and 46A and 46C comprise a second single convex spherical surface wherein the first and second convex spherical surfaces have the same nominal radii of curvature and the respective centers of curvature of the first and second convex spherical surfaces are conjugate points with respect to beam-splitter 48. Surfaces 42B and 46B are concave spherical surfaces with nominally the same radii of curvature. The centers of curvature of surfaces 42B and 46B are the same as the centers of curvature of the second and first convex spherical surfaces, respectively. The center of curvature of convex lens 50 is the same as the center of curvature of surfaces 42B and the second convex spherical surface.

The radius of curvature of surface 46B is selected so as to minimize the loss in efficiency of the imaging system 10A, i.e., to minimize the relative diameter of surface 46B, and to produce a working distance for imaging system 10A acceptable for an end use application.

The radius of curvature of convex lens 50 is selected so that off-axis aberrations of the catadioptric imaging system 10A are compensated. The medium of elements 40 and 44 may for example be $CaF_2$, fused silica, UV grade fused silica, fluorine-doped fused silica ($F—SiO_2$), or commercially available glass such as SF11. The medium of convex lens 50 may be for example $CaF_2$, fused silica, UV grade fused silica, $F—SiO_2$, YAG, or commercially available glass such as SF11. An important consideration in the selection of the medium of elements 40 and 44 and convex lens 50 will the transmission properties for the frequencies of beam 24.

Convex lens 52 has a center of curvature the same as the center of curvature of convex lens 50. Convex lenses 50 and 52 are bonded together with the thin fluorescent layer 12 in between. The thin fluorescent layer 12 serves as the function of the beam combining beam-splitter in interferometer 10.

The second imaging system 10B is designed to image the thin fluorescent layer 12 onto the photosensitive surface of detector 70. The wavelength of beam 32 that is generated by the thin fluorescent layer 12 and comprising beams 32A and 32B will in general be in the visible which simplifies the design of the second imaging system 10B and detector 70. The composition of the thin fluorescent layer 12 is selected such that the decay time of the fluorescence of the thin fluorescent layer 12 is significantly less than the read out time of detector 70.

The catoptric surfaces of catadioptric imaging system 10A comprise reflecting surfaces 42A-1, 42A-2, and 42A-3 associated with refractive surface 42A; reflecting surfaces 42C-1, 42C-2, and 42C-3 associated with refractive surface 42C; reflecting surfaces 46A-1 and 46A-2 associated with refractive surface 46A; and reflecting surfaces 46C-1 and 46C-2 associated with refractive surface 46C. The catoptric surfaces of catadioptric imaging system 10A further comprise those portions of surfaces 42A, 42C, 46A, and 46C that do not have an adjacent reflective element and are coated with a reflective coating. The portions of refractive surfaces 42A, 42C, 46A, and 46C that have adjacent reflective elements are not coated and thus transmit beams incident thereon.

Reflecting surfaces 42A-1, 42A-2, 42A-3, 42C-1, 42C-2, and 42C-3 comprise nominally a single concave reflecting surface that has a nominal center of curvature the same as the first convex surface. Reflecting surfaces 46A-1 and 46A-2, 46C-1, and 46C-2 comprise nominally a single concave reflecting surface that has a nominal center of curvature the same as the second convex surface. The radial distances between the adaptive reflective surfaces 42A-1, 42A-2, 42A-3, 42C-1, 42C-2, 42C-3, 46A-1, 46A-2, 46C-1, and 46C-2 and associated refractive surfaces of portions of refractive surfaces 42A, 42C, 46A, and 46C are of the order of a few microns. The radial distances could be as large as millimeters with corresponding increases in the radii of curvature of adaptive reflecting surfaces 42A-1, 42A-2, 42C-1, 42C-2, 46A-1, 46A-2, 46C-1, and 46C-2.

Figure 1C:
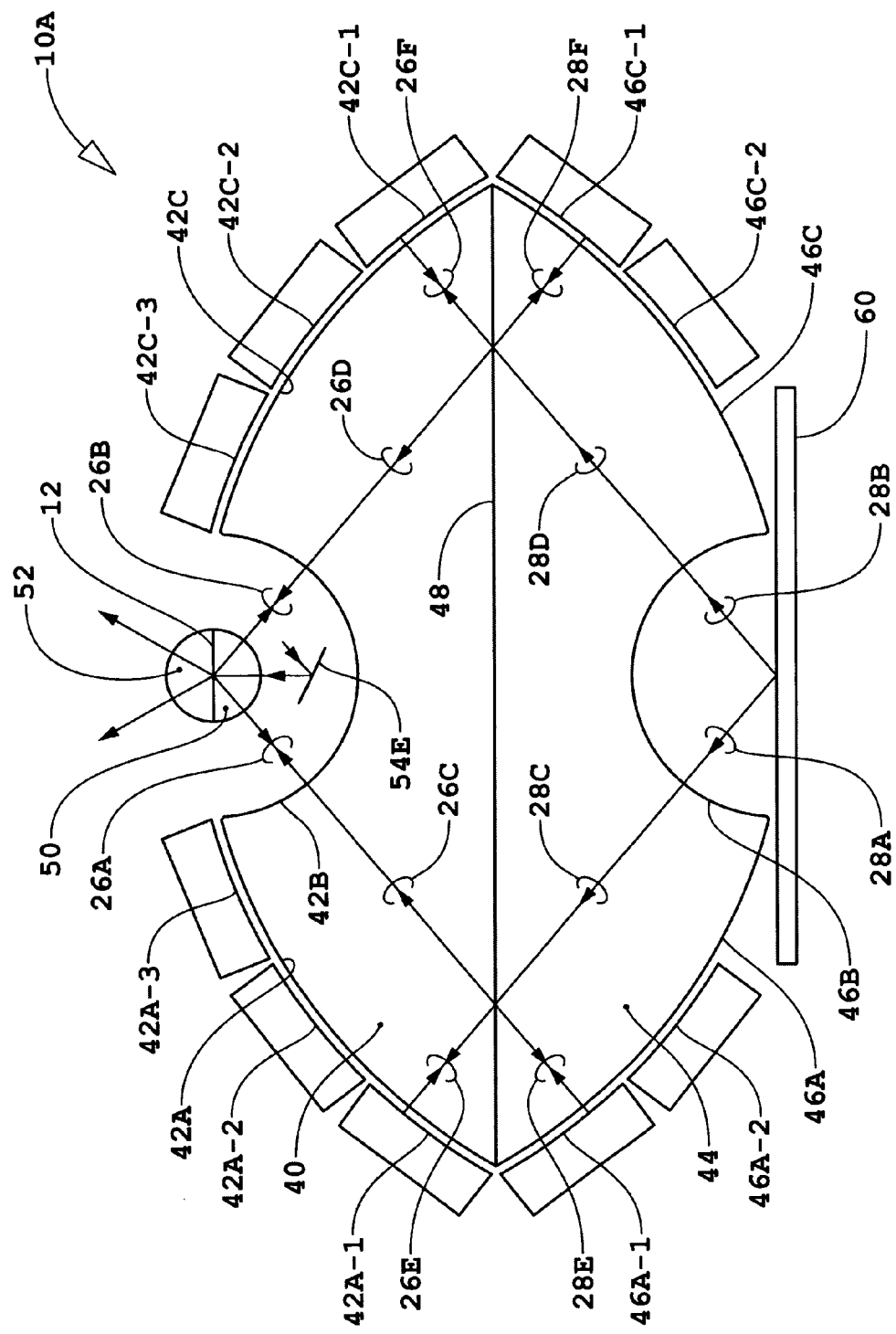
FIG. 1c is a diagram of a catadioptric imaging system comprising adaptive catoptric reflecting surfaces.

Adaptive reflecting surfaces 42A-1, 42A-2, 42A-3, 42C-1, 42C-2, and 42C-3 and adaptive reflecting surfaces 46A-1, 46A-2, 46C-1, and 46C-2 shown in FIG. 1c may each be representative of annular rings or of sections of annular rings. The remaining description of the first embodiment will be based on the simple configuration wherein there are no additional reflecting surfaces beyond those described as a non-limiting example without departing from the scope and spirit of the present invention. The number of corresponding adaptive reflecting surfaces defines of the values of N that may be used in the N-dimensional bi- and quad-homodyne detection methods. In the non-limiting example of the simple configuration shown in FIG. 1c, the maximum value for N is 6.

Figure 1D:
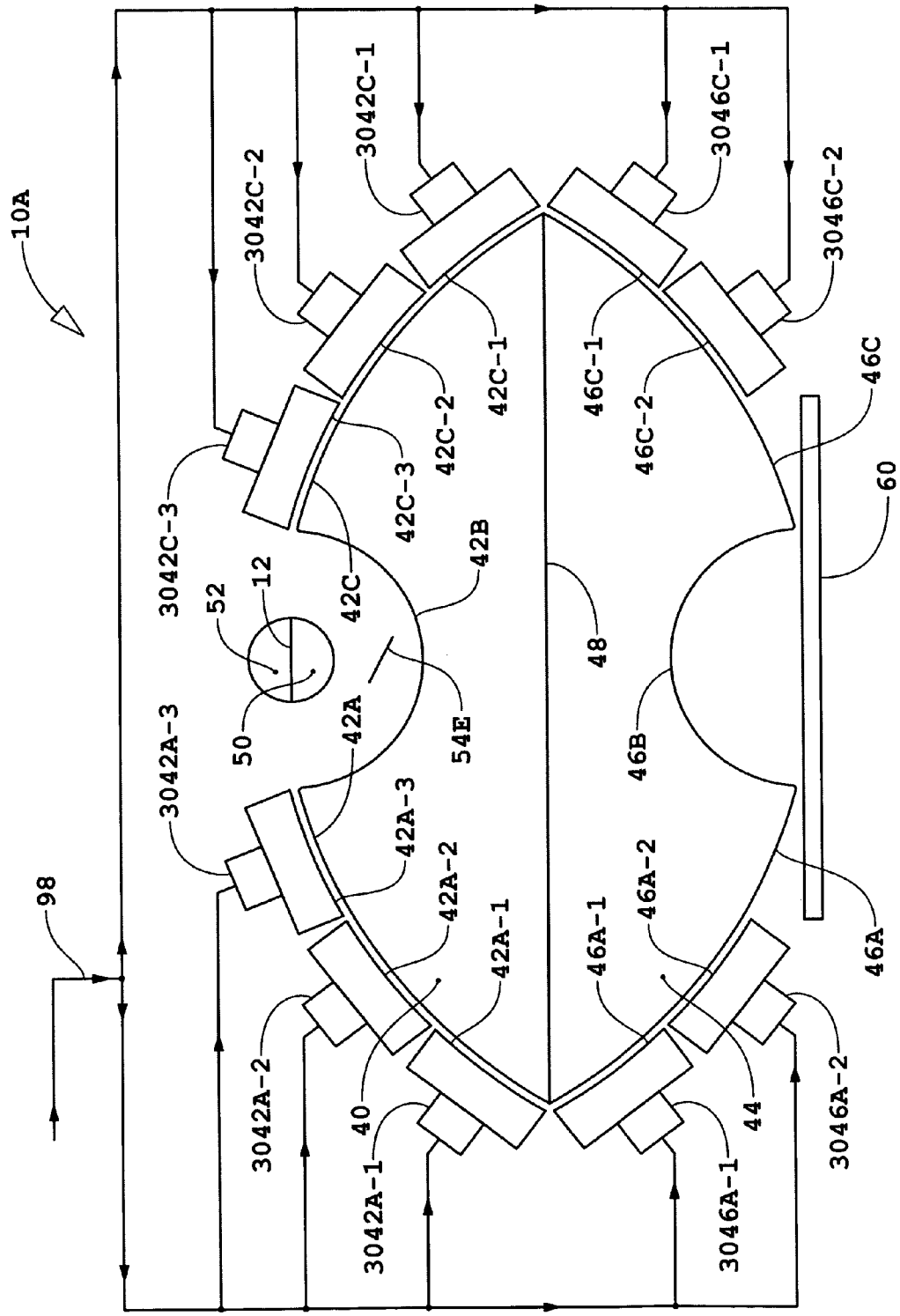
FIG. 1d is a diagram of a catadioptric imaging system comprising adaptive catoptric surfaces attached to displacement transducers.

Referring to FIG. 1d, the locations and orientations of adaptive reflecting surfaces are controlled by transducers according to servo control signal 98 from servo controller 96. For each of the adaptive reflective surfaces 42A-1, 42A-2, 42A-3, 42C-1, 42C-2, 42C-3, 46A-1, 46A-2, 46C-1, and 46C-2, there are corresponding transducers 3042A-1, 3042A-2, 3042A-3, 3042C-1, 3042C-2, 3042C-3, 3046A-1, 3046A-2, 3046C-1, and 3046C-2, respectively. Each of the transducers comprise three transducers that can either change the radial position of a corresponding adaptive reflective surface or effect changes in the orientation of the corresponding adaptive reflective surface in two orthogonal planes. The two orthogonal planes intersect in a line that is parallel to the corresponding optical axis of the corresponding adaptive reflective surface.

Referring to FIG. 1b, input beam 24 is incident on a non-polarizing beam-splitter 54A wherein a first portion thereof is reflected as a measurement beam 24A and a second portion of input beam 24 is incident on non-polarizing beam-splitter 54A is transmitted as reference beam 24B. Measurement beam 24A is incident on optical element 54B and exits as measurement beam 24C. Optical element 54B comprises two mirrors such beam 24C is displaced out of the plane of FIG. 1b and directed toward optical element 54C. Beam 24C exits optical element 54C as measurement beam 24D after reflection by mirror 54D. Optical element 54C comprises two mirrors such that the measurement beam that exits optical element 54D is in the plane of FIG. 1b and directed toward mirror 54D. Reference beam 24B is incident on thin fluorescent layer 12 after reflection by mirror 54E. When input beam 24 comprises non-coextensive reference and measurement beams, element 54A functions as mirror to reflect the measurement beam component of beam 24 as beam 24A and the reference beam component beam 24B of beam 24 is not incident on element 54A.

Measurement beam 24D or probe beam is incident on substrate 60 and portion thereof are reflected/scattered to form reflected/scattered measurement beams 28A and 28B (see FIG. 1c). Measurement beam 24D and reflected/scattered measurement beams 28A and 28B comprise measurement beam 30 shown in FIG. 1a. Measurement beam 28A is incident on beam-splitter 48 and first and second portions thereof are transmitted and reflected, respectively, as components of beams 26E and 28E, respectively. The description of the subsequent propagation of the components of beams 26E and 28E will be in terms of N portions wherein the description of each portion of the N portions is substantially the same. The portions of the components of beams 26E and 28E corresponding to one of the portions of the N portions that are subsequently reflected by reflective surfaces 42A-1 and 46A-1, respectively, are portions of components of beams 26E and 28E, respectively, directed toward beam-splitter 48 after two transmissions by refractive surfaces 42A and 46A, respectively. First and second portions of components of beam 26E directed toward beam-splitter 48 are reflected and transmitted, respectively, as components of beam 26C and 28C, respectively. First and second portions of components of beam 28E directed toward beam-splitter 48 are transmitted and reflected, respectively, as components of beam 26C and 28C, respectively.

The amplitude A of beam 26C comprising the first portions of beams 26E and 28E reflected and transmitted by beam-splitter 48, respectively, relative to the amplitude of the corresponding portion of beam 28C is given by the equation $$A = T(\theta)^{1/2} R(\theta)^{1/2} (1 + \cos\phi) \quad (1)$$

where θ is an angle of incidence at beam-splitter 48 of the first portions of beams 26E and 28E reflected and transmitted by beam-splitter 48, respectively, and $T(\theta)^{1/2}$ and $R(\theta)^{1/2}$ are the complex transmission and reflection amplitude coefficients, respectively, and φ is the relative phase shift between the first portions of beams 26E and 28E reflected and transmitted, respectively, by beam-splitter 48. A maximum value for the amplitude A is obtained by the adjustment of the relative radial positions of reflective surfaces 42A-1 and 46A-1 to achieve the condition $$\phi = 0, 2\pi, 4\pi, \ldots \quad (2)$$

The condition is achieved by control of respective transducers with signal 98 from servo controller 96.

Catadioptric imaging system 10A is functionally equivalent to the imaging properties of an interface wherein the index of refractions on the two sides of the interface are 1 and −1, respectively, when there is constructive interference between the measurement beam components of beam 26C and 26D. When there is constructive interference between the measurement beam components, the complex amplitude of the interferometric conjugate image relative to the amplitude that would be achieved by a lossless otherwise equivalent imaging system with respect to pupil function is equal to $$2T(\theta)^{1/2} R(\theta)^{1/2}. \quad (3)$$

The combination of a reflection and a transmission for each ray of the converging beams forming the interferometric conjugate image at center of curvature 60 substantially compensates for departure of properties of beam-splitter 48 from properties of an ideal beam-splitter. The compensation is demonstrated by Equation (3). Function $T(\theta)^{1/2} R(\theta)^{1/2}$ has a maximum at $T(\theta) = R(\theta) = \frac{1}{2}$ and has only a second order dependence on changes of the transmission/reflection properties, i.e., $[T(\theta)^{1/2} - 1/\sqrt{2}][R(\theta)^{1/2} - 1/\sqrt{2}]$.

The average intensity transmission of the first embodiment is increased by a factor of 2 as demonstrated by Equation (3) than would otherwise be obtained as a result of use of the constructive interference of beams formed by the two different paths through the imaging system of the first embodiment. The constructive interference is achieved in the first embodiment by the adjustment of the relative radial positions of conjugate adaptive reflective surfaces by servo control signal 98. The determination of the correct values for the servo control signal 98 is made during an initialization period of the first embodiment by adjusting for example the relative servo control signal components for corresponding conjugate adaptive reflective surfaces to yield a maximum value in the amplitude of the conjugate image. Other techniques can be used for the determination of the correct values for the components of servo control signal 98 such as introducing phase modulations at a set of non-redundant frequencies and measuring the amplitudes of components of transmitted beams at the non-redundant frequencies.

AR Coating Requirements

In the first embodiment of the present invention, no AR or anti-reflective coating is required on the portions of refractive surfaces 42A, 42C, 46A, and 46C associated with the adaptive reflective surfaces 42A-1, 42A-2, 42A-3, 42C-1, 42C-2, 42C-3, 46A-1, 46A-2, 46C-1, and 46C-2 to achieve a maximum amplitude for components of beam 26E, 26F, 28E, and 28F.

Adaptive reflective surfaces 42A-1, 42A-2, 42A-3, 42C-1, 42C-2, 42C-3, 46A-1, 46A-2, 46C-1, and 46C-2 and associated portions of refractive surfaces 42A, 42C, 46A, and 46C are separated by radial distances typically of the order of a few microns and form an asymmetric Fabry-Perot cavity. The asymmetric Fabry-Perot cavity comprises a rear mirror that has a high reflectivity and a front mirror as a partially reflecting dielectric interface and is an example of the Gires-Tournois etalon. The beam reflected by a Gires-Tournois etalon is to a high accuracy a purely phase-modulated beam. With a reflectivity of R=0.04 for the front mirror, the relationship between the phase shift introduced by the etalon and the optical path length of the etalon cavity is represented by a linear relationship with a cyclic error that is principally a small amplitude second harmonic cyclic error. The amplitude in phase produced by the second harmonic cyclic error is approximately $2\sqrt{R} = 0.4$ radians. In the first embodiment of the present invention, the effect of the cyclic errors is easily measured in an initialization phase of the first embodiment and subsequently compensated through control of the thickness of the cavities without any modulation of the intensity of the reflected beams.

Relaxation of Surface Tolerances

The surface tolerances on portions of refractive surfaces 42A, 42C, 46A, and 46C associated with the adaptive reflective surfaces 42A-1, 42A-2, 42A-3, 42C-1, 42C-2, 42C-3, 46A-1, 46A-2, 46C-1, and 46C-2 are relaxed in the first embodiment as a result of two effects. The first of the two effects is that the net effect of an error in the surface figure of a refractive surface on a double transmission through the refractive surface is reduced relative to the effect of the same error in the surface figure of mirror on an internally reflected beam by a factor of $$\frac{n-1}{n} \quad (4)$$

where n is the index of refraction of the refractive medium and mirror substrate.

The second of the two effects is that the average local errors in the surface figures of the portions of refractive surfaces 42A, 42C, 46A, and 46C associated with the adaptive reflective surfaces 42A-1, 42A-2, 42A-3, 42C-1, 42C-2, 42C-3, 46A-1, 46A-2, 46C-1, and 46C-2 are compensated by adjusting the radial positions of the portions of the adaptive reflective surfaces 42A-1, 42A-2, 42A-3, 42C-1, 42C-2, 42C-3, 46A-1, 46A-2, 46C-1, and 46C-2. In the first embodiment of the present invention, the effect of the average local errors are easily measured in an initialization phase of the first embodiment and subsequently compensated through the control of the radial positions of the adaptive reflective surfaces 42A-1, 42A-2, 42A-3, 42C-1, 42C-2, 42C-3, 46A-1, 46A-2, 46C-1, and 46C-2.

The second of the two effects can relax the tolerances of the manufacture of the first and second single convex surfaces by a factor of 2 or more.

Manufacture of High Precision Adaptive Reflective Surfaces: Replication

Adaptive reflective surfaces 42A-1, 42A-2, 42A-3, 42C-1, 42C-2, 42C-3, 46A-1, 46A-2, 46C-1, and 46C-2 can be generated by standard optical grinding and polishing techniques. However, improved performance for the catadioptric imaging system 10A is achieved at a lower cost by generating the adaptive reflective surfaces by the process of replication. A master used in the replication process is selected as the best portion of a surface such as the first or second single convex surfaces comprising surfaces 42A and 42C, respectively, and surfaces 46A and 46C, respectively. The master or a secondary master generated from the master by replication of first a negative replication and then a positive replication is first coated with a release agent, a reflective layer comprising a single or multiple layers is deposited on the release agent coated surface, and then a backing element is applied to the reflecting layer by a bonding agent. After the bonding agent is cured, the backing element, the cured bonding agent, and the reflective layer is separated from the master or secondary master at the release agent interface. Thus, adaptive reflective surfaces 42A-1, 42A-2, 42A-3, 42C-1, 42C-2, 42C-3, 46A-1, 46A-2, 46C-1, and 46C-2 are manufactured with surface figures that have a significantly higher precision than the precision of the surfaces of the first and second single convex surfaces.

Use of Conjugate Adaptive Reflective Surfaces as Optical Switches

Each conjugate pair of adaptive reflective surfaces 42A-1, 42A-2, 42A-3, 42C-1, 42C-2, 42C-3, 46A-1, 46A-2, 46C-1, and 46C-2 have been described in terms of maximizing the corresponding portions of amplitudes of beams 26C and 26D [see discussion associated with respect to Equation (1)]. It is apparent on examination of Equation (1) that each of the conjugate pairs of adaptive reflective surfaces may also be used as an optical switch by adjusting the corresponding $\phi$ such that $$\phi = \pi, 3\pi, \ldots \quad (5)$$

The condition expressed by Equation (5) is achieved by control of respective transducers with signal 98 from servo controller 96.

The optical switch mode of operation of the conjugate pairs of adaptive reflective surfaces can be beneficially used in initialization phases of the first embodiment of the present invention. For example, in the initialization phase for the determination of the correct relative phases of conjugate pairs of adaptive reflective surfaces, properties of a pair of conjugate surfaces of the array of conjugate pairs can be individually measured by switching off the complimentary set of array of conjugate pairs.

Note that this procedure automatically compensates for the average local errors in the surface figures of the portions of refractive surfaces 42A, 42C, 46A, and 46C associated with the adaptive reflective surfaces 42A-1, 42A-2, 42A-3, 42C-1, 42C-2, 42C-3, 46A-1, 46A-2, 46C-1, and 46C-2.

The optical switch mode of operation of the conjugate pairs of adaptive reflective surfaces can also beneficially be use to switch from different modes of operation of the first embodiment of the present invention. The different modes of operation may comprise different values for N.

Use of Conjugate Adaptive Reflective Surfaces as Phase Shifters

Phases of portions of beam 26C and 26D associated with adaptive reflective surfaces 42A-1, 42A-2, 42A-3, 42C-1, 42C-2, 42C-3, 46A-1, 46A-2, 46C-1, and 46C-2 may be shifted in the first embodiment of the present invention by adjusting the radial positions of the adaptive reflective surfaces 42A-1, 42A-2, 42A-3, 42C-1, 42C-2, 42C-3, 46A-1, 46A-2, 46C-1, and 46C-2 while maintaining the condition given by Equation (2). In particular, the phases of portions of 26C and 26D associated with adaptive reflective surfaces 42A-1, 42A-2, 42A-3, 42C-1, 42C-2, 42C-3, 46A-1, 46A-2, 46C-1, and 46C-2 may be shifted between the values of $$0 \text{ and } \pi. \quad (6)$$

This phase shifting feature is used in the implementation of the subsequently described N-dimensional bi- and quad-homodyne detection methods of the present invention.

Differential Measurements

The phase shift feature of the first embodiment of the present invention described with respect to Equation (6) can be used to obtain differential measurements of properties of the measurement beams reflected/scattered by substrate 60. The differential measurements are with respect to changes of the amplitudes of the measurement beams reflected/scattered by substrate 60 as a function of reflection/scattering angle.

The Use of Conjugate Adaptive Reflective Surfaces to Compensate for Optical Aberrations When a plane section of substrate 60 that is being imaged by interferometer 10 of the first embodiment of the present invention is embedded below the surface of substrate 60, spherical aberrations will be introduced such as described in commonly owned U.S. Provisional Patent Application No. 60/444,707 entitled "Compensation for Effects of Mismatch in Indices of Refraction at a Substrate-Medium Interface in Confocal and Interferometric Confocal Microscopy" and U.S. patent application Ser. No. 10/771,785 entitled "Compensation for Effects of Mismatch in Indices of Refraction at a Substrate-Medium Interface in Confocal and Interferometric Confocal Microscopy" wherein both the provisional and non-provisional patent applications are by Henry A. Hill and the contents of which are herein incorporated in their entirety by reference. Aberrations may also be introduced by a pellicle beam-splitter or aperture-array beam-splitter. Certain of the aberrations are compensated in catadioptric imaging system 10A by changing the focal lengths of conjugate pairs of adaptive reflective surfaces 42A-1, 42A-2, 42C-1, 42C-2, 46A-1, 46A-2, 46C-1, and 46C-2. The focal lengths of the conjugate pairs of adaptive reflective surfaces are adjusted by changing the radial locations of the conjugate pairs of adaptive reflective surfaces 42A-1, 42A-2, 42C-1, 42C-2, 46A-1, 46A-2, 46C-1, and 46C-2.

The surfaces represented by adaptive reflective surfaces 42A-1, 42A-2, 42A-3, 42C-1, 42C-2, and 42C-3 are changed in compensating for the effects of the spherical aberrations from a nominally spherical surface to a nominal aspherical surface. Also the surfaces represented by adaptive reflective surfaces 46A-1, 46A-2, 46C-1, and 46C-2 are changed in compensating for the effects of the spherical aberrations from a nominally spherical surface to a nominal aspherical surface.

Use of Conjugate Adaptive Reflective Surfaces to Generate Vertical and Lateral Scans A vertical scan of plane sections of substrate 60 is implemented in the first embodiment of the present invention by scanning the focal lengths of conjugate pairs of adaptive reflective surfaces 42A-1, 42A-2, 42A-3, 42C-1, 42C-2, 42C-3, 46A-1, 46A-2, 46C-1, and 46C-2. The focal lengths of the conjugate pairs of adaptive surfaces are adjusted by scanning the radial locations of the conjugate pairs of adaptive surfaces 42A-1, 42A-2, 42C-1, 42C-2, 46A-1, 46A-2, 46C-1, and 46C-2.

A lateral scan of a plane section of substrate 60 is implemented in the first embodiment of the present invention by scanning the centers of curvature of adaptive reflective surfaces 42A-1, 42A-2, 42A-3, 42C-1, 42C-2, 42C-3, 46A-1, 46A-2, 46C-1, and 46C-2. The centers of curvatures of the adaptive surfaces are adjusted by scanning the angular orientations of the adaptive reflective surfaces 42A-1, 42A-2, 42C-1, 42C-2, 46A-1, 46A-2, 46C-1, and 46C-2.

The bandwidth of the speeds of the vertical and lateral scans of substrate 60 are determined in the first embodiment by the bandwidth of the scanning speeds in radial positions and angular orientations, respectively, of the adaptive reflective surfaces 42A-1, 42A-2, 42A-3, 42C-1, 42C-2, 42C-3, 46A-1, 46A-2, 46C-1, and 46C-2. The bandwidths of the scanning speeds of the adaptive reflective surfaces will generally be orders of magnitude larger than either the bandwidth of vertical and lateral scans that can be generated by translating the interferometer system 10 and detector system 70 or the bandwidth of vertical and lateral scans that can be generated by physically translating the vertical and lateral position of substrate 60 and wafer chuck 84.

Periodically Stationary Images of a Scanning Object or Substrate

The use of multi-element adaptive catoptric makes it possible to introduce a mode of operation such that the image of a plane section of an object or substrate 60 is fixed in an image plane for a short period of time, i.e., instantaneously stationary, that covers the time span of a beam pulse generating the image although the plane section of the object is moving in the object space at either a low or high slew rate. The instantaneously stationary image of a scanning object is obtained by using the described property of the present invention entitled "Use of Conjugate Adaptive Reflective Surfaces to Generate Vertical and Lateral Scans." The conjugate adaptive reflective surfaces are driven to introduce a lateral scan of the image of the fluorescent thin layer 12 in the plane section of the object with a scan speed equal to the scan speed of substrate 60 during the period of a pulse of source 18.

The sequence of periods when the image of the fluorescent thin layer 12 in the plane section of the object or substrate 60 are moving collinearly will correspond to the sequence of periods of the pulses of source 18. For a pulse train that is uniform in time, the periods of stationary images of a scanning substrate 60 will be periodic in time.

Selection of Radii of Curvature

The description of the considerations made in the selection of radii of curvature of the first single convex surface comprising surfaces 42A and 42C, the second single convex surface comprising surfaces 46A and 46C, concave surfaces 42B and 46B, the adaptive reflective surfaces 42A-1, 42A-2, 42A-3, 42C-1, 42C-2, 42C-3, 46A-1, 46A-2, 46C-1, and 46C-2 are that same as the description given for the selection of radii of corresponding optical surfaces in the third embodiment of the present invention and in the cited U.S. Provisional Patent Application No. 60/485,255 and U.S. Patent Application 60/485,255 filed Jul. 7, 2004 entitled "Apparatus and Method for Ellipsometric Measurements with High Spatial Resolution." The description of the selection of the radius of curvature associated with element 50 is the same as the description of the selection of the corresponding optical surface in the third embodiment of the present invention and in the cited U.S. Provisional Patent Application No. 60/485,255 except that the radius of curvature associated with element 50 are ½ of the radius of curvature of the corresponding optical surface in the third embodiment and in the cited U.S. Provisional Patent Application No. 60/485,255.

N-Dimensional Bi- and Quad-Homodyne Detection Methods

The description of source 18 including a pulse mode of operation and beam-conditioner 22 is the same as the corresponding portions of the description given to the source and beam-conditioner in embodiments described in commonly owned U.S. Provisional Patent Application No. 60/442,858 entitled "Apparatus and Method for Joint Measurements of Conjugated Quadratures of Fields of Reflected/Scattered Beams by an Object in Interferometry" and U.S. patent application Ser. No. 10/765,368 entitled "Apparatus and Method for Joint Measurements of Conjugated Quadratures of Fields of Reflected/Scattered or Transmitted Beams by an Object in Interferometry" wherein the provisional and the non-provisional patent applications are by Henry A. Hill and the contents of which are herein incorporated in their entirety by reference and in cited U.S. Provisional Patent Application No. 60/485,255, in cited U.S. Provisional Patent 60/602,046 filed Aug. 16, 2004 entitled "Apparatus and Method for Joint And Time Delayed Measurements of Components of Conjugated Quadratures of Fields of Reflected/Scattered and Transmitted/Scattered Beams by an Object in Interferometry," and in cited U.S. Patent Application 60/485,255 filed Jul. 7, 2004 entitled "Apparatus and Method for Ellipsometric Measurements with High Spatial Resolution." The beam-conditioner 22 may comprise acousto-optic modulators.

The descriptions the of bi-homodyne and quad-homodyne detection methods of the first embodiment of the present invention are the same as corresponding portions of the descriptions given for the descriptions of bi-homodyne and quad-homodyne detection methods in the cited U.S. Provisional Patent Application Nos. 60/442,858 and 60/485,255 and in cited U.S. patent application Ser. No. 10/765,368 and U.S. patent application filed Jul. 7, 2004 wherein the homodyne detection methods are based on frequency encoding. The extension of the bi- and quad-homodyne detection methods to N-dimensional bi- and quad-homodyne detection methods based on a combination of frequency encoding and either amplitude or phase modulations or permutations is implemented in the first embodiment by the use of the conjugate pairs of adaptive reflective surfaces of catadioptric imaging system 10A as optical switches or as π phase shifters, respectively. The extension of the bi- and quad-homodyne detection methods to N-dimensional bi- and quad-homodyne detection methods may also be based on a combination of frequency encoding, polarization encoding, and either amplitude or phase modulations or permutations. The description of bi- and quad-homodyne detection methods based on a combination of frequency and polarization encoding is the same as the corresponding description given in cited U.S. Provisional Patent Application No. 60/459,425 and in cited U.S. patent application filed Apr. 4, 2004 entitled "Apparatus and Method for Joint Measurement Of Fields Of Orthogonally Polarized Beams Scattered/Reflected By An Object In Interferometry."

The N-dimensional bi- and quad-homodyne detection methods are homodyne detection methods that exhibit the same properties as the cited bi- and quad-homodyne detection methods with respect to making joint measurements of conjugated quadratures of fields: a joint measurement of a conjugated quadratures of fields is made in the bi- and quad-homodyne detection methods and joint measurements are made of N independent conjugated quadratures of fields in the N-dimensional bi- and quad-homodyne detection methods where N is an integer. The (i,k) electrical interference signal $\Sigma_{i,k}$, $1 \le i \le N$ and $1 \le k \le 4$, is written in terms of the contribution $S_{i,j,k}$ that corresponds to portion j of the N portions of electrical interference signal $\Sigma_{i,k}$ associated with the conjugate pairs of adaptive reflective surfaces 42A-1, 42A-2, 42A-3, 42C-1, 42C-2, 42C-3, 46A-1, 46A-2, 46C-1, and 46C-2. The representation of $\Sigma_{i,k}$ in terms of $S_{i,j,k}$ is expressed as $$\Sigma_{i,k} = \sum_{j=1}^{N} h_{ij} S_{i,j,k}, \quad 1 \le i \le N, \, 1 \le k \le 4 \qquad (7)$$

where $h_{ij}$ are matrix elements $H=(h_{ij})$ are constants.

The values of matrix elements $h_{ij}$ are selected and controlled by conjugate adaptive reflective surfaces operating in either the phase shifting mode or the optical switching mode. In the phase shifting mode, the values of $h_{ij}$ are selected to be ±1 which corresponds to use of phase modulations or permutations. In the optical switching mode, the matrix elements $h_{ij}$ are selected to be either 0 or 1 which corresponds to amplitude modulations or permutations. In the case of phase modulations, the measurement of each of the N independent conjugated quadratures is made as a joint measurement and the N independent conjugated quadratures may be jointly measured with respect to each other. In the case of amplitude modulations, the measurement of each of the N independent conjugated quadratures is made as a joint measurement although the N independent conjugated quadratures are not jointly measured with respect to each other.

There are 4N values of electrical interference signal $\Sigma_{i,k}$ measured for each spot in or on substrate 60 that is being imaged. The number of different values of the electrical interference signal $\Sigma_{i,k}$ that is measured is 4 times the number of independent conjugated quadratures that are being measured because there are 2N independent components of conjugated quadratures measured and two measurements of electrical interference signal values are required for each independent component of conjugated quadratures. For further discussion, reference is made to the bi-homodyne detection method such as described in cited U.S. Provisional Patent Applications No. 60/442,858 and in cited U.S. patent applications filed Jan. 27, 2004 entitled "Apparatus and Method for Joint Measurements of Conjugated Quadratures of Fields of Reflected/Scattered and Transmitted Beams by an Object in Interferometry" and in commonly owned U.S. Provisional Patent Application No. 60/485,507 and in commonly owned U.S. patent application filed Jul. 7, 2004 and entitled "Apparatus And Method For High Speed Scan For Detection And Measurement of Properties of Sub-Wavelength Defects And Artifacts In Semiconductor And Mask Metrology" wherein conjugated quadratures of scattered/reflected or scattered/transmitted fields are obtained jointly with a set of four electrical interference signal values obtained for each spot on and/or in a substrate being imaged. The latter cited provisional and non-provisional applications are by Henry A. Hill and the contents of each are incorporated herein in their entirety by reference.

The contribution $S_{i,j,k}$ is represented for the bi-homodyne detection method within a scale factor by the formula $$S_{i,j,k} = P_{i,k} \sum_{m=1}^{2} \begin{Bmatrix} \xi_{i,k}^2 |A_{j,m}|^2 + \zeta_{i,k}^2 |B_{j,m}|^2 + \eta_{i,k}^2 |C_{j,m}|^2 + \\ \zeta_{i,k} \eta_{i,k} 2 |B_{j,m}||C_{j,m}|\cos\varphi_{B_{j,m}C_{j,m}} \varepsilon_{m,k} + \\ \xi_{i,k} \zeta_{i,k} 2 |A_{j,m}||B_{j,m}|\cos\varphi_{A_{j,m}B_{j,m}} \varepsilon_{m,k} + \\ \varepsilon_{m,k} \xi_{i,k} \eta_{i,k} [1-(-1)^m]|A_{j,m}||C_{j,m}|\cos\varphi_{A_{j,m}C_{j,m}} + \\ \varepsilon_{m,k} \xi_{i,k} \eta_{i,k} [1+(-1)^m]|A_{j,m}||C_{j,m}|\sin\varphi_{A_{j,m}C_{j,m}} \end{Bmatrix} \qquad (8)$$

where coefficient $A_{j,m}$ represents the amplitude of the reference beam corresponding to pulse (i,k) of input beam 24 and to the frequency component of the input beam 24 that has index m; coefficient $B_{j,m}$ represents the amplitude of the background beam corresponding to reference beam $A_{j,m}$; coefficient $C_{j,m}$ represents the amplitude of the return measurement beam corresponding to reference beam $A_{j,m}$; $P_{i,k}$ represents the integrated intensity of the first frequency component of the input beam 24 pulse (i,k) of a sequence of 4N pulses; and an example set of values for $\varepsilon_{m,k}$ are listed in Table 1. There are other set of values for $\varepsilon_{m,k}$ that may be used in embodiments of the present invention wherein the other set of values for $\epsilon_{m,k}$ satisfy the conditions set out in subsequent Equations (9) and (10) herein.

The change in the values of $\epsilon_{m,k}$ from 1 to −1 or from −1 to 1 corresponds to changes in relative phases of respective reference and measurement beams. The coefficients $\xi_{i,k}$, $\zeta_{i,k}$, and $\eta_{i,k}$ represent effects of variations in properties of a conjugate set of 4N pinholes such as size and shape if used in the generation of the spot on and/or in substrate 60, properties of a conjugate set of 4N pinholes such as size and shape if used at a conjugate set of 4N detector pixels corresponding to the spot on and/or in substrate 60, and the sensitivities of the conjugate set of 4N detector pixels for the reference, background, and the return measurement beam, respectively. In a single-frequency

TABLE 1

| | $\epsilon_{m,k}$ | |
| | m | |
| k | 1 | 2 |
| 1 | 1 | 1 |
| 2 | 1 | −1 |
| 3 | −1 | −1 |
| 4 | −1 | 1 | single-homodyne detection operating in a non-scanning mode, the conjugate set of pinholes corresponds to a single pinhole and the conjugate set of four pixels corresponds to a single pixel. In a single-frequency single-homodyne detection operating in a non-scanning mode, the conjugate set of four pinholes comprise pinholes of pinhole array beam-splitter 12 that are conjugate to a spot in or on the substrate being imaged at different times during the scan.

An important requirement of $\epsilon_{m,k}$ is that $$\sum_{k=1}^{4} \varepsilon_{m,k} = 0, m = 1, 2. \quad (9)$$

Another important requirement is that the $\epsilon_{m,k}$ are orthogonal over the range of m=1, 2 for m≠m' since $\epsilon_{m,k}$ and $\epsilon_{m',k}$ are orthogonal over the range of k=1, 2, 3, 4, i.e., $$\sum_{j=1}^{4} \varepsilon_{m,j} \varepsilon_{m',j} = 4\delta_{m,m'} \quad (10)$$

where $\delta_{m,m'}$ is the Kronecker delta defined by $\delta_{m,m'}=1$ for m=m', $\delta_{m,m'}=0$ for m≠m'. (11)

A set of conditions that are used to derive the matrix elements $h_{i,j}$ for the phase modulation or permutation embodiment are that the values of $h_{i,j}$ are either ±1 and that $$\sum_{j=1}^{N} h_{i,j} h_{i',j} = N\delta_{i,i'}. \quad (12)$$

Three examples of matrices $H=(h_{ij})$ which meet the requirements of the N-dimensional bi- and quad-homodyne detection methods when using phase modulations or permutations are as follows:

$$(h_{ij}) = \begin{pmatrix} 1 & 1 \\ 1 & -1 \end{pmatrix}, N = 2; \quad (13)$$

$$(h_{ij}) = \begin{pmatrix} 1 & 1 & 1 & 1 \\ 1 & -1 & 1 & -1 \\ 1 & 1 & -1 & -1 \\ 1 & -1 & -1 & 1 \end{pmatrix}, N = 4; \quad (14)$$

$$(h_{ij}) = \begin{pmatrix} 1 & 1 & 1 & 1 & 1 & 1 & 1 & 1 \\ 1 & -1 & 1 & -1 & 1 & -1 & 1 & -1 \\ 1 & 1 & -1 & -1 & 1 & 1 & -1 & -1 \\ 1 & -1 & -1 & 1 & 1 & -1 & -1 & 1 \\ 1 & 1 & 1 & 1 & -1 & -1 & -1 & -1 \\ 1 & -1 & 1 & -1 & -1 & 1 & -1 & 1 \\ 1 & 1 & -1 & -1 & -1 & -1 & 1 & 1 \\ 1 & -1 & -1 & 1 & -1 & 1 & 1 & -1 \end{pmatrix}, N = 8. \quad (15)$$

Note that the matrix $(h_{ij})$ for $N=2^p$ where p is an integer is generated from the matrix $(h_{ij})$ for $N=2^{p-1}$ and the matrix $(h_{ij})$ for N=2, i.e., for each matrix element of $(h_{ij})$ for N=2, substitute the matrix $(h_{ij})$ for $N=2^{p-1}$ multiplied by the respective matrix element of $(h_{ij})$ for N=2. This construction technique corresponds to the Sylvester construction [see Sylvester (1867)].

The matrix $H=(h_{ij})$ defined in the preceding discussions are Hadamard matrices of order N. Hadamard matrices are a class of square matrix invented by Silvester [J. J. Sylvester, London Edinburgh and Dublin *Philos. Mag. And J. Sci.*, 34, p 461 (1867)] under the name of anallagmatic pavement, 26 years before Hadamard [J. Hadamard, *Math. Phys.* 12, p 311 (1893)] considered them. Hadamard matrices are common in signal processing and coding applications.

An N×N matrix H $(h_{ij})$ is an Hadamard matrix of order N if the entries of are either ±1 and such that $HH^T=NI$ where $H^T$ is the transpose of H and I is the order N identity matrix. In other words, an N×N matrix with only +1 and −1 as its elements is Hadamard if the inner product of two distinct rows is 0 and the inner product of a row with itself is N, which is equivalent to the condition given by Equation (12).

A Hadamard matrix of order N is a solution to Hadamard's maximum determinant problem, i.e., it has the maximum possible determinant (in absolute value) of any complex matrix with elements $|a_{ij}| \leq 1$ [J. Brenner and L. Cummings, *Amer. Math. Monthly* 79 p. 626 (1972)], namely $N^{N/2}$.

To obtain a matrix $(h_{ij})$ for N different from a value of $2^p$ by integer q, remove any q columns from the Hadamard matrix $H=(h_{ij})$ specified herein for $N=2^p$. For this case, matrix $(h_{ij})$ is a (N−q)×N rectangular matrix and N−q independent conjugated quadratures are measured jointly from 4N measured values of electrical interference signal $\Sigma_{i,k}$ for each spot in or on substrate 60 being imaged. In embodiments of the present invention, arrays of values of electrical interference signal $\Sigma_{i,k}$ are obtained simultaneously with an array of detector pixels to yield an array of N−q independent conjugated quadratures jointly measured for an array of spots in or on a section of substrate 60 being imaged.

The first step in the processing the measured values of $\Sigma_{i,k}$ for the conjugated quadratures specified by j=p, the corresponding $S_{i,p,k}$ term in $\Sigma_{i,k}$ are projected out or extracted from the measured $\Sigma_{i,k}$ to obtain four quantities by using the orthogonal properties of $h_{i,j}$ as expressed by Equation (12). The four quantities are subsequently processed for the conjugated quadratures specified by j=p using the orthogonal properties of $\epsilon_{m,k}$ expressed by Equation (10) such as described in cited U.S. Provisional Patent Applications No. 60/442,858, and No. 60/485,507 and in cited U.S. patent applications filed Jan. 27, 2004 entitled "Apparatus and Method for Joint Measurements of Conjugated Quadratures of Fields of Reflected/Scattered and Transmitted Beams by an Object in Interferometry" and filed Jul. 7, 2004 and entitled "Apparatus And Method For High Speed Scan For Detection And Measurement of Properties of Sub-Wavelength Defects And Artifacts In Semiconductor And Mask Metrology." The procedure is repeated to obtain the other conjugated quadratures.

The advantages of the N-dimensional bi-homodyne and quad-homodyne detection methods are the same as the advantages of the bi-homodyne and quad-homodyne detection methods described in cited U.S. Provisional Patent Application Nos. 60/442,858 and 60/485,507 and in cited U.S. patent application Ser. No. 10/765,368 and U.S. patent application filed Jul. 7, 2004 and entitled "Apparatus And Method For High Speed Scan For Detection And Measurement of Properties of Sub-Wavelength Defects And Artifacts In Semiconductor And Mask Metrology".

The option of using the conjugate adaptive reflective surfaces as optical switches makes it possible to rapidly change the effective value of N from a maximum value to values less than the maximum value for either of the amplitude or phase modulation or permutation modes. For example, if the maximum value of N is 8, the present invention can rapidly change from operating with a value of N=8 to a value of N=2.

The conditions that are used to derive the matrix elements $h_{i,j}$ for the amplitude modulation or permutation embodiment are that the values of $h_{i,j}$ be equal to either 0 or 1 and that the selection of the designs yield the best signal-to-noise ratios. In this case, the values of the matrix elements $h_{i,j}$ are derived for example from a binary simplex code [see M. Harwit and N. J. A. Sloane, *Hadamard Transform Optics* (Academic, New York, 1979)]. Using $s_{ij}$ to denote the matrix elements $h_{i,j}$ for the amplitude modulation or permutation, an example of a set of matrix elements $s_{ij}$ of order 7 is $$(s_{ij}) = \begin{pmatrix} 0 & 0 & 1 & 0 & 1 & 1 & 1 \\ 0 & 1 & 0 & 1 & 1 & 1 & 0 \\ 1 & 0 & 1 & 1 & 1 & 0 & 0 \\ 0 & 1 & 1 & 1 & 0 & 0 & 1 \\ 1 & 1 & 1 & 0 & 0 & 1 & 0 \\ 1 & 1 & 0 & 0 & 1 & 0 & 1 \\ 1 & 0 & 0 & 1 & 0 & 1 & 1 \end{pmatrix}. \quad (16)$$

The phase shift feature of the present invention can be used to obtain differential measurements of properties of the measurement beams reflected/scattered by substrate 60. For an example of N=2 and the introduction of a relative phase shift π between the beams corresponding to the pair of conjugate adaptive reflective surfaces, the measured quantities correspond to a differential measurement, i.e., operation in a dark field mode.

An advantage of the first embodiment of the present invention is that with the generation of the optical interference signal in the intensity of beam 32 comprising beams 32A and 32B, the specifications of the second imaging system 10B are further relaxed as compared when the second imaging system 10B must preserve the phase relationship between reference and measurement beam components.

A first variant of the first embodiment of the present invention comprises the apparatus of the first embodiment and an additional beam conditioning of the measurement beam incident on substrate 60. In the first variant of the first embodiment, the measurement beam is focused to a small spot on substrate 60. The detector may comprise a single pixel detector or a linear array of pixels wherein the linear array of pixels correspond for example to angles of reflection/scattered radiation from substrate 60. The additional beam conditioning may comprise an imaging element 54G and an apodizing filter 54F as shown schematically in FIG. 1g.

Measurement beam 24D is transmitted by imaging element 54G as measurement beam 24E subsequent to transmission by apodizing filter 54F. Measurement beam 24E is a converging beam that is focused to a spot on substrate 60. Apodizing filter 54F may comprise a simple aperture that has a transmission of 100% anywhere within the aperture. In this case, contribution of reflection/scattering by portions of substrate 60 lying outside of the focused spot will contribute to the signal generated by the detector according to the point transfer function of the aperture. For a circular aperture and a uniform beam amplitude across the aperture, the point transfer function is an Airy function $[J_1(x)/x]$ where $J_1$ is a Bessel function of the first kind and order 1. For a square aperture, the transfer function will be the product of two sinc functions, i.e., (sin x/x) (sin y/y).

The wings of the Airy function and the sinc functions can be the source of significant contributions to the signal generated by the detector. The effect of the wings of the transfer functions can be reduced by apodizing the aperture. Consider for example the effect of a triangle apodizing function shown in FIG. 1h. For a square aperture, the resulting transfer function will be the product of two sinc functions squared. The effects of the wings are accordingly significantly reduced. The effects of the wings can be further reduced if desired in an end use application by using for example an apodizing function comprising a triangle function convoluted with a rectangle function.

The apodization of the aperture may be generated by a coating that has a transmission coefficient that depends on the position in the aperture. The apodization of the aperture may also be generated by modifying the cross sectional shape of an aperture.

Figure 1E:
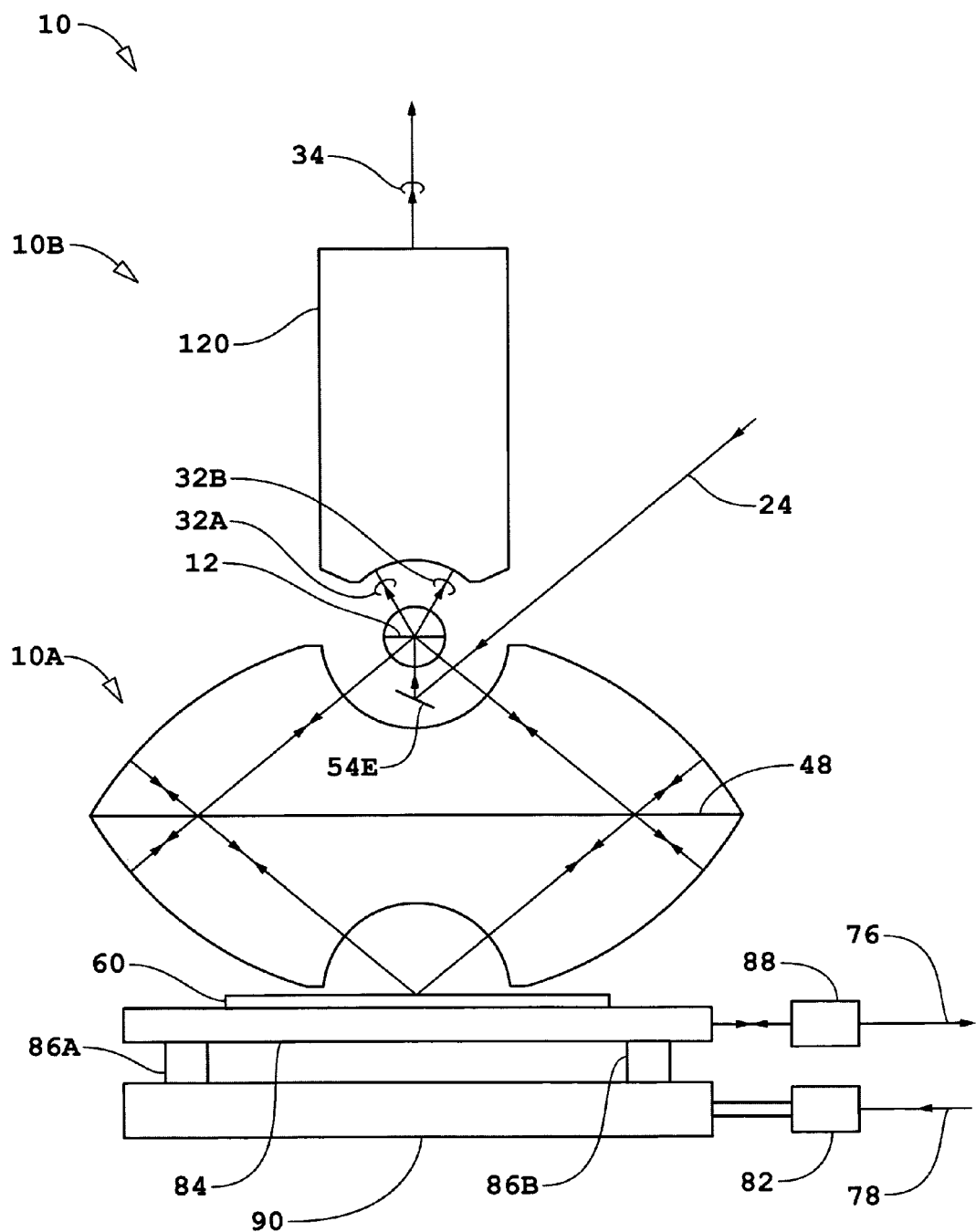
FIG. 1e is a schematic diagram of an interferometric confocal microscope system that uses a catadioptric imaging system.

The second embodiment of the present invention comprising interferometer 10 and catadioptric imaging system 10A is shown diagrammatically in FIG. 1e. The catadioptric imaging system 10A of the second embodiment is the same as the catadioptric imaging system 10A of the first embodiment of the present invention except that thin film fluorescent layer 12 is replaced by a pinhole array beam-splitter 12 shown schematically in FIG. 1f. The pinhole array beam-splitter 12 is used as the beam-splitter for generating the reference and measurement beams and for the function of combining the reference and measurement beam reflected/scattered by substrate 60.

Pinhole array beam-splitter 12 comprises sub-wavelength apertures 62. The size and spacing of the sub-wavelength apertures are a and b, respectively. The description of the operation of an interferometer comprising a pinhole array beam-splitter is the same as the corresponding description given in cited U.S. Provisional Patent Application No. 60/442,982 and U.S. patent application Ser. No. 10/765,229. The remaining description of the second embodiment is the same as corresponding portions of the description given for the first embodiment and variant thereof of the present invention.

Other variants of the first embodiment of the present invention comprise the apparatus of the first embodiment with a modified thin fluorescent layer. In a second variant, a thin fluorescent layer 12B is placed behind an array of pinholes 12A shown schematically in FIG. 1i. The efficiency for detecting beams transmitted by pinhole array 12A can be increased by manufacturing pinhole array 12A with a reflective backside. The size of the spacing c between pinhole array 12A and thin fluorescent layer 12B is selected to optimize the efficiency for detection of beams transmitted by pinhole array 12A without significantly degrading the resolution beyond that required in an end use application.

Figure 1F:
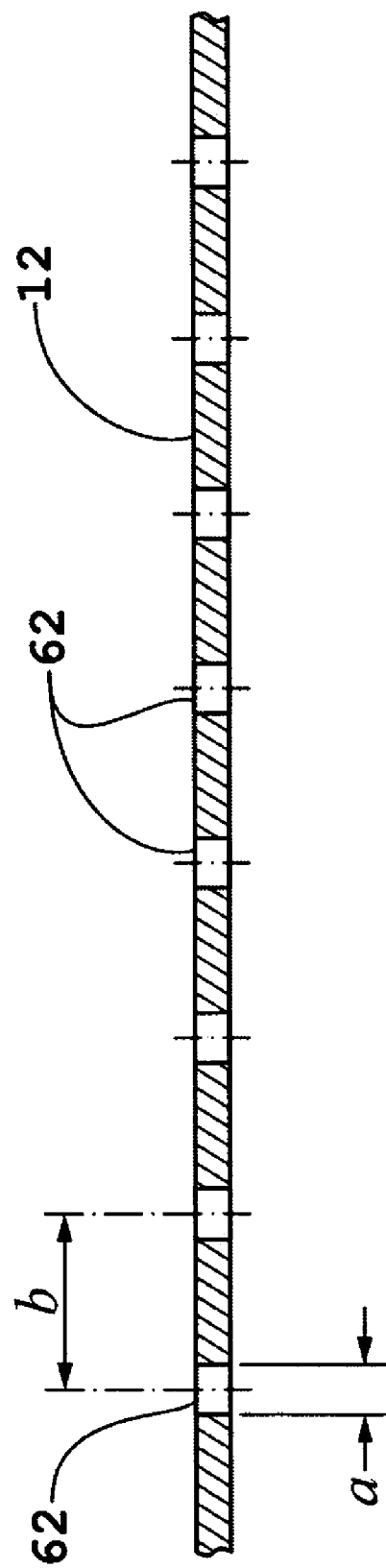
FIG. 1f is a schematic diagram of a pinhole array used in a confocal microscope system.
Figure 1G:
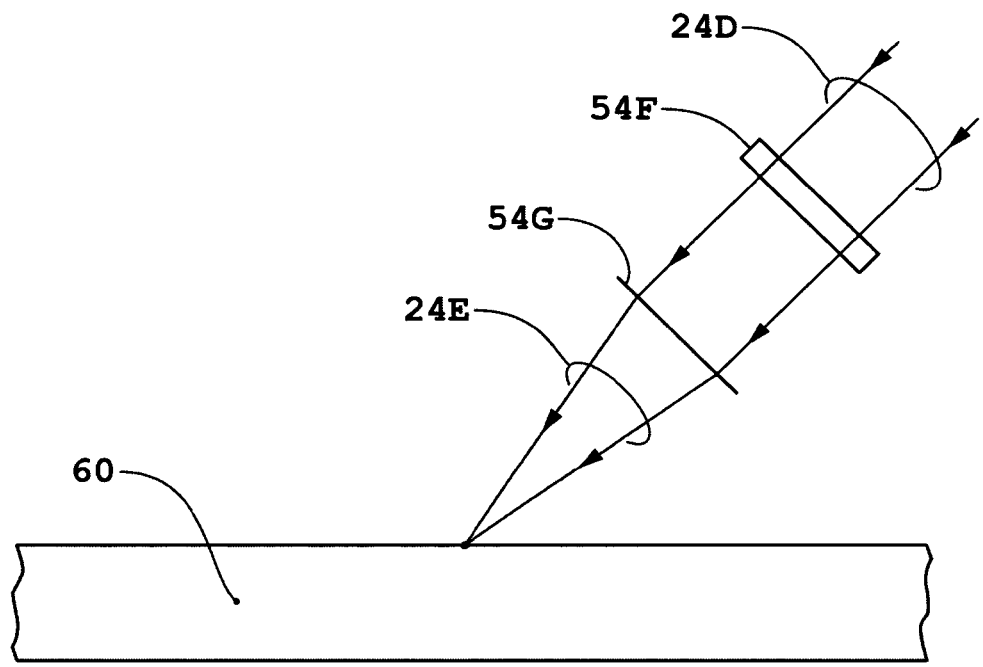
FIG. 1g is a schematic diagram of an imaging element and apodizing filter.
Figure 1H:
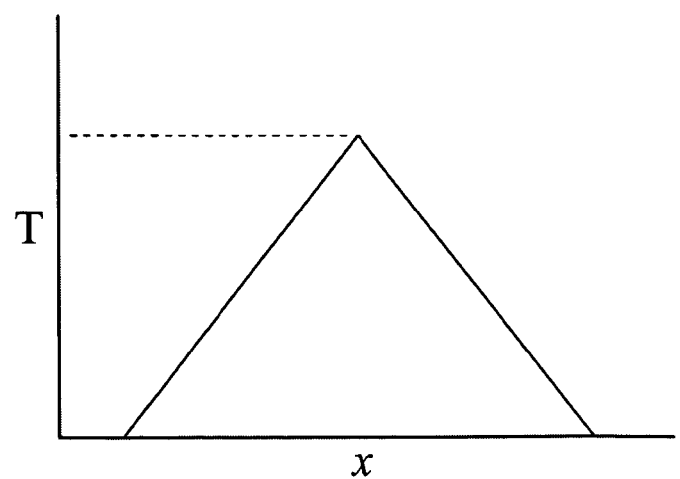
FIG. 1h is a diagram of a triangle apodizing function.
Figure 1I:
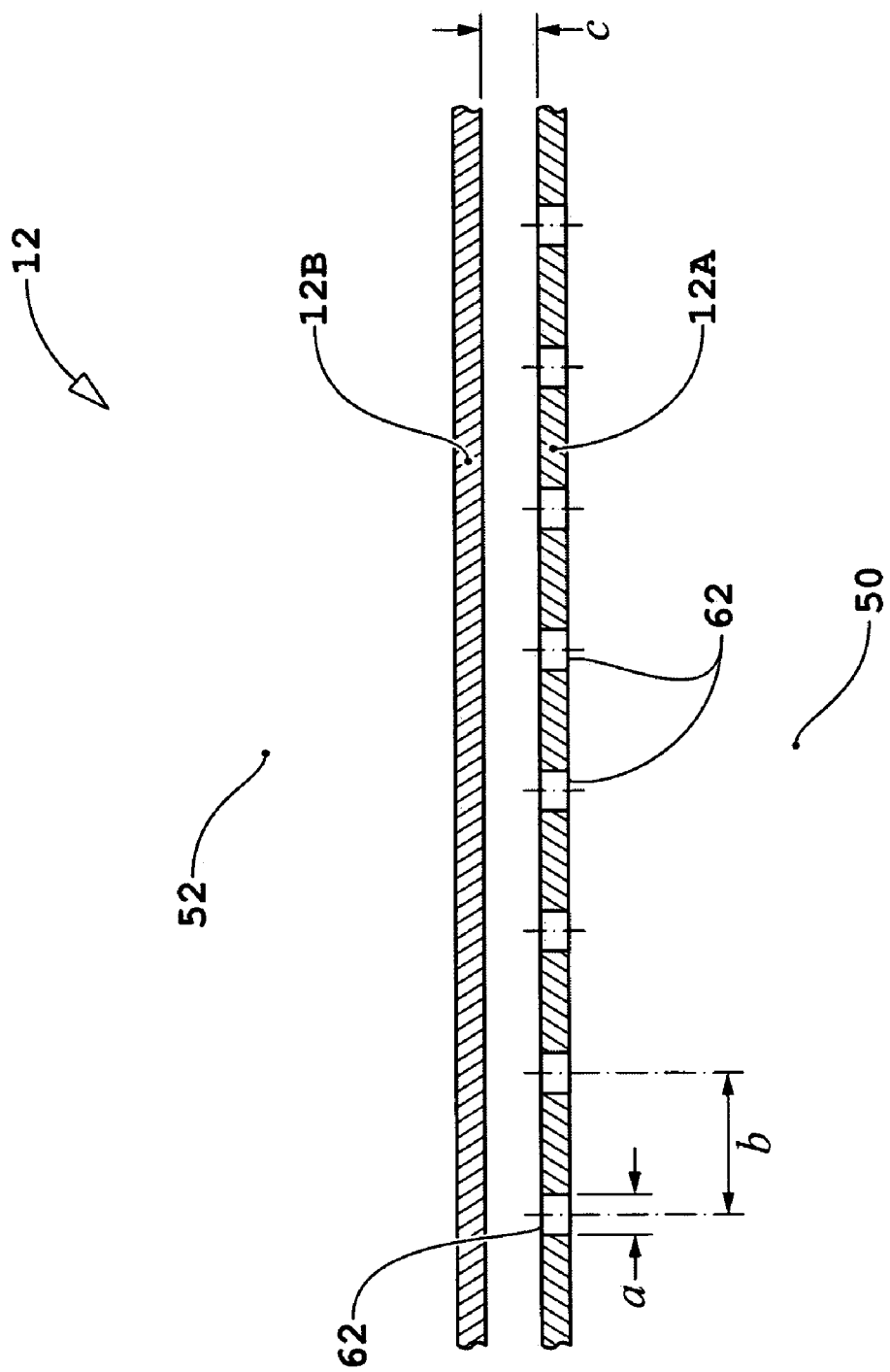
FIG. 1i is a schematic diagram of a thin fluorescent layer placed behind an array of pinholes.
Figure 1J:
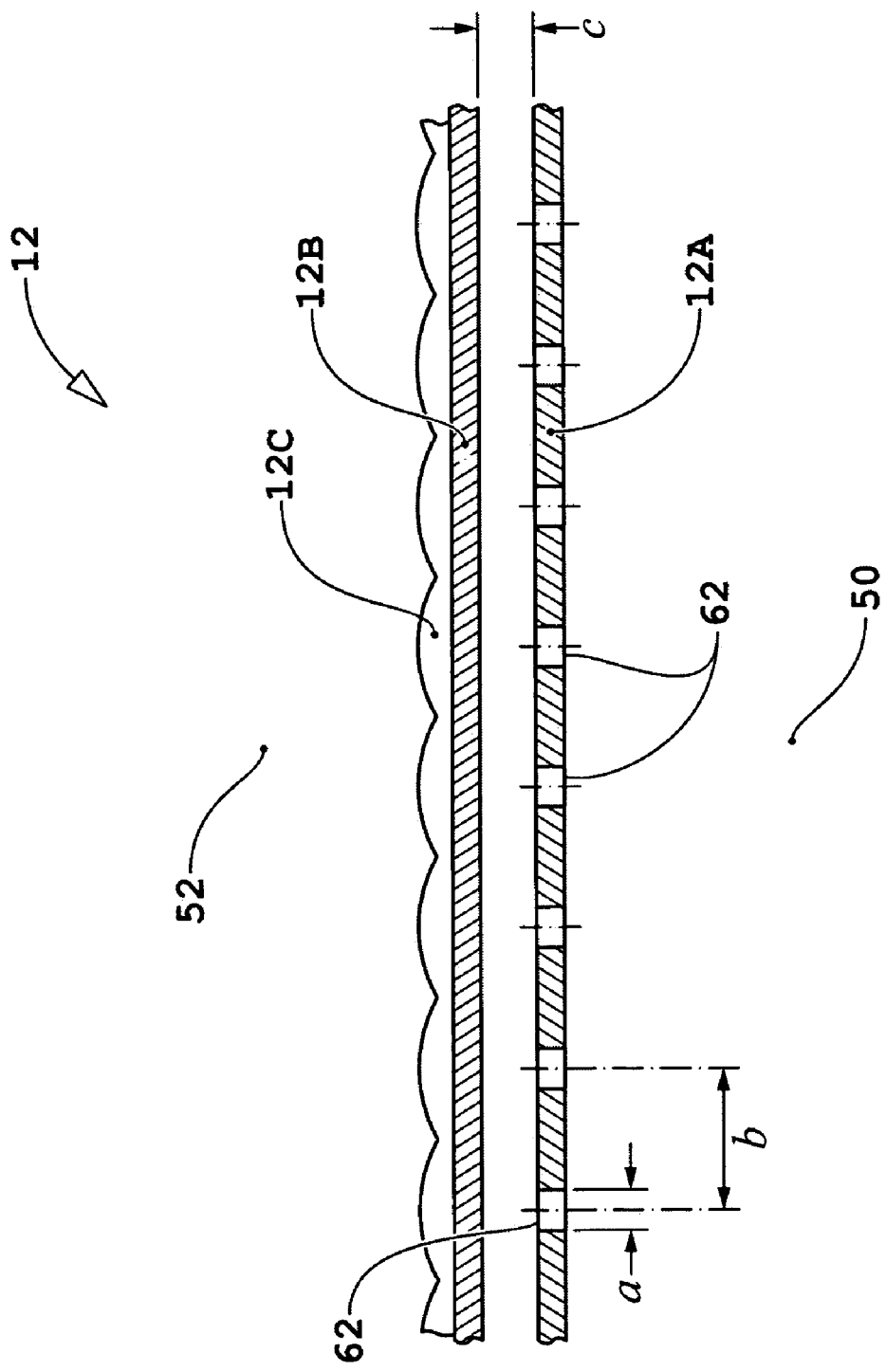
FIG. 1j is a schematic diagram of an array of microlenses placed behind a thin fluorescent layer and array of pinholes.

In a third variant, an array of microlenses 12C is placed behind the thin fluorescent layer 12B and array of pinholes 12A of the second variant such as shown schematically in FIG. 1j. Each microlens of the array of microlenses is aligned with a corresponding different one of the pinholes of the array of pinholes. The addition of the array of microlenses 12C reduces the numerical aperture required for the second imaging system 10B to obtain a given detection efficiency for beams transmitted by pinhole array 12A or increases the detection efficiency for a given numerical aperture of the second imaging system 10B.

In a fourth variant, the thin fluorescent layer 12 is formed of an array of thin fluorescent spots. An example of a pattern of an array of thin fluorescent spots is the pattern of apertures shown in FIG. 1f with apertures 62 replaced by thin fluorescent spots.

The advantage of thin fluorescent spots is that the fluorescent medium itself is used to define the boundary of a region to be used in generating the optical interference signal with a reduced background contribution, i.e., only short wavelength light that is incident on the fluorescent spot can contribute to the generation of the optical interference signal. When an opaque screen with apertures is used to define the light to be subsequently detected, a portion of the light that is transmitted by the opaque region of the screen outside of the apertures will also be detected. This particular source of background contributions is not present when using thin fluorescent spots.

The manufacture of a screen comprising an array of thin fluorescent spots can be done using microlithography techniques. The description of the manufacturing of the screen is the same as the corresponding portion of the description given in the subsequent fifth variant of the first embodiment.

In the fifth variant, the thin fluorescent layer 12 is formed of an array of thin fluorescent spots wherein each spot comprises a cone structure to improve the detection efficiency over that of the fourth variant. An example of a cone structures fluorescent spot is shown schematically as element 1014A in Step 6 of FIG. 1k wherein element 1012A is an absorber, e.g., aluminum or platinum.

Figure 1K:
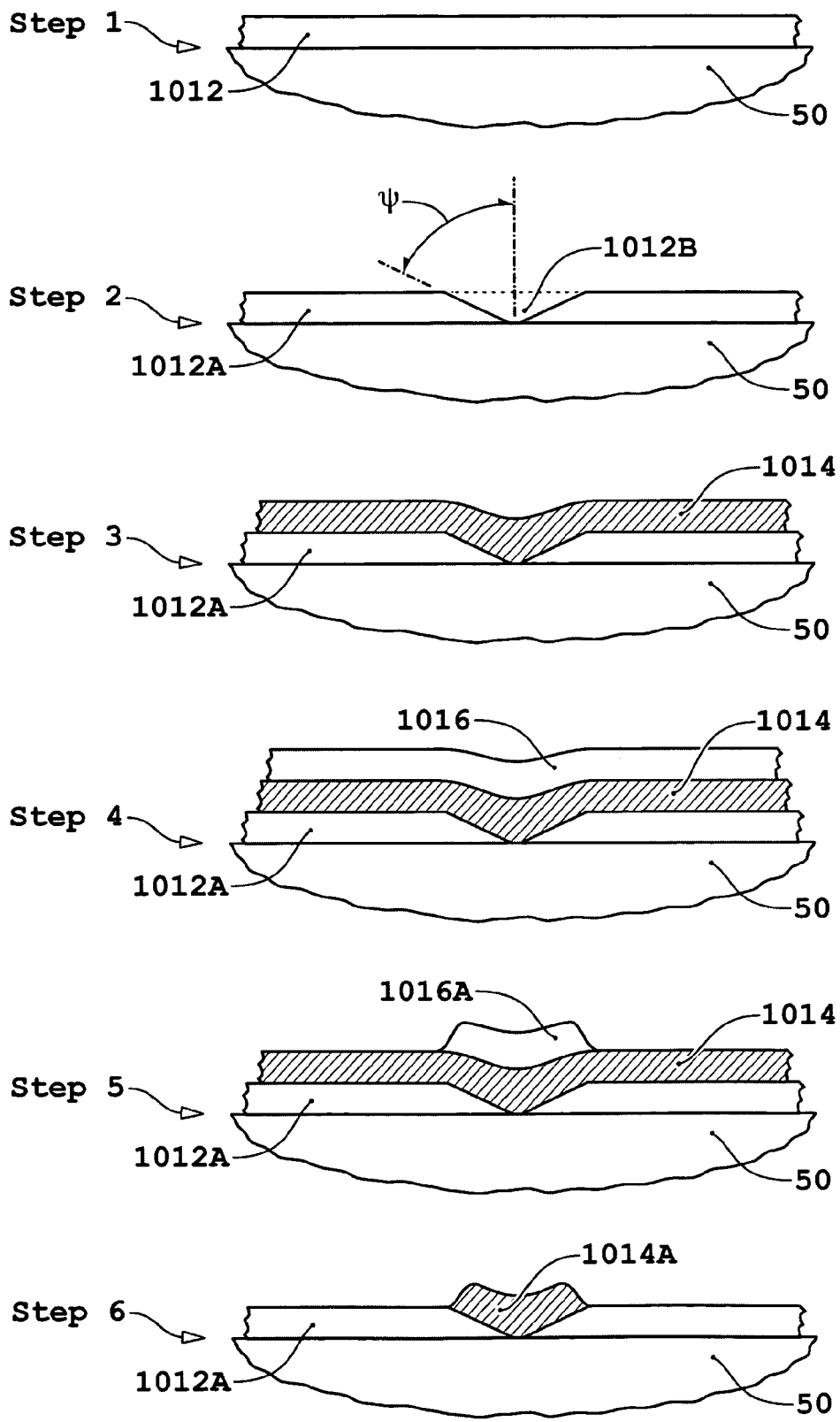
FIG. 1k is a schematic diagram of steps in the manufacture of an array of thin fluorescent spots comprising a cone structure.

The steps used in the manufacture of the array of thin fluorescent spots in the fifth variant are set out in FIG. 1k wherein the thin fluorescent layer 12 is formed of an array of thin fluorescent spots comprising a cone structure. In step 1, the plano surface of plano-convex lens 50 is coated with a thin absorbing layer 1012, e.g., aluminum or platinum. In step 2, thin absorbing layer 1012 is etched to form absorbing layer 1012A with a focused ion beam (FIB) to generate the cone shaped aperture 1012B. A typical half angle $\psi$ of the cone structure (see Step 2 of FIG. 1k) is 60 or 70 degrees.

The half angle $\psi$ is selected such that a portion of the fluorescent light radiated by the fluorescent spot 1014A outside of the numerical aperture of the second imaging system 10B is reflected/scattered into the numerical aperture of the second imaging system 10B so as to effectively increase the detection efficiency for short wavelength light incident on the fluorescent spot 1014A without degrading significantly the resolution of the second imaging system 10B. A typical magnitude of the degrading of the resolution of the second imaging system 10B is of the order of 20%.

Continuing with the description of the Steps of FIG. 1k, absorbing layer 1012A and the array of cone shaped apertures 1012B are coated with a thin fluorescent layer 1014, e.g., lumogen, in Step 3. In Step 4 of FIG. 1k, thin fluorescent layer 1014 is coated with a thin layer of a negative photoresist 1016. In Step 5, photoresist layer 1016 is patterned by either contact printing or by a lithography tool, developed, and the unexposed portion of layer 1016 dissolved leaving photoresist spots 1016A. In Step 6, the substrate comprising photoresist spots 1016A and thin fluorescent layer 1014 are etched so as to remove the thin fluorescent not covered by the photoresist spots 1016A leaving a thin fluorescent spots 1014A caped with photoresist spots. The photoresist caps may be removed as shown in Step 6 of FIG. 1k. The substrate comprising the array of thin fluorescent spots 1014A with or without the photoresist spots (the photoresist spots are removed if not transparent at the wavelength of the radiation emitted by the fluorescent spots 1014A) is bonded to convex lens 52.

Field of View: the longitudinal separation between the sagittal and tangential surfaces $\Delta z$ is given by the formula $$\Delta z = 2 \frac{\rho^2}{r_0} \qquad (17)$$

where $\rho$ is the radius of the field of view and $r_0$ is the radius of the respective catoptric reflective surface of imaging system 10A. Defining the field of view as that radius $\rho$ such that the longitudinal separation $\Delta z$ is equal to the depth of focus, we have $$\rho = \left(\frac{r_0 \lambda}{2}\right)^{1/2} \frac{1}{NA} \qquad (18)$$

where NA is the numerical aperture of catoptric imaging system 10A.

The advantage of thin fluorescent spots configured as cones is that the fluorescent medium itself is used to define the boundary of a region to be used in generating the optical interference signal with improved detection efficiency and a reduced background contribution, i.e., only short wavelength light that is incident on the fluorescent spot can contribute to the generation of the optical interference signal. When an opaque screen with apertures is used to define the light to be subsequently detected, a portion of the light that is transmitted by the opaque region of the screen outside of the apertures will also be detected. This particular source of background contributions is not present when using thin fluorescent spots configured as cones.

Figure 2A:
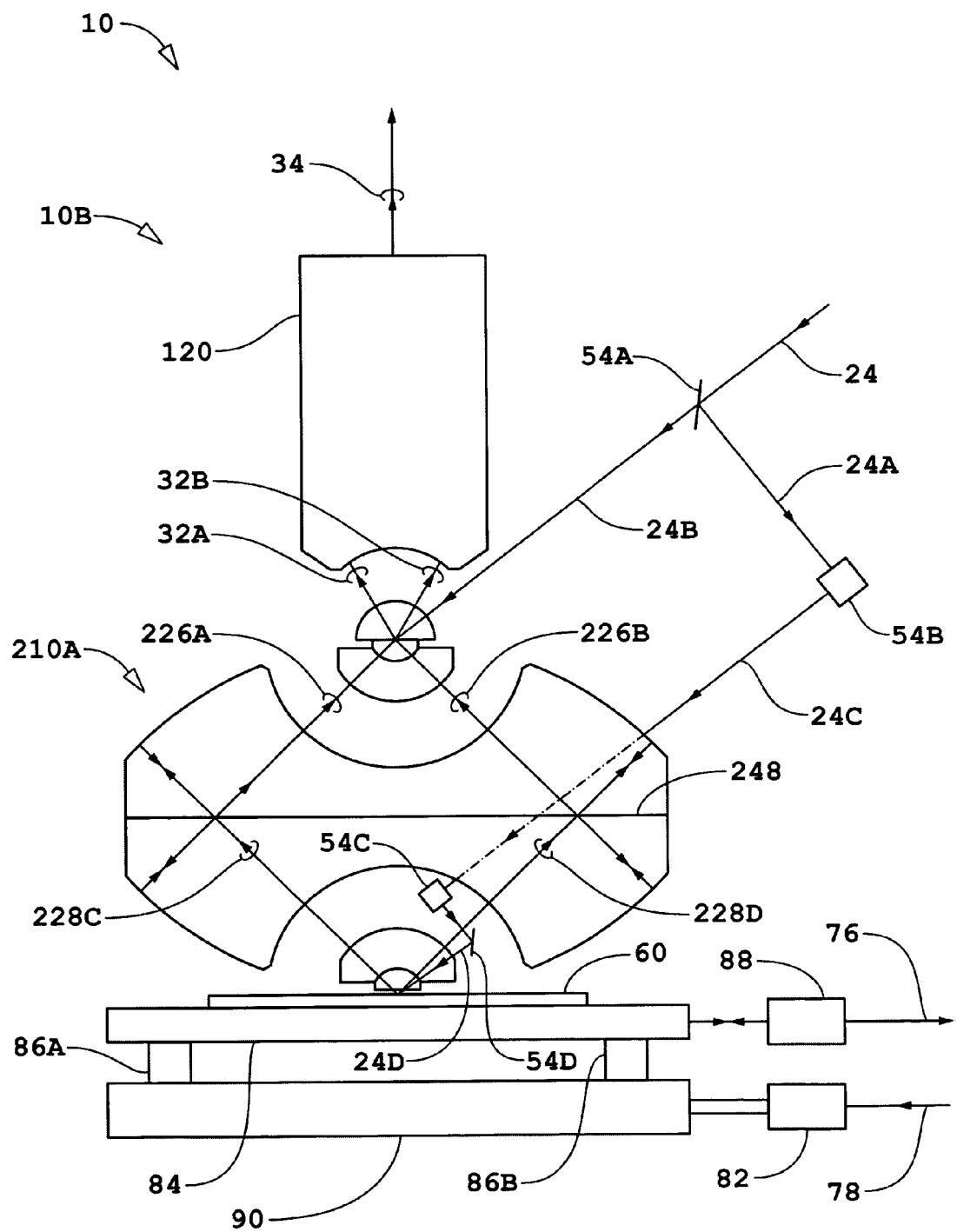
FIG. 2a is a schematic diagram of an interferometric non-confocal microscope system that uses a catadioptric imaging system.

The third embodiment of interferometer 10 is shown diagrammatically in FIG. 2a. The description of source 18, beam-conditioner 22, detector 70, an electronic processor and controller 80, and substrate 60 is the same as the corresponding description given for elements of the first embodiment that have the same element numbers. Interferometer 10 of the third embodiment is the same as interferometer 10 of the first embodiment of the present invention except that catadioptric imaging system 10A of the first embodiment replaced by catadioptric imaging system 210A (see FIG. 2a). Catadioptric imaging system 210A is the same as catadioptric imaging system 10A except that there are two compensating convex refractive surfaces in system 210A instead of a single compensating convex refractive element 50 in system 10A.

Figure 2B:
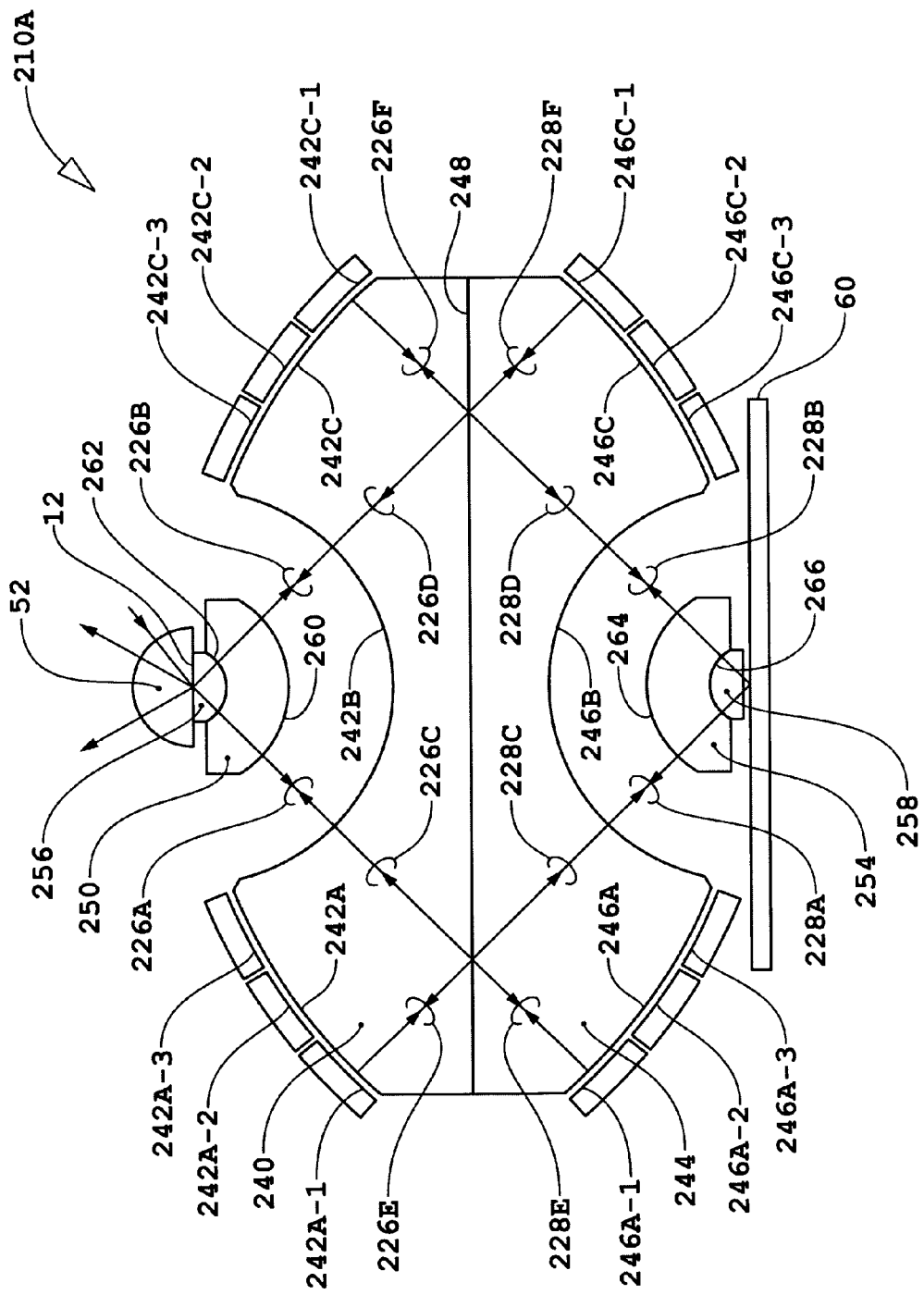
FIG. 2b is a diagram of a catadioptric imaging system comprising adaptive catoptric reflecting surfaces.

Catadioptric imaging system 210A is shown schematically in FIG. 2b. Elements of catadioptric imaging system 210A shown in FIG. 2b comprise two different media in order to generate an achromatic anastigmat. Catadioptric imaging system 210A comprises catadioptric elements 240 and 244, beam-splitter 248, concentric lenses 250 and 254, and plano convex lenses 256 and 258. Surfaces 242A and 242C comprise a first single convex spherical surface and surfaces 246A and 246C comprise a second single convex spherical surface with nominally the same radii of curvature and the respective centers of curvature of the first and second single convex spherical surfaces are conjugate points with respect to beam-splitter 248. Surfaces 242B and 246B are concave spherical surfaces with nominally the same radii of curvature. The centers of curvature of surfaces 242B and 246B are the same as the centers of curvature of the second and first single convex spherical surfaces, respectively.

The centers of curvature of the surfaces of concentric lens 250 and plano convex lens 256 are nominally the same as the center of curvature of surfaces 242B and the second single convex spherical surface. The centers of curvature of the surfaces of concentric lens 254 and plano convex lens 258 are nominally the same as the center of curvature of surfaces 246B and the first single convex spherical surface. The radii of curvature of surfaces 260 and 264 are nominally the same and the radii of curvature of surfaces 262 and 266 are nominally the same. There may be a small gap between the convex surface and corresponding concave surface of lenses 256 and 250, respectively, and there may be a corresponding small gap between the convex surface and corresponding concave surface of lenses 258 and 254, respectively.

Figure 2C:
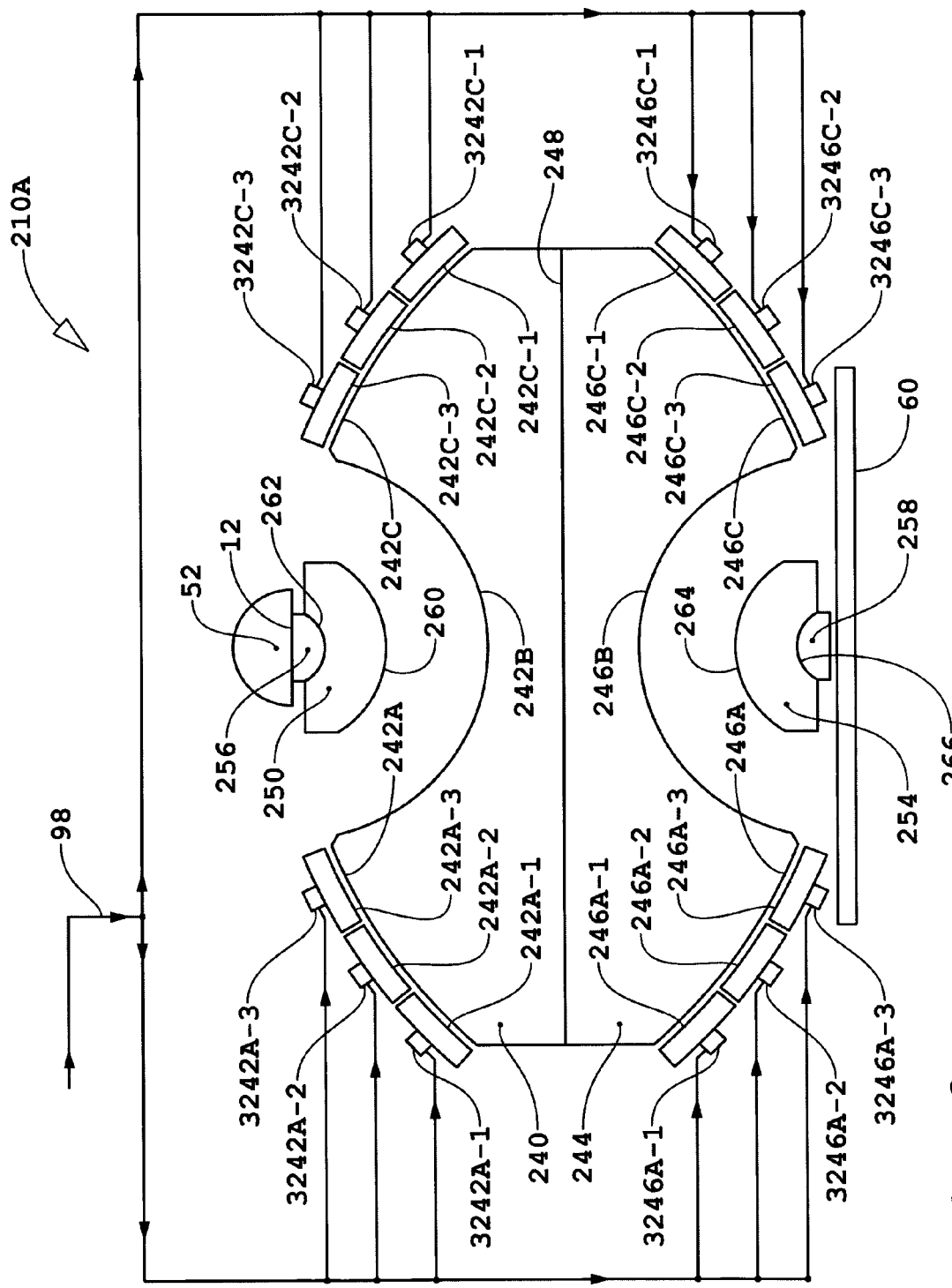
FIG. 2c is a diagram of a catadioptric imaging system comprising adaptive catoptric reflecting surfaces attached to displacement transducers.

Associated with the convex refractive surfaces 242A, 242C, 246A, and 246C are adaptive reflective surfaces 242A-1, 242A-2, 242A-3, 242C-1, 242C-2, 242C-3, 246A-1, 246A-2, 246A-3, 246C-1, 246C-2, and 246C-3. The adaptive reflective surfaces 242A-1, 242A-2, 242A-3, 242C-1, 242C-2, 242C-3, 246A-1, 246A-2, 246A-3, 246C-1, 246C-2, and 246C-3 are shown schematically in FIG. 2b and the adaptive reflective surfaces with associated transducers 3242A-1, 3242A-2, 3242A-3, 3242C-1, 3242C-2, 3242C-3, 3246A-1, 3246A-2, 3246A-3, 3246C-1, 3246C-2, and 3246C-3 are shown schematically in FIG. 2c.

The description of the operation and different modes of operation of the third embodiment of the present invention with respect to the adaptive reflective surfaces is the same as corresponding portions of the description given for the operation and for the different modes of operation of adaptive reflective surfaces in the first embodiment and variant thereof of the present invention.

Figure 2D:
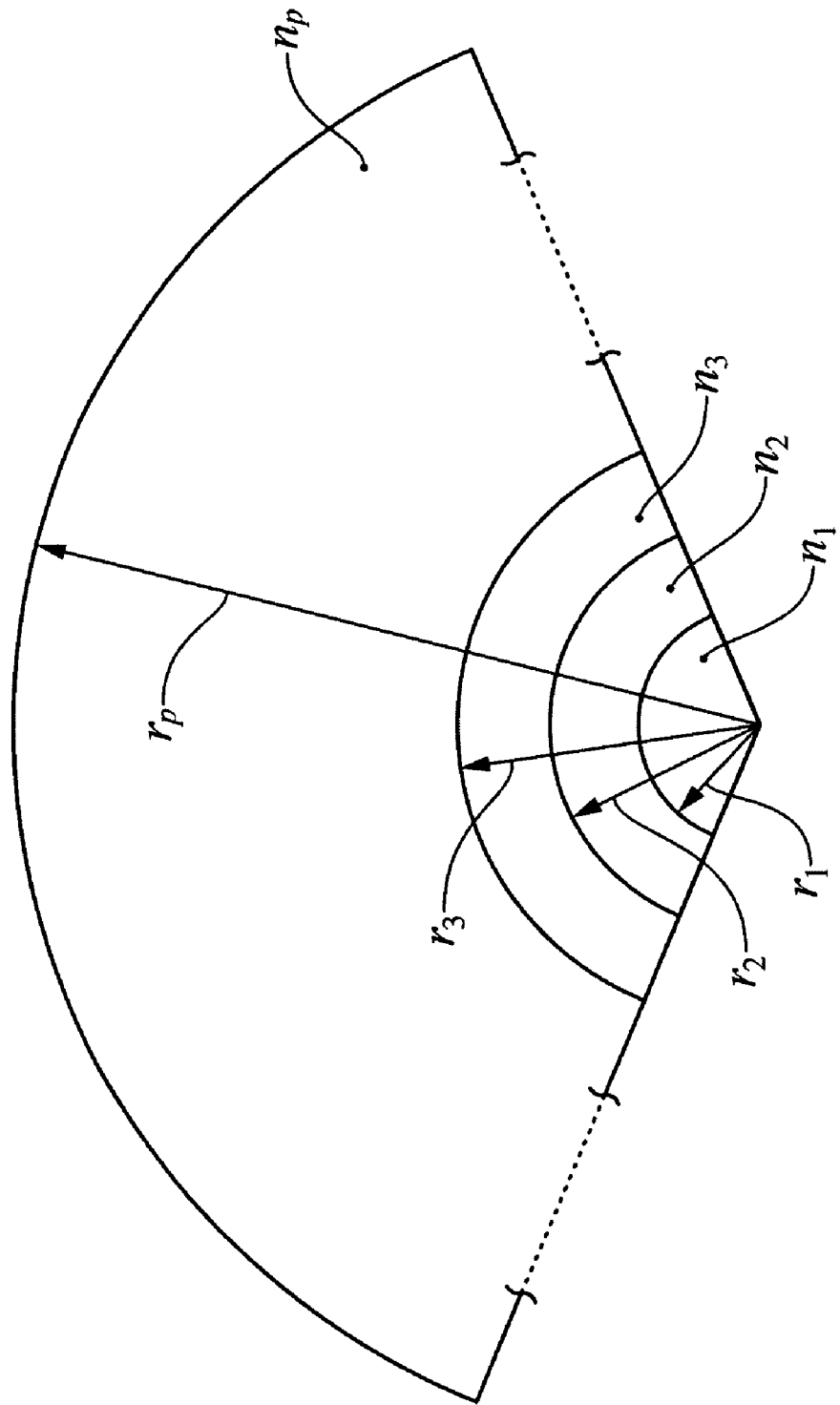
FIG. 2d is a diagram showing surfaces and corresponding radii of a catadioptric imaging system.

The sagittal field of catadioptric imaging system 210A is a flat field and the tangential field is also a flat field for a certain object field when the Petzval sum is zero, i.e., $$2\sum_{j=1}^{p-1} \left( \frac{1}{n_j} - \frac{1}{n_{j+1}} \right) \frac{1}{r_j} + \frac{1}{n_p} \frac{2}{r_p} = 0 \quad (19)$$

where $r_j$ is the radius of curvature of surface j, $r_p$ is the radius of curvature of the mirror surface, and $n_j$ is the index of refraction of the media located on the beam incidence side of surface j such as shown diagrammatically in FIG. 2d. The condition for the generation of an achromatic anastigmat at wavelength $\lambda_c$ is accordingly given by the equation $$\partial \frac{\left[ 2\sum_{j=1}^{p-1} \left( \frac{1}{n_j} - \frac{1}{n_{j+1}} \right) \frac{1}{r_j} + \frac{1}{n_p} \frac{2}{r_p} \right]}{\partial \lambda} = 0. \quad (20)$$

Two considerations in the selection of the radii of curvature of surfaces 242B and 246B and surfaces 262 and 266 are the area of the system pupil function of the imaging system 210A and the size of the object field that can be effectively used with respect to image quality. The first two considerations place competing demands on the selection of the radii of curvature of surfaces 242B and 246B and surfaces 262 and 266. Third and fourth considerations are with respect to the conditions set out in Equations (19) and (20). A fifth consideration in the selection of the media of the lenses of imaging system 210A is the transmission properties of the media for the range of wavelengths to be used in an end use application.

For an example of an achromatic anastigmat design for deep UV operation, the media of elements 240, 244, 256, and 258 is selected as $CaF_2$ and the media of concentric lenses 252 and 254 is selected as a UV grade fused silica. Other parameters of the example achromatic anastigmat design such as the radii of curvature of surfaces are listed in Table 1 for $\lambda_c=250$ nm. With this choice of media, the operation range is down to 170 nm. For the achromatic anastigmat design parameters listed in Table 2, the contribution of geometric ray tracing effects is $\leq 40$ nm for an object field of 1.5 mm in diameter and a numerical aperture NA=0.970 in the object space just outside of the plane surface of plano convex lens 258.

Figure 2E:
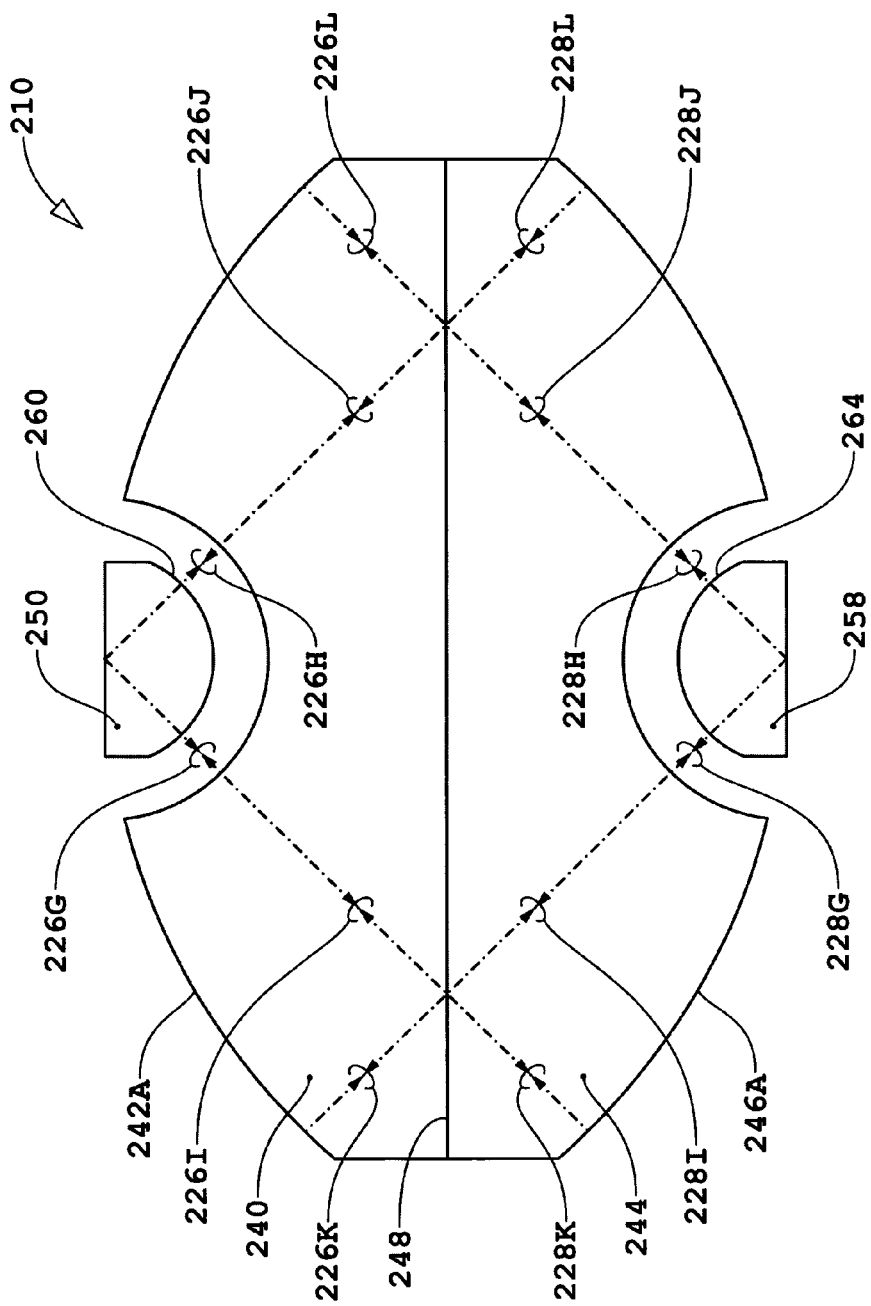
FIG. 2e is a diagram of a catadioptric imaging system.

A variant of catadioptric imaging system 210A is shown in FIG. 2e wherein catadioptric imaging system 210A is an anastigmat that is not achromatic. The media of elements 240 and 244 may comprise $CaF_2$, $BaF_2$, or $SrF_2$ for work down to 140 nm and UV grade fused silica for operation to 180 nm. The respective radii of the curvature for anastigmat design at $\lambda=250$ nm using $CaF_2$ are listed in Table 2. For anastigmat design listed in Table 3, the contribution of geometric ray tracing effects is $\leq 40$ nm for an object field of 1.5 mm and a numerical aperture NA=0.970 in the object space just outside of the plane surface of plano convex lens 258.

The respective radii of curvature for anastigmat design at λ=250 nm using fused silica are listed in Table 4. For the anastigmat design listed in Table 4, the contribution of geometric ray tracing effects is ≤40 nm for an object field of 1.5

TABLE 2

Achromatic Anastigmat Design for $\lambda_v$ = 250 nm

| Media | j | $n_j$ | $r_j$ (mm) |
|---|---|---|---|
| CaF$_2$ | 1 | 1.467297 | 3.600 |
| Fused Silica | 2 | 1.507446 | 9.256 |
| Vacuum | 3 | 1 | 18.000 |
| CaF$_2$ | 4 | 1.467297 | 50.000 |

TABLE 3

Anastigmat Design for λ = 250 nm

| Media | j | $n_j$ | $r_j$ (mm) |
|---|---|---|---|
| CaF$_2$ | 1 | 1.467297 | 7.950 |
| Air | 2 | 1 | 12.000 |
| CaF$_2$ | 3 | 1.467297 | 50.000 |

TABLE 4

Anastigmat Design for λ = 250 nm

| Media | j | $n_j$ | $r_j$ (mm) |
|---|---|---|---|
| Fused Silica | 1 | 1.507446 | 8.147 |
| Air | 2 | 1 | 12.000 |
| Fused Silica | 3 | 1.507446 | 50.000 | mm and a numerical aperture NA=0.970 in the object space just outside of the plane surface of piano convex lens 258.

Another form of catadioptric imaging system that may be used for catadioptric and catoptric imaging system 10 is the catadioptric imaging system such as described in commonly owned U.S. Provisional Patent Application No. 60/460,129 entitled "Apparatus and Method for Measurement of Fields of Forward Scattered/Reflected and Backscattered Beams by an Object in Interferometry" and U.S. patent application Ser. No. 10/816,172 wherein both are by Henry A. Hill and the contents of which are herein incorporated in their entirety by reference.

Figure 2F:
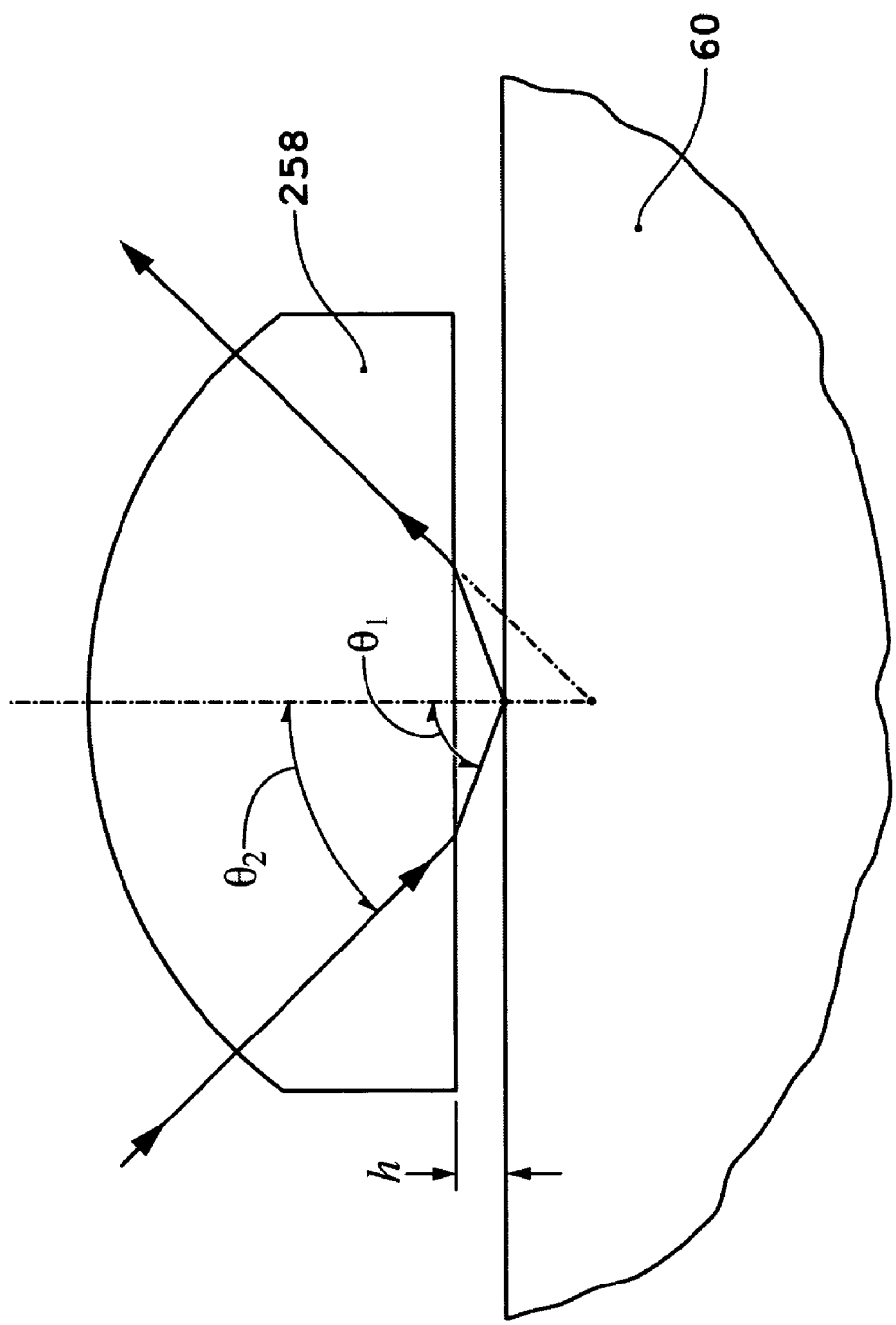
FIG. 2f is a schematic diagram of a section of a catadioptric imaging system located near a measurement object and configured to image the surface section of the measurement object.
Figure 2G:
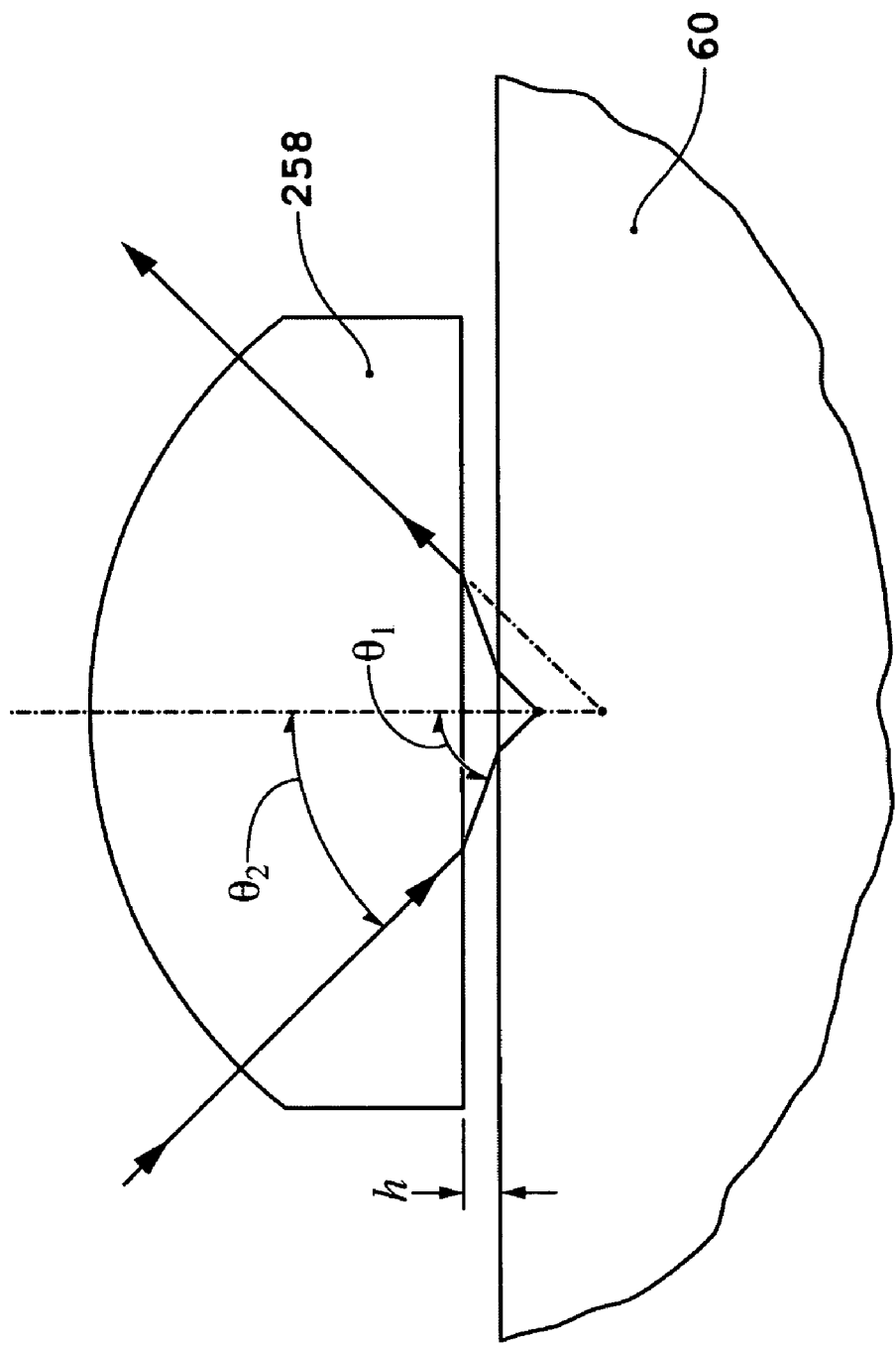
FIG. 2g is a schematic diagram of a section of a catadioptric imaging system located near a measurement object and configured to image an interior section of the measurement object.

The location of the object plane of catadioptric imaging system 210A shown diagrammatically in FIG. 2f is outside of plano convex lens 258 and on the surface of substrate 60. The separation of the plane surface of piano convex lens 258 and the surface of substrate 60 is h. The object plane of catadioptric imaging system 210A may also be located in the interior of substrate 60 which is shown diagrammatically in FIG. 2g. The spherical aberrations introduced by transmission through plane surfaces shown in FIGS. 2f and 2g are compensated in the third embodiment through the use of the conjugate adaptive reflective surfaces such as described in the first embodiment of the present invention.

The remaining description of the third embodiment of the present invention is the same as the corresponding portions of the descriptions of the first embodiment and variant thereof and second embodiment of the present invention and of the catadioptric imaging systems given in cited U.S. Provisional Patent Applications No. 60/485,507 and No. 60/485,255 and U.S. Patent Applications 60/485,507 filed Jul. 7, 2004 and entitled "Apparatus and Method for High Speed Scan for Subwavelength Defects in Semiconductor Metrology" and 60/485,255 filed Jul. 7, 2004 entitled "Apparatus and Method for Ellipsometric Measurements with High Spatial Resolution."

The mode of operation wherein the object plane is located in the interior of substrate 60 can be used to measure properties of unfilled and filled trenches and vias. The high speed vertical scanning mode of the present invention makes it possible to measure the properties of the trenches and vias as a function of depth into substrate 60. The interior mode of operation may also be beneficially used in scanning for defects in trenches and vias that are either unfilled or filled with either a transparent dielectric or a conductor.

The location of the object plane of catadioptric imaging system 210A may also be on the plane surface of plano convex lens 258. In this case, the measurement beam can be arranged to probe substrate 60 as an evanescent field when h is of the order of λ/4. The third embodiment can change rapidly from using the evanescent field as a probe beam to using the non-evanescent fields as a probe beam by use of the high speed vertical scan feature of the present invention.

The fourth embodiment of the present invention comprises interferometer 10 and catadioptric imaging system 210A of the third embodiment except that thin film fluorescent layer 12 is replaced by a pinhole array beam-splitter 12 the same as in the second embodiment shown schematically in FIG. 1f. Pinhole array beam-splitter 12 is used as the beam-splitter for generating the reference and measurement beams and for the function of combining the reference and measurement beam reflected/scattered by substrate 60. The remaining description of the fourth embodiment is the same as corresponding portions of the second and third embodiments of the present invention.

A general description of embodiments of the present invention shown diagrammatically in FIG. 3a will next be given for interferometer systems operating in a transmission mode. Much of the description given for the interferometer systems operating in the reflection mode is the same as the description for the interferometer systems operating in the transmission mode.

The embodiments of the present invention configured for operation in the transmission mode use either N-dimensional bi- or quad-homodyne detection methods for fields transmitted by substrate 60. When input beam 24 comprises coextensive reference and measurement beams, first and second portions of input beam 24 are reflected and transmitted, respectively, as measurement beam 324A and reference beam 324B, respectively, by non-polarizing beam-splitter 354A. When input beam 24 comprises non-coextensive reference and measurement beams, element 354A functions as mirror to reflect the measurement beam component of beam 24 as beam 324A leaving the reference beam component beam 24 as reference beam 324A. The description of input beam 24 is the same as the description given for the input beam 24 used in the embodiments of the present invention configured for operation in the reflection mode.

Figure 3A:
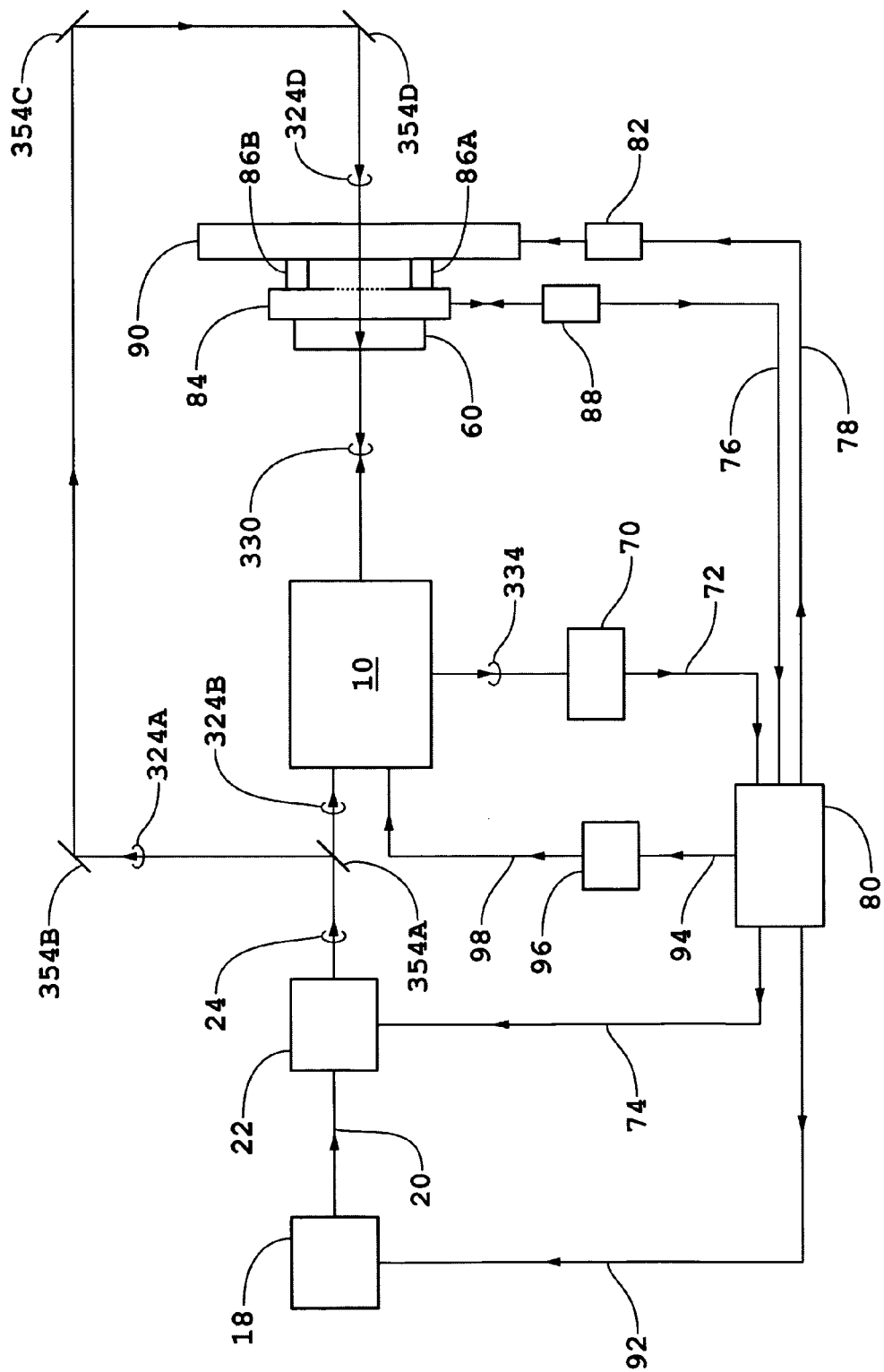
FIG. 3a is a schematic diagram of an interferometric system operating in a transmitting mode.

Interferometer 10 of FIG. 3a comprises a catadioptric imaging system that may have no adaptive reflecting surfaces or may have one or more adaptive reflecting surfaces. For the catadioptric imaging systems that comprise one or more adaptive reflecting surfaces, the shapes of the one or more adaptive reflecting surfaces are controlled by a signal 98 from servo controller 96 according to error signal 94 from electronic processor and controller 80. The descriptions of signal 98, servo controller 96, and electronic processor and controller 80 is the same as corresponding portions of the description given for embodiments of the present invention configured for operation in the reflection mode.

A portion of measurement beam 324A is incident on the backside of substrate 60 as measurement beam 324D after reflection by mirror systems 354B, 354C, and 354D. Substrate 60 may comprise a reticle mask with or without a pellicle protective interface. If a pellicle protective interface is part of substrate 60, interferometer 10 may need to be configured for a large working distance, e.g., 6 mm. The working distance of interferometer 10 can be increased for example by removing a horizontal portion of the catadioptric element adjacent to substrate 60 at the expense of increasing the size of the central obstruction presented to beams reflected/scattered or transmitted by the catadioptric imaging system. A portion of measurement beam 324D incident on the backside of substrate 60 is transmitted as transmitted measurement beam 328. Measurement beam 328 and reference beam 324B are combined in interferometer 10 and exit as output beam 332. Output beam 332 is detected by detector 70 as electrical interference signal 72.

Figure 3B:
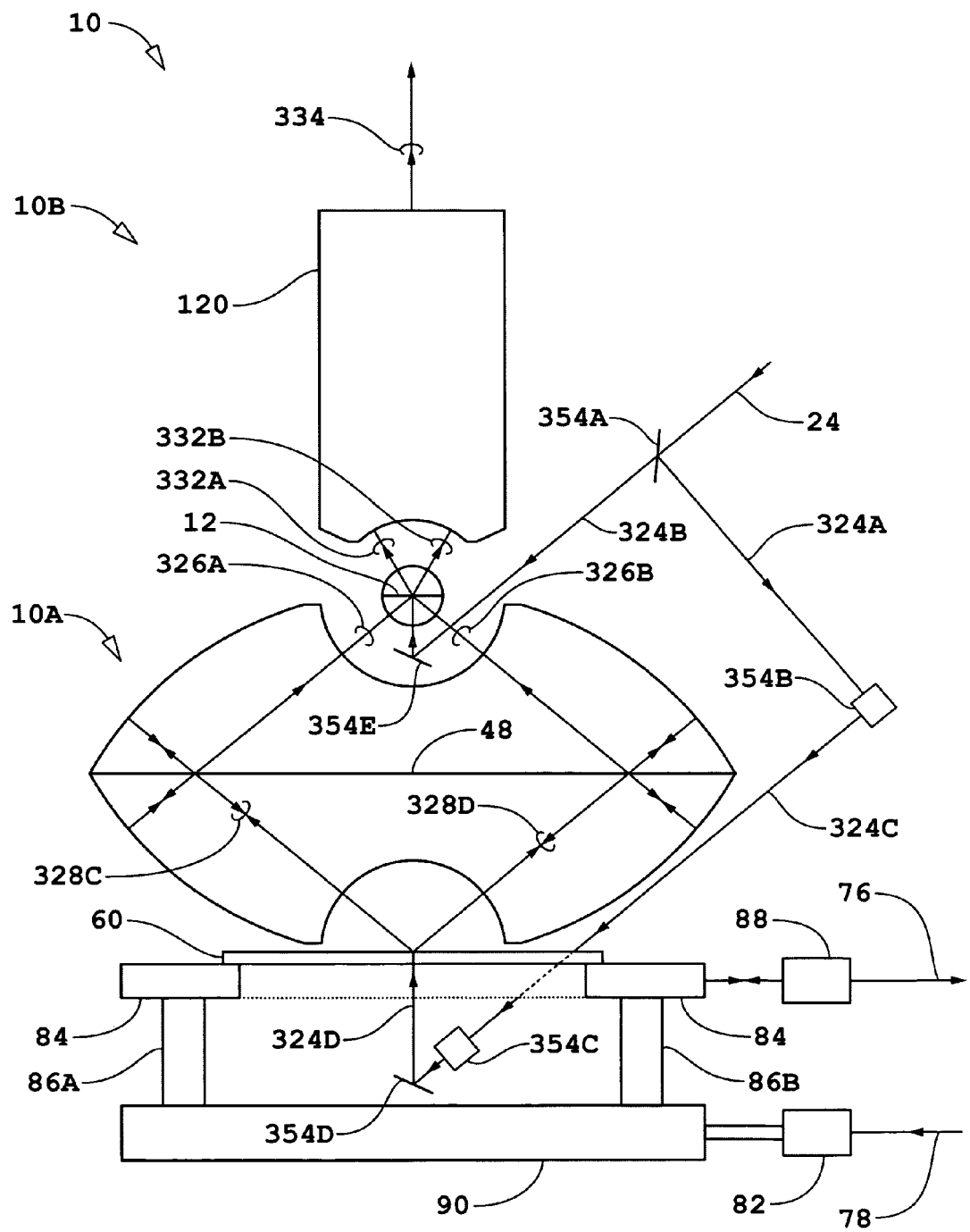
FIG. 3b is a schematic diagram of an interferometric non-confocal microscope system that uses a catadioptric imaging system.

An interferometer 10 of the fifth embodiment of the present invention is shown schematically in FIG. 3b. Interferometer 10 of the fifth embodiment comprises a first imaging system generally indicated as numeral 10A, thin fluorescent layer 12, and a second imaging system generally indicated as numeral 10B. The description of the first and second imaging systems 10A and 10B, respectively, is the same as the description of the first and second imaging systems 10A and 10B of the first embodiment of the present invention.

Referring to FIG. 3b, mirror system 354B redirects and displaces measurement beam 324A such that measurement beam 324C is propagating in a plane displaced out of the plane of FIG. 3b. Mirror system 354C displaces measurement beam 324C such that the transmitted measurement beam subsequently reflected by mirror 354D propagates in the plane of FIG. 3b.

The remaining description of the fifth embodiment of the present invention is the same as corresponding descriptions given for the first four embodiments of the present invention and corresponding descriptions given for embodiments given in cited U.S. Pat. No. 6,552,852 and Ser. No. 10/366,651; U.S. Provisional Patent Applications No. 60/447,254, No. 60/448,360, No. 60/448,250, No. 60/442,982, No. 60/459,425, No. 60/485,255, filed Jul. 7, 2003 and entitled "Apparatus and Method for High Speed Scan for Subwavelength Defects in Semiconductor Metrology," and filed Sep. 10, 2003 entitled "Catoptric and Catadioptric Imaging Systems With Adaptive Catoptric Surfaces;" and U.S. patent applications Ser. No. 10/778,371 entitled "Transverse Differential Interferometric Confocal Microscopy," Ser. No. 10/782,057 entitled "Longitudinal Differential Interferometric Confocal Microscopy," No. 10/782,058 entitled "Thin Film Metrology Using Interferometric Confocal Microscopy," Ser. No. 10/765,229 entitled "Interferometric Confocal Microscopy Incorporating Pinhole Array Beam-Splitter," and Ser. No. 10/816,180 entitled "Apparatus and Method for Joint Measurement Of Fields Of Orthogonally Polarized Beams Scattered/Reflected By An Object In Interferometry;" and U.S. Patent Application 60/485,255 filed Jul. 7, 2004 entitled "Apparatus and Method for Ellipsometric Measurements with High Spatial Resolution."

Catoptric and Catadioptric Imaging Systems Comprising a Thin Beam-Splitter

The remaining embodiments of the present invention comprise catoptric and catadioptric imaging systems for catadioptric imaging system 10A of FIGS. 1a and 3a and for catadioptric imaging system 210A of FIG. 2b that use a thin beam-splitter. The thin beam-splitter may be a pellicle beam-splitter comprising a stack of one or more thin layers of dielectrics and conductors, e.g., aluminum, may comprise a thin reflective layer with an array of transmitting apertures wherein the size of the apertures is larger than the wavelength of an optical beam being focused by the imaging system, or may comprise an array or grid of conducting wires.

In comparison to certain catoptric and catadioptric imaging systems that comprise a non-thin beam-splitter, the use of a thin beam-splitter reduces the magnitude of off-axis aberrations and also reduces the optical path length in a refractive medium which is particularly important when working in the IR, VUV, or EUV. For a catoptric imaging system comprising a pellicle or aperture array beam-splitter, the EUV range includes wavelengths shorter than 100 nm and for a catadioptric imaging system comprising a pellicle or aperture array beam-splitter, the VUV range includes wavelengths down to approximately 120 nm.

Figure 4A:
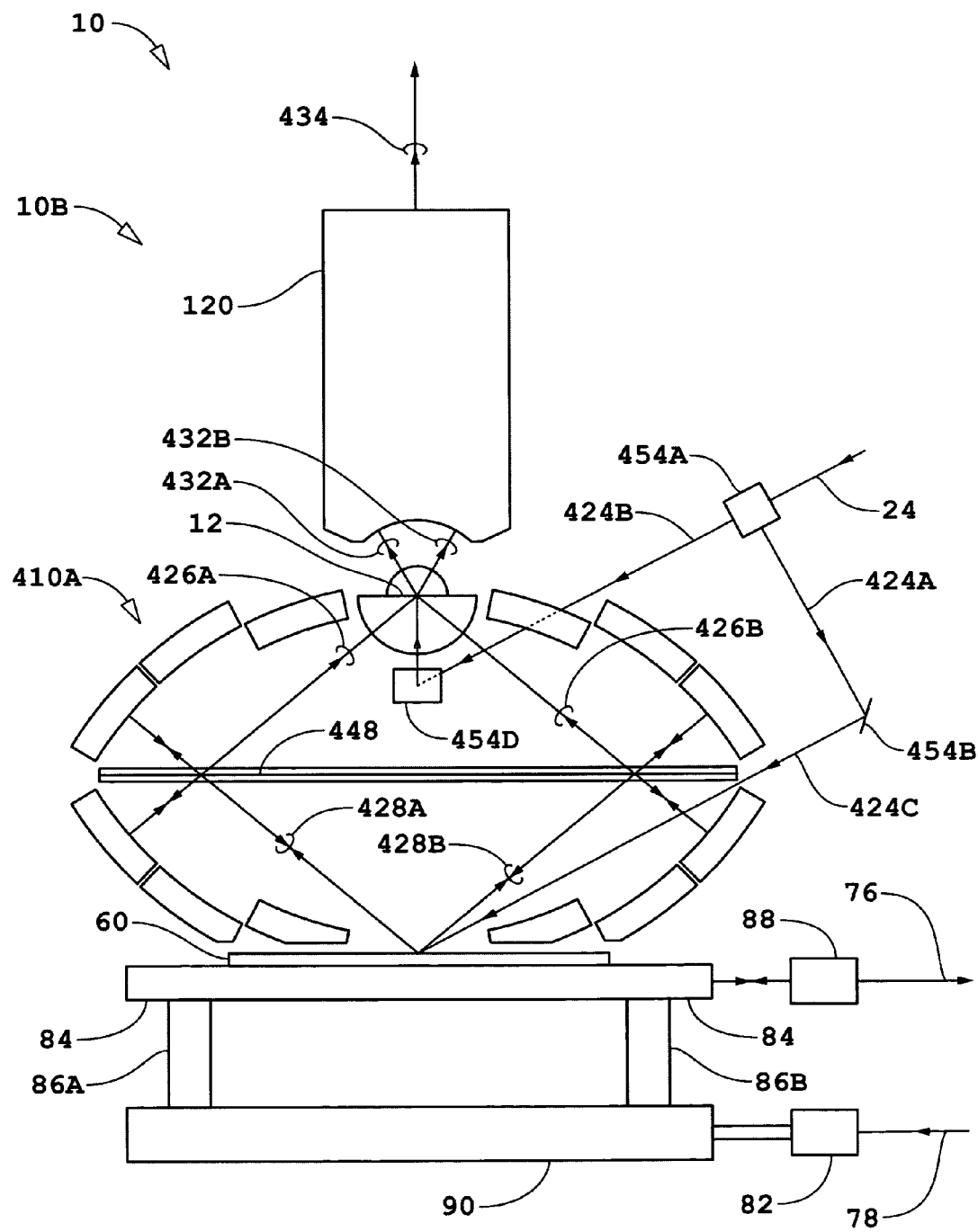
FIG. 4a is a schematic diagram of an interferometric non-confocal microscope system operating in a reflection mode that uses a catadioptric imaging system comprising a pellicle beam-splitter and adaptive catoptric surfaces.

A sixth embodiment of the present invention is shown schematically in FIG. 4a that uses an interferometer 10 and catadioptric imaging system comprising a thin beam-splitter. Interferometer 10 of the sixth embodiment comprises a first imaging system generally indicated as numeral 410A, thin fluorescent layer 12, and a second imaging system generally indicated as numeral 10B. The description of second imaging system 10B of the sixth embodiment is the same as the description given for the second imaging system 10B of the first embodiment of the present invention.

Figure 4B:
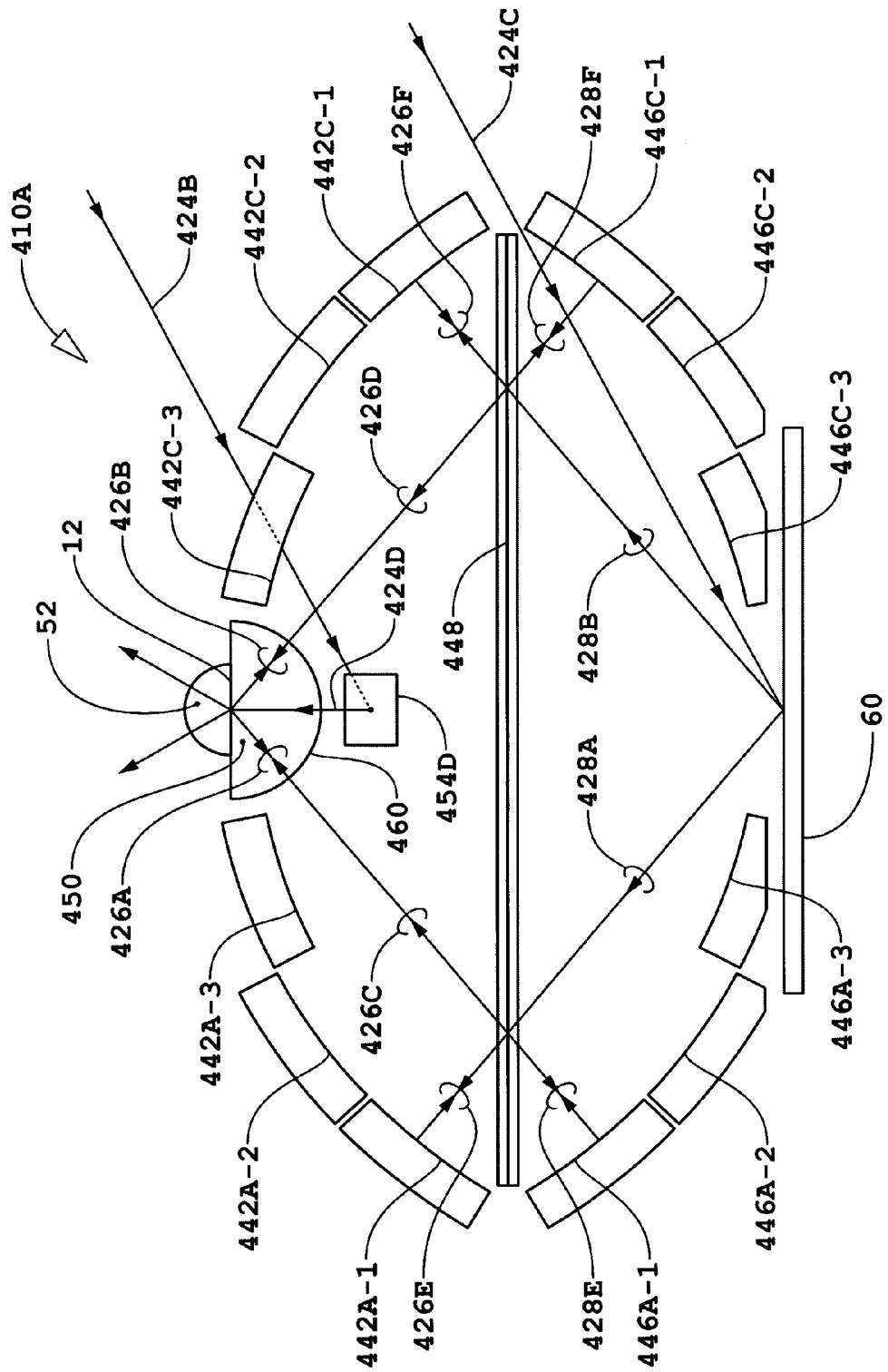
FIG. 4b is a diagram of a catadioptric imaging system comprising a pellicle beam-splitter and adaptive catoptric reflecting surfaces.

First imaging system 410A is a catadioptric imaging system and comprises adaptive reflective surfaces and a thin beam-splitter 448 which are shown schematically in FIG. 4b. Beam-splitter 448 is thin with respect to the generation of optical aberrations. The adaptive reflective surfaces are elements 442A-1, 442A-2, 442A-3, 442C-1, 442C-2, 442C-3, 446A-1, 446A-2, 446A-3, 446C-1, 446A-2, and 446C-3. The adaptive reflective surfaces with transducers and servo control signals are shown schematically in FIG. 4c. Catadioptric imaging system 410A further comprises convex lens 450.

The adaptive reflective surface elements 442A-1, 442A-2, 442A-3, 442C-1, 442C-2, 442C-3, 446A-1, 446A-2, 446A-3, 446C-1, 446A-2, and 446C-3, as well as beam-splitter 448 are held in place by frame structure that is not shown. The beam-splitter 448, which is supported around its outer perimeter, would typically be referred to as a self-supporting beam splitter, which means that there is no external support which contacts or supports any portion of the beam-splitter in its central region away from its perimeter.

Reflecting surfaces 442A-1, 442A-2, 442C-1, and 442C-2 comprise nominally a first single concave reflecting surface and reflecting surfaces 442A-3 and 442C-3 comprise nominally a second single concave reflecting surface. The first and second single concave reflecting surfaces have the same nominal centers of curvature. Reflecting surfaces 446A-1, 446A-2, 446C-1, and 446C-2 comprise nominally a third single concave reflecting surface and reflecting surfaces 446A-3 and 446C-3 comprise nominally a fourth single concave reflecting surface. The third and fourth concave reflecting surfaces have the same nominal centers of curvature. The centers of curvatures of the first and second concave reflective surfaces are the same as the conjugate of the centers of curvatures of the third and fourth concave reflective surfaces generated by beam-splitter 448. Accordingly, the centers of curvatures of the third and fourth concave reflective surfaces are the same as the conjugate of the centers of curvatures of the first and second concave reflective surfaces generated by beam-splitter 448.

The first and second concave reflective surfaces and the third and fourth concave reflective surfaces correspond to Fresnel mirrors of a catoptric imaging system such as described in cited U.S. Pat. No. 6,717,736. The center of curvature of convex lens 450 is the same as the centers of curvature of the third and fourth concave reflective surfaces. The radius of curvature of convex lens 450 is selected so that the off-axis aberrations of the catadioptric imaging system 410A are compensated. The medium of convex lens 450 may be for example fused silica or $CaF_2$ for operation in the UV or $CaF_2$ or LiF for operation in the VUV.

Adaptive reflecting surfaces 442A-1, 442A-2, 442A-3, 442C-1, 442C-2, and 442C-3 and adaptive reflecting surfaces 446A-1, 446A-2, 446A-3, 446C-1, 446C-2 and 446C-3 shown in FIG. 4b may each be representative of annular rings or of sections of annular rings. The remaining description of the sixth embodiment will be based on a simple configuration wherein there are no additional reflecting surfaces beyond those described as a non-limiting example without departing from the scope and spirit of the present invention. The number of corresponding adaptive reflecting surfaces defines of the range of values of N that may be used in the N-dimensional bi- or quad-homodyne detection methods. In the non-limiting example of the simple configuration shown in FIG. 4b, the maximum value for N is 6.

Figure 4C:
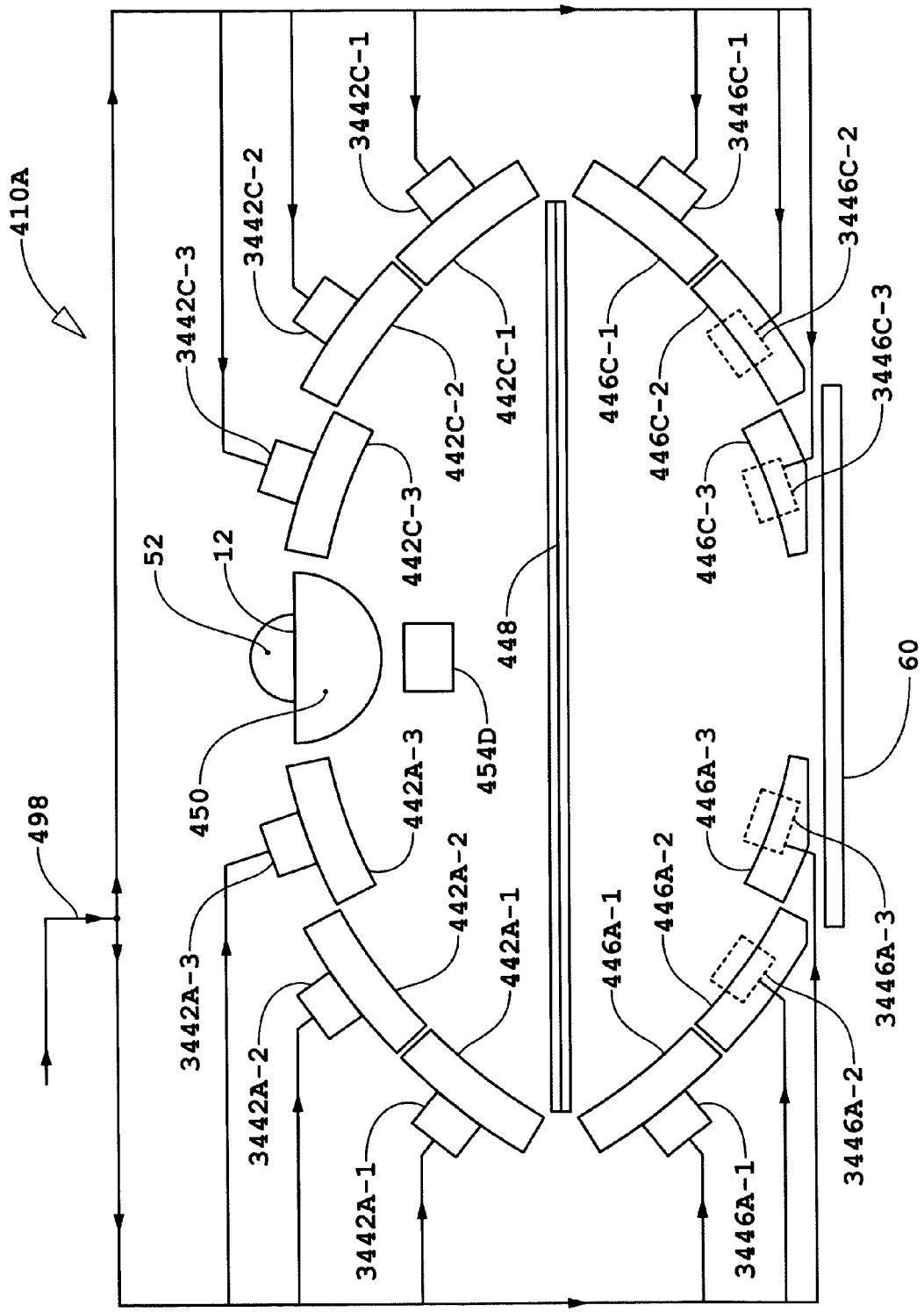
FIG. 4c is a diagram of a catadioptric imaging system comprising a pellicle beam-splitter and adaptive catoptric surfaces attached to displacement transducers.

Referring to FIG. 4c, the locations and orientations of adaptive reflecting surfaces are controlled by transducers according to servo control signal 498. The description of servo control signal 498 is the same as the corresponding description of servo control signal 98 from servo controller 96 shown in FIG. 1a. For each of the adaptive reflective surfaces 442A-1, 442A-2, 442A-3, 442C-1, 442C-2, 442C-3, 446A-1, 446A-2, 446A-3, 446C-1, 446C-2, and 446C-3, there are corresponding transducers 3442A-1, 3442A-2, 3442A-3, 3442C-1, 3442C-2, 3442C-3, 3446A-1, 3446A-2, 3446A-3, 3446C-1, 3446C-2, and 3446C-3, respectively. Each of the transducers comprises three transducers that can either change the radial position of a corresponding adaptive reflective surface or effect changes in the orientation of the corresponding adaptive reflective surface in two orthogonal planes. The two orthogonal planes intersect in a line that is parallel to the optical axis of the corresponding adaptive reflective surface. Certain of the transducers are located so as to not interfere with substrate 60 and are indicate as dashed lines in FIG. 4c.

The working distance of interferometer 10 in FIG. 4a can be increased for example by removing the adaptive reflective surfaces 446A-3, 446C-3, 442A-3, and 442C-3 at the expense of increasing the size of the central obstruction presented to beams reflected/scattered or transmitted by the catadioptric imaging system.

Referring to FIG. 4a, when input beam 24 comprises coextensive reference and measurement beams, first and second portions of input beam 24 are reflected and transmitted, respectively, by beam-splitter mirror system 454A that comprises a non-polarizing beam-splitter as a measurement beam 424A and as reference beam 424B. When input beam 24 comprises non-coextensive reference and measurement beams, element 454A functions as a set of mirrors to reflect the measurement beam component of beam 24 as beam 424A and the reference beam component beam of 24 as reference beam 424A. Propagation of measurement beam 424A is in the plane of FIG. 4a and is reflected by mirror 454B as measurement beam 424C. Propagation of reference beam 424B is displaced out of the plane of FIG. 4a and directed toward mirror system 454D. Reference beam 424B exits mirror system 454D as reference beam 424D (see FIG. 4b). Propagation of reference beam 424D is in the plane of FIG. 4b and is incident on thin fluorescent layer 12. Output beam 434 shown in FIG. 4a corresponds to output beam 34 shown in FIG. 1a.

Figure 4D:
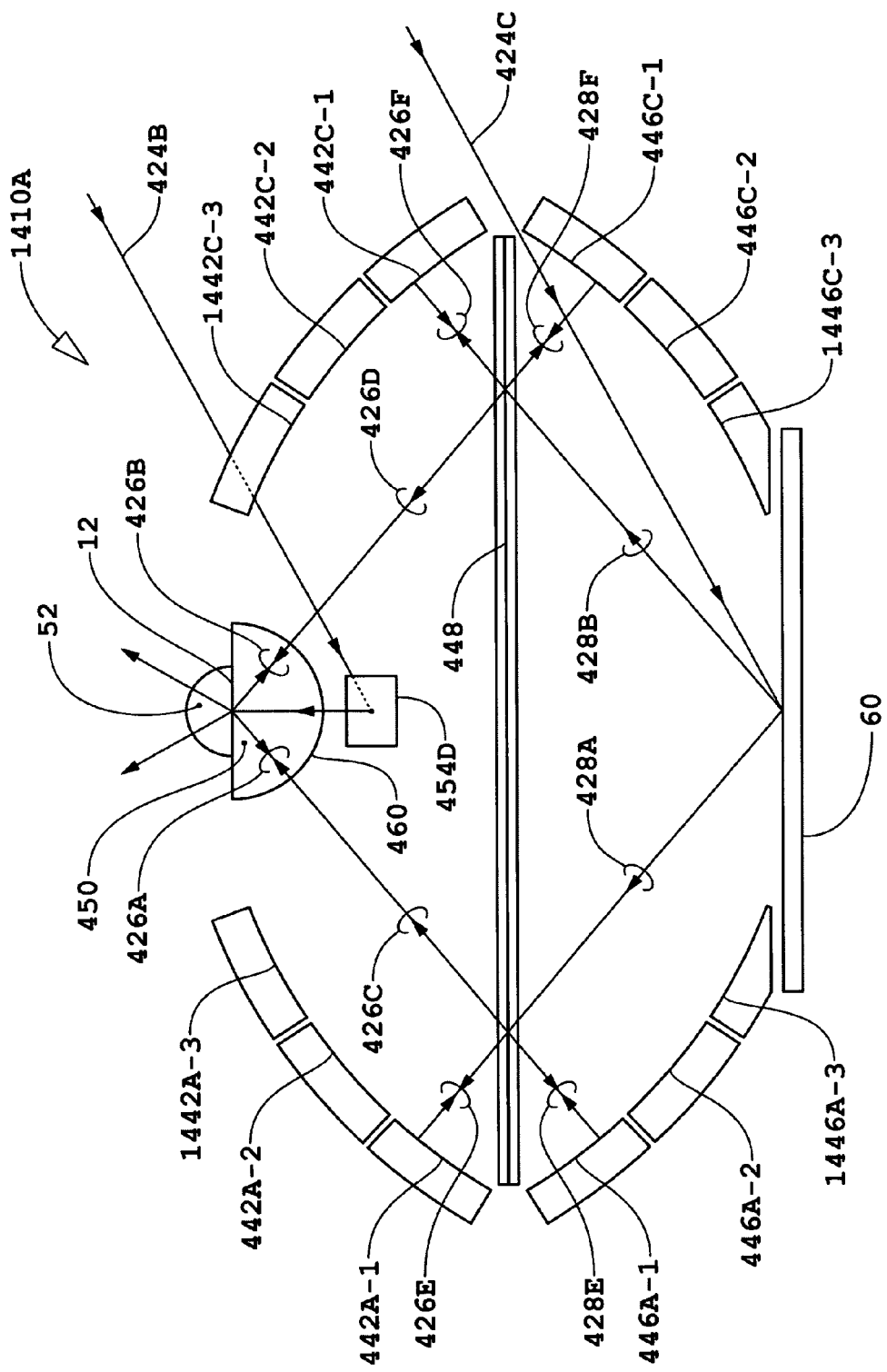
FIG. 4d is a schematic diagram of an interferometric non-confocal microscope system that uses a catadioptric imaging system comprising a pellicle beam-splitter.
Figure 4E:
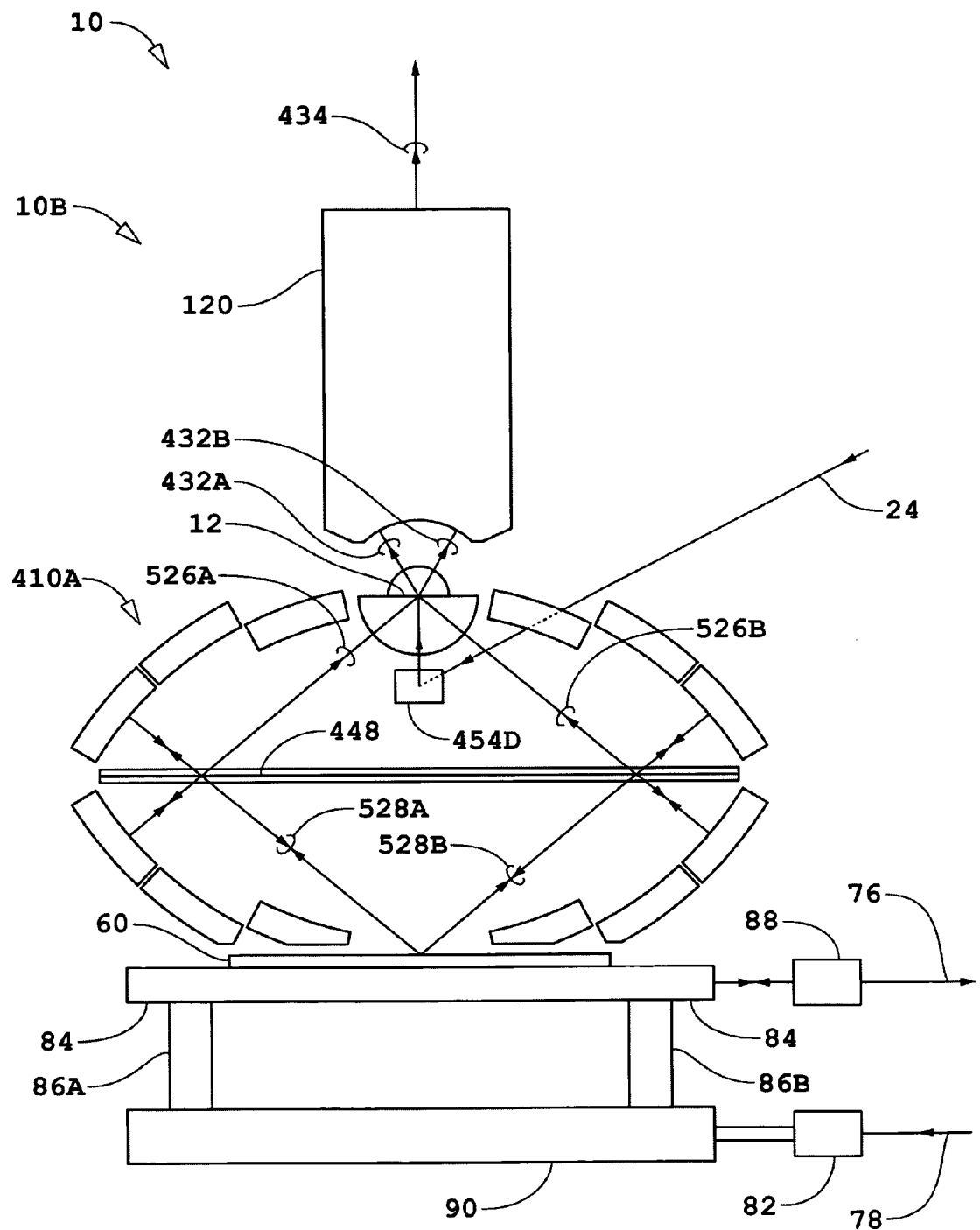
FIG. 4e is a schematic diagram of an interferometric confocal microscope system that uses a catadioptric imaging system comprising a pellicle beam-splitter.
Figure 4F:
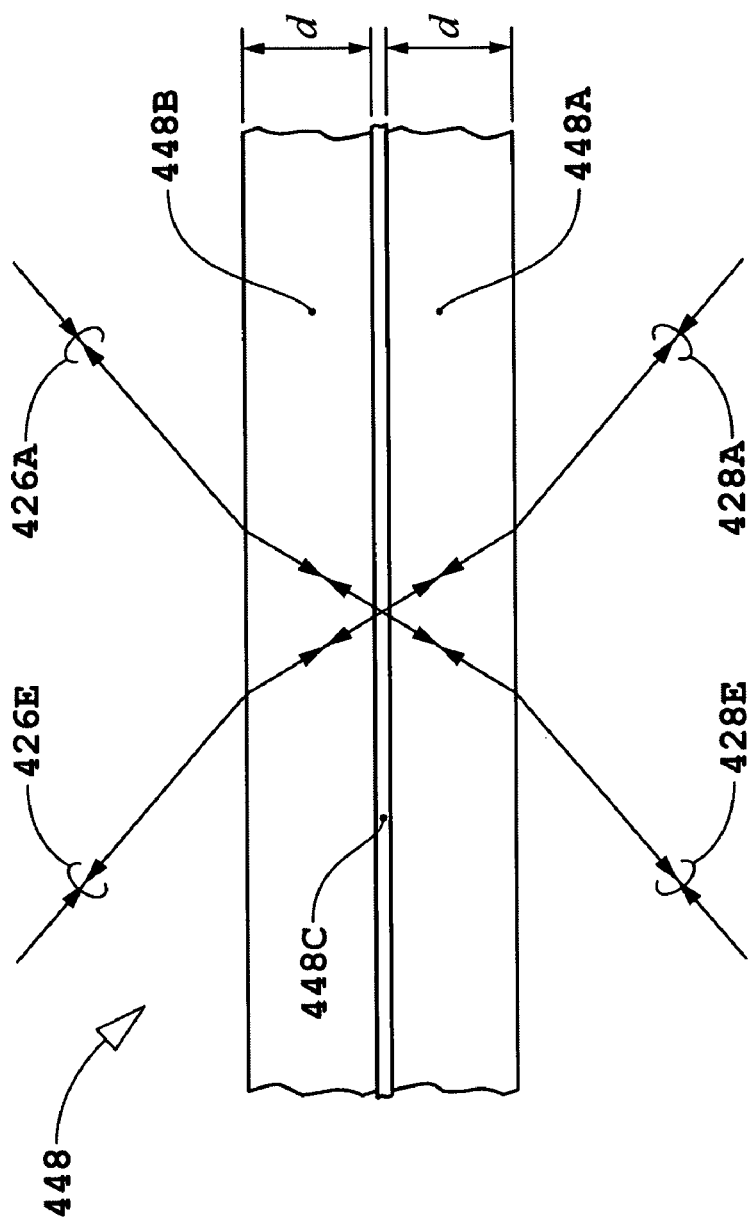
FIG. 4f is a schematic diagram of a section of a pellicle beam-splitter.

The function of beam-splitter 448 is the same as the function of beam-splitter 48 of the first embodiment of the present invention with respect generating complimentary beams 426E and 428E and complimentary beam 426F and 428F [see FIG. 4f and the discussion associated with Equation (1)]. Beam-splitter 448 is shown schematically in Fib. 4f and comprises two pellicles 448A and 448B and beam-splitting layer 448C. The refractive media, e.g., UV grade fused silica, $F—SiO_2$, $CaF_2$, or LiF, of pellicles 448A and 448B is selected to meet the transmission requirements of an end use application. The thickness d of pellicles 448A and 448B is selected to be small as practical in order to reduce optical aberrations introduced by the pellicles consistent with the pellicles being self supporting, meeting required flatness specifications, and meeting required uniformity of thickness specifications.

The residual optical aberrations introduced by the finite thickness of thin beam-splitter 448 and departures of thin beam-splitter 448 may be compensated in part in catadioptric imaging system 410A by modifying the shapes and adjusting the positions and locations of the adaptive reflective surfaces 442A-1, 442A-2, 442A-3, 442C-1, 442C-2, 442C-3, 446A-1, 446A-2, 446A-3, 446C-1, 446C-2, and 446C-3.

The beam-splitter 448 comprising pellicles is shown as lying in a horizontal plane in the FIGS. 4a, 4b, and 4c of sixth embodiment. However, the effect of the earths' gravitational field may introduce an unacceptable level of the sag in the pellicles and accordingly, the orientation of the pellicles will preferably be in a vertical plane.

The use of UV grade fused silica, $F—SiO_2$, $CaF_2$, or LiF for pellicles 448A and 448B permit operation of the catadioptric imaging system 410A down to approximately 200 nm, 140 nm, and 110 nm, respectively. Other UV and VUV grade media may be used such as $BaF_2$ and $SrF_2$. The wavelength range can be extended below 110 nm by converting catadioptric imaging system 410A to a catoptric imaging system. The conversion is achieved by removal of convex lens 450 and the generation of beam-splitter 448 as catoptric grade beam-splitter.

Figure 9A:
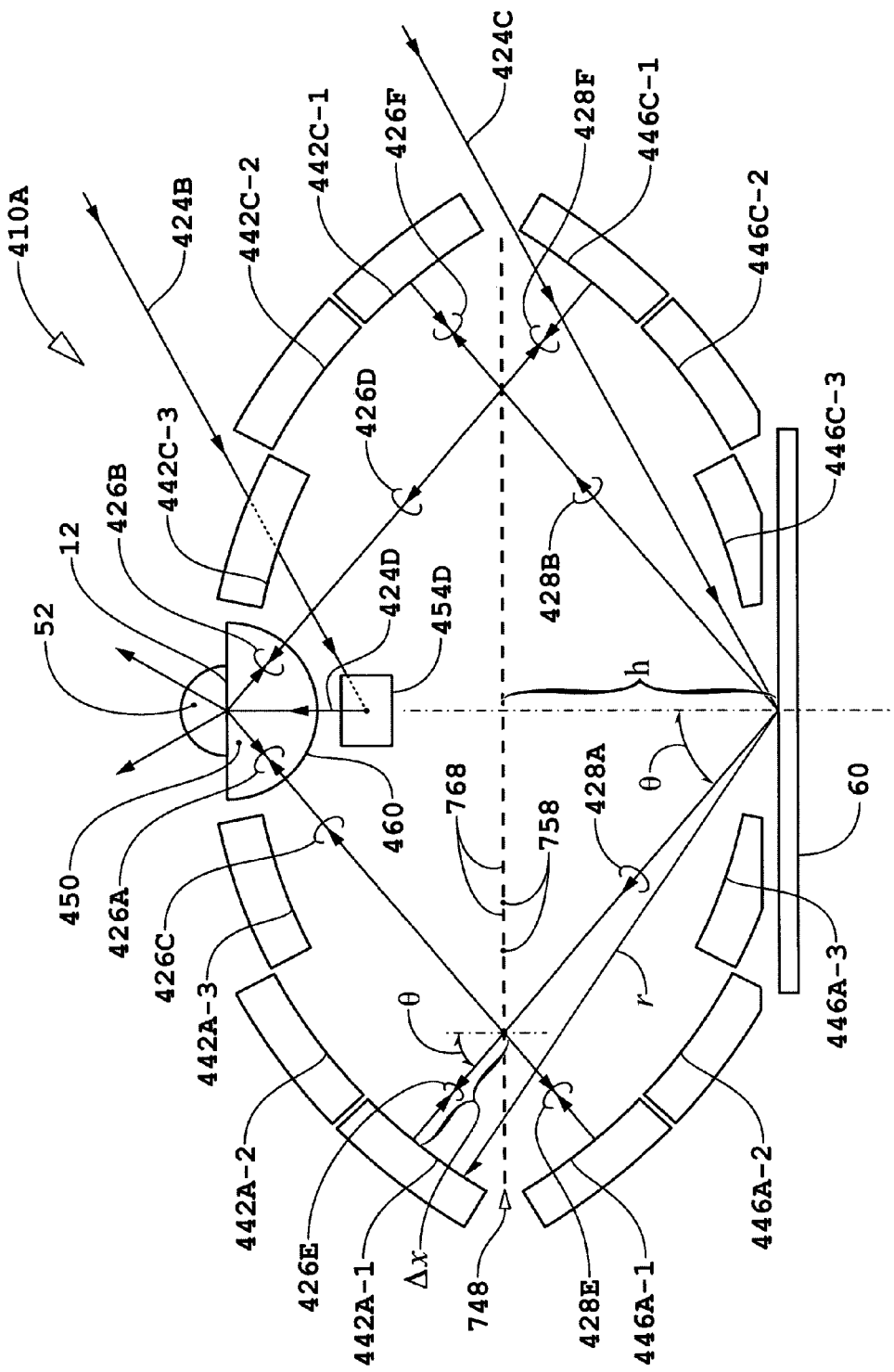
FIG. 9a is a diagram of a catadioptric imaging system illustrating the radial and azimuthal directions.
Figure 9B:
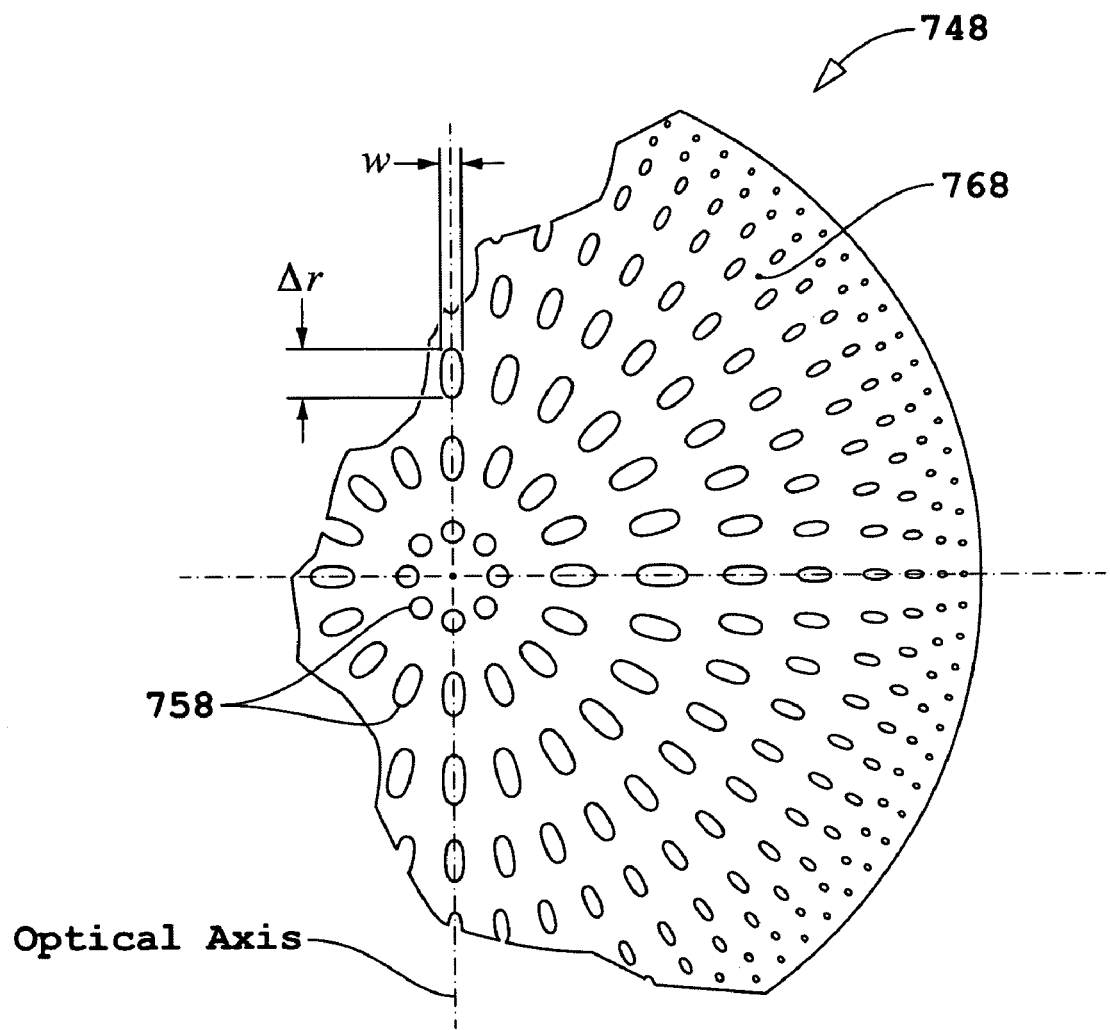
FIG. 9b shows a beam splitter with an array of transmitting apertures.

A catoptric grade beam-splitter may be produced as a pellicle beam-splitter or an array of apertures in a reflecting self-supporting layer of one or more refractive media. A beam-splitter 748 comprising an array of apertures 758 in a reflecting self supporting layer 768 is shown schematically in FIGS. 9a and 9b. The description of catadioptric imaging system 410A shown in FIG. 9a is the same as the description of catadioptric imaging system 410A shown in FIG. 4b except with pellicle beam-splitter 48 replaced by the aperture array beam-splitter 748. The density of apertures 758 is chosen such that the net reflection and transmission coefficients for beam-splitter 748 are nominally equal at each location on beam-splitter 748.

There are conditions placed on the selection of the radial and azimuthal dimensions Δr and w, respectively, of apertures 758 for an optimal performance of beam-splitter 748 which impact on the selection of the density of the apertures 758. These conditions are expressed by the formulae $$\lambda \Delta x \geq 3 (\Delta r \cos\theta)^2, \quad (21)$$

$$\lambda \Delta x \geq 3 w^2, \quad (22)$$

where $\Delta x$ is an average path length of measurement and/or reference beams from beam-splitter 748 to the respective adaptive reflective surface, e.g., beams 426E, 426F, 428E, and 428F and adaptive reflective surfaces 442A-1, 442C-1, 446A-1, and 446C-1, respectively, shown in FIG. 9a and $\theta$ is a corresponding average angle of incidence at the beam-splitter. The radial and azimuthal dimensions for the apertures of the aperture array will generally be different for optimum performance of the beam-splitter. In addition, the radial and azimuthal dimensions of the apertures will generally be dependent on the angle of incidence $\theta$ of a beam, the radius of curvature r of a respective adaptive reflective surface, and h the spacing between beam-splitter 748 and the center of curvature of the respective adaptive reflective surface (see FIG. 9a). Equations (21) and (22) can be written in terms of h and r explicitly for $\Delta r$ and w with the results $$\Delta r \leq \left[ \frac{\lambda(r - h\sec\theta)}{3} \right]^{1/2} \sec\theta, \quad (23)$$

$$w \leq \left[ \frac{\lambda(r - h\sec\theta)}{3} \right]^{1/2}, \quad (24)$$

respectively. The value of w starts off with a value of $w \leq [\lambda(r-h)/3]^{1/2}$ for $\theta=0$ and decreases to a value of zero when $\theta$ reaches in maximum value of $\cos^{-1}(h/r)$. The value of $\Delta r$ also starts off at $\theta=0$ with a value of $\Delta r \leq [\lambda(r-h)/3]^{1/2}$, e.g., $\Delta r \leq 0.408(\lambda r)^{1/2}$ for h=0.5r, then increases to a maximum value at $\theta$=42 degrees for the example h=0.5r, i.e. $\Delta r \leq 0.444(\lambda r)^{1/2}$, and then decreases to a value of zero when $\theta$ reaches the maximum value of $\cos^{-1}(h/r)$ which is 60 degrees for the example h=0.5r.

The operation with a catoptric grade beam-splitter 448 and convex lens 450 removed reduces the optical path lengths of measurement beams in a refractive and potentially dispersive media to zero. However, the field of view is reduced since the off-axis aberrations introduced by the adaptive reflective surfaces are no longer compensated.

Microlithography techniques or MEMS techniques can be used for the manufacture of the catoptric grade beam-splitters generated as an array of apertures in a pellicle that has reflective surfaces. The catoptric beam-splitter can also be manufactured as crossed arrays or grids of conducting wires such as applicable for longer wavelengths.

The selection of the radius of curvature of convex lens 450 is based on the same considerations presented in the section included herein entitled "Selection of Radii of Curvature" and given with respect to the first embodiment of the present invention. At $\lambda$=250 nm and a radius of curvature for the adaptive reflective surfaces of 50 mm, the corresponding radius of curvature for convex lens 450 comprising $CaF_2$ is 7.96 mm. Achromatic designs for the off-axis aberration compensating convex lens may also be used in the sixth embodiment without departing from the spirit and scope of the present invention. The design of the corresponding achromatic configurations is based on the same considerations presented in the section included herein entitled "Selection of Radii of Curvature" and given with respect to design of achromatic designs of the first embodiment of the present invention.

When using a Fresnel adaptive reflective surfaces such as in the sixth embodiment of the present invention, the selection of the radius of curvature of an off-axis aberration compensating refractive element such as convex lens 450 is based on consideration the radii of curvature of the adaptive reflective surfaces that introduce the largest off-axis aberrations. The magnitude of the off-axis aberrations generated by an adaptive reflective element is a non-linear function of the angle of corresponding measurement beams measured with respect to the optical axis of the catadioptric imaging system and generally increases as the angle of corresponding measurement beams increases. Thus for the adaptive reflective surfaces of the catadioptric imaging system 410A, the nominal radius of curvature of the first and third single concave reflecting surfaces is used in the design of the radius of surface 460 of convex lens 450.

An important property of the sixth embodiment is reduced off-axis aberrations that need to be compensated by convex lens 450. The off-axis aberrations of the sixth embodiment are reduced by a factor of approximately two compared to the magnitude of off-axis aberrations that need to be compensated by convex lens 50 of the first embodiment of the present invention. This is because the sign of off-axis aberrations of concave refractive surfaces such as 42B and 46B of the first embodiment (see FIG. 1c) is the same as the sign of the off-axis aberrations introduced by reflective concave surfaces in the catadioptric imaging systems 10A and 410A. In addition, the magnitudes of the net off-axis aberrations of the concave refractive surfaces 42B and 46B and convex refractive surfaces 42A and 46A of the first embodiment (see FIG. 1c) are approximately the same as the magnitudes of the off-axis aberrations introduced by reflective concave surfaces in the catadioptric imaging systems 10A and 410A. A consequence of the important property is an increased field of view for a given level of off-axis aberrations or reduced off-axis aberrations for a specified field of view.

An advantage of this configuration is that only air or vacuum separates the beam splitter from the reflecting surfaces so the index of refraction seen by a beam that is being focused by the system is much lower than it is when catadioptric elements 40 and 44 (see FIG. 1c) are used. This design removes much, if not all, of the glass that was in these regions separating the reflecting surfaces and the beam splitter. This means that for any given beam, the optical distance between the beam splitter and the reflecting surfaces is approximately equal to the physical distance.

So, another important property of the sixth embodiment is a reduced optical path length in a refractive medium which is particularly important when working in the IR, UV, VUV, or EUV. The optical path length in a refractive medium in the sixth embodiment is approximately $\frac{1}{10}$ of the optical path length in a refractive medium for those embodiments that are not based on use of a thin beam-splitter. A consequence of the another important property is an extended range into the IR, UV, VUV and/or in the EUV for a given refractive medium.

A variant of catadioptric imaging system 410A is shown schematically in FIG. 4d as catadioptric imaging system 1410A. Catadioptric imaging system 1410A is the same as catadioptric imaging system 410A except that the nominal radii of curvature for the adaptive reflective surfaces of catadioptric imaging system 1410A corresponding to the first, second, third, and fourth single concave reflecting surfaces of the sixth embodiment are all equal. The remaining description of the variant of catadioptric imaging system 1410A is the same as the corresponding portion of the description given for catadioptric imaging system 410A.

The seventh embodiment of the present invention comprising interferometer system 10 is shown diagrammatically in FIG. 4e. The catadioptric imaging system 410A of the seventh embodiment is the same as the catadioptric imaging system 410A of the sixth embodiment of the present invention except that catadioptric imaging system 410A of the seventh embodiment is configured to function as a confocal imaging system and that thin film fluorescent layer 12 is replaced by a pinhole array beam-splitter 12 shown schematically in FIG. 1f. The pinhole array beam-splitter 12 is used as the beam-splitter for generating the reference and measurement beams and for the function of combining the reference beam and measurement beam reflected/scattered by substrate 60.

The remaining description of the seventh embodiment is the same as corresponding portions of descriptions given for the second and sixth embodiments of the present invention.

Figure 4G:
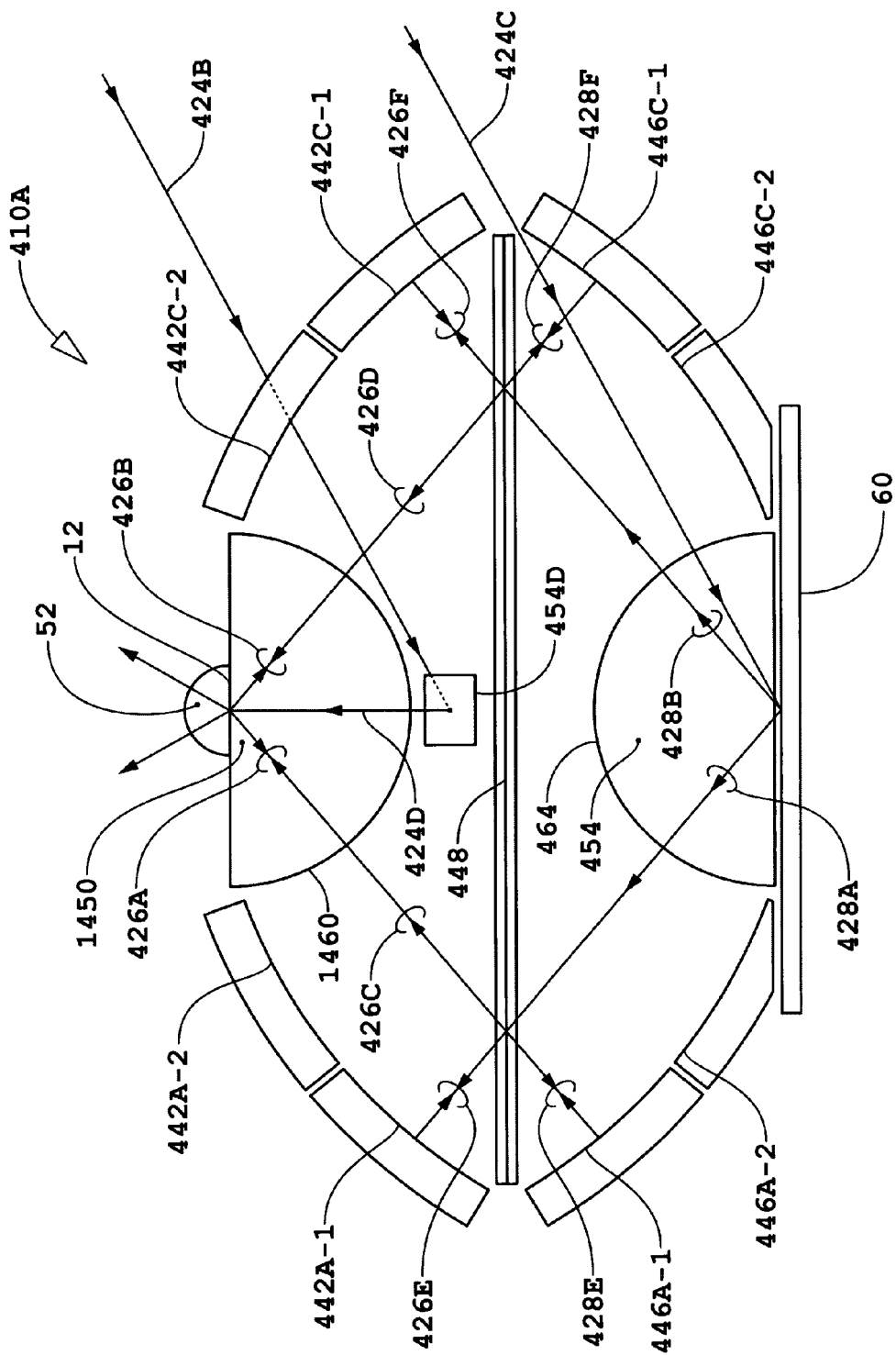
FIG. 4g is a diagram of a catadioptric imaging system for a non-confocal interferometric microscope comprising a pellicle beam-splitter and adaptive catoptric reflecting surfaces.

A variant of the catadioptric imaging system 410A of the sixth embodiment of the present invention is shown diagrammatically as catadioptric imaging system 2410A in FIG. 4g. The variant of catadioptric imaging system 410A comprises the elements of catadioptric imaging system 410A except for convex lens 450. In the variant, convex lenses 1450 and 454 together compensate for the off-axis aberrations of catadioptric imaging system 410A. The centers of curvature of lenses 454 and 1450 are the same as the center of curvature of the first and second single concave reflective surfaces and the center of curvature of the third and fourth single concave reflective surfaces, respectively. The selection of radii of curvature for lenses 454 and 1450 is based on the same considerations described with respect to the third embodiment of the present invention. At $\lambda=250$ nm and a radius of curvature for the adaptive reflective surfaces of 50 mm, the corresponding radii of curvature for convex lens 454 and 1450 comprising $CaF_2$ is 15.92 mm.

An advantage of the variant of the sixth embodiment is the same as an advantage of the third embodiment of the present invention. The location of the object plane of catadioptric imaging system 410A may also be on the plane surface of plano convex lens 454. In this case, the measurement beam can be arranged to probe substrate 60 as an evanescent field when the spacing between plano convex lens 454 and substrate 60 is of the order of $\lambda/4$. The variant of the sixth embodiment can change rapidly from using the evanescent field as a probe beam to using the non-evanescent fields as a probe beam by use of the high speed vertical scan feature of the present invention.

Figure 5:
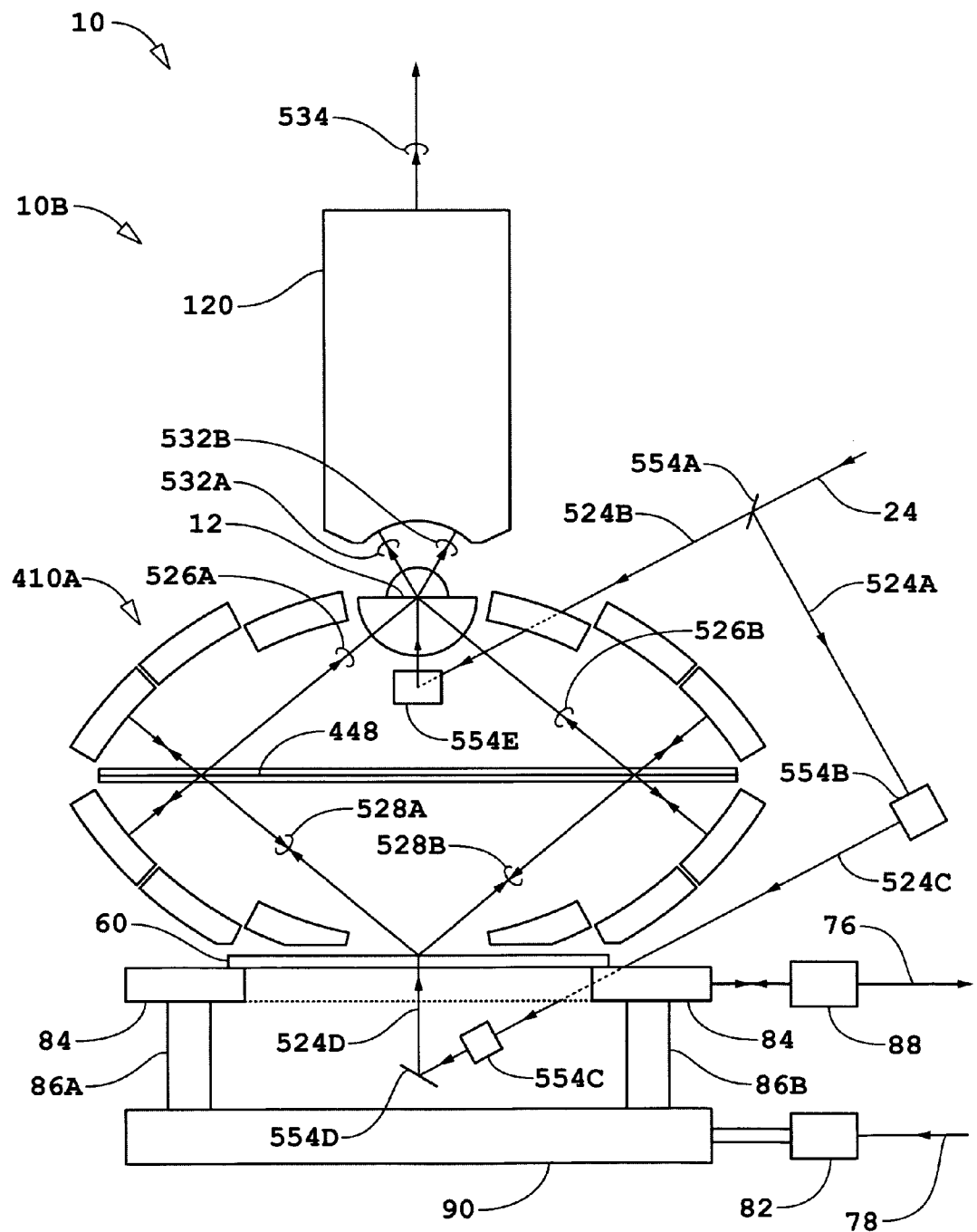
FIG. 5 is schematic diagram of an interferometric non-confocal microscope system operating in a transmission mode that uses a catadioptric imaging system comprising a pellicle beam-splitter and adaptive catoptric surfaces.

The eighth embodiment of the present invention comprises an interferometer system operating in a transmission mode such as described with respect to FIG. 3a. An interferometer 10 of the eighth embodiment is shown diagrammatically in FIG. 5. Catadioptric imaging system 10 shown in FIG. 5 comprises catadioptric imaging system 410A of the sixth embodiment of the present invention and the second imaging system 10B that is the same as the second imaging system of the fifth embodiment of the present invention.

Beams 532A, 532B, and 534 of the eighth embodiment correspond with respect to general descriptions to beams 432A, 432B, and 434 of the sixth embodiment. The remaining description of the eighth embodiment is the same as corresponding portions of the descriptions given for the fifth and sixth embodiments of the present invention.

Figure 6A:
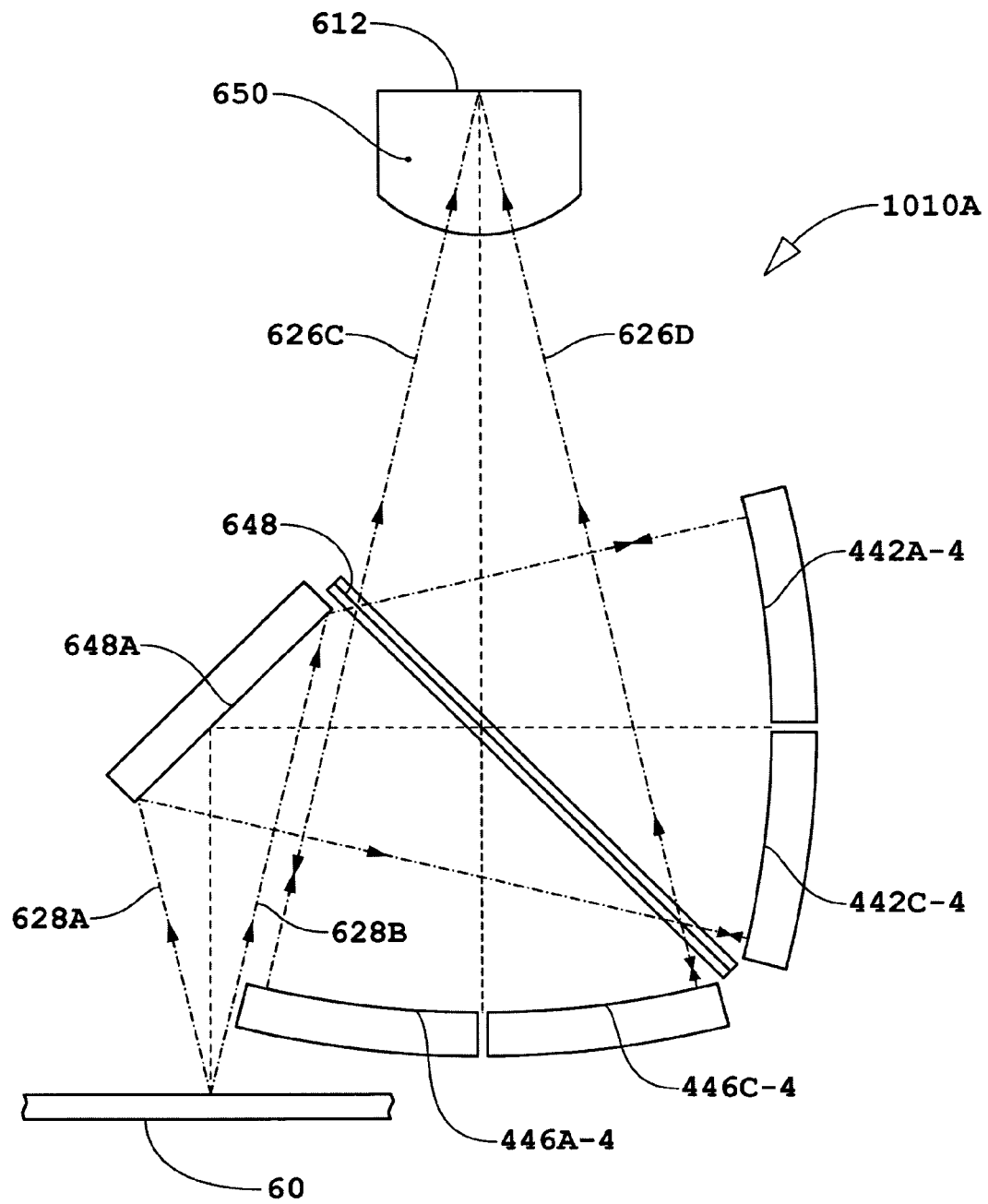
FIG. 6a is a diagram of a catadioptric imaging system comprising a pellicle beam-splitter and adaptive catoptric surfaces that is configured for imaging the reflected/scattered fields at nominal zero angle of reflectance.

For each of the embodiments and variants thereof of the present invention, there is a limitation where the central portion of measurement beams reflected/scattered by substrate 60 is not measured because of the obstruction presented by the convex lens used for compensating for off-axis aberrations. The limitation is removed in a variant of each of the embodiments and variants thereof of the present invention by the addition of a catadioptric imaging system 1010A shown schematically in FIG. 6a of the present invention.

The variant of the sixth embodiment wherein the limitation is removed by the addition of catadioptric imaging system 1010A will be described as an example of the each of the embodiments and variants thereof.

Figure 6B:
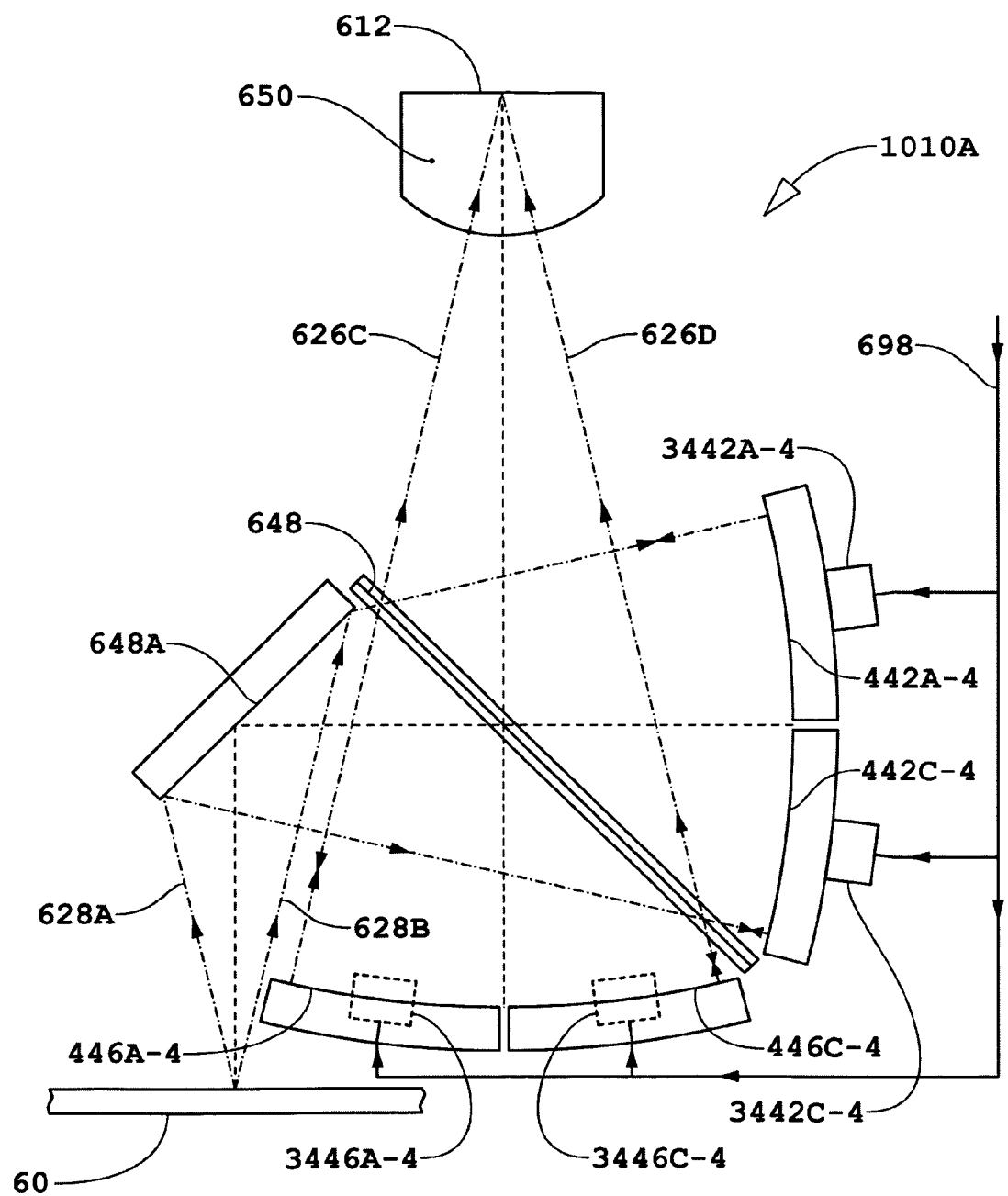
FIG. 6b is a diagram of a catadioptric imaging system comprising a pellicle beam-splitter and adaptive catoptric surfaces with transducers attached that is configured for imaging the reflected/scattered fields at nominal zero angle of reflectance.

Catadioptric imaging system 1010A is a variant of the catadioptric imaging system shown in FIG. 6 of cited U.S. Pat. No. 6,552,852. Catadioptric imaging system 1010A comprises adaptive reflective surfaces 442A-4, 442C-4, 446A-4, and 446C-4; convex lens 650, and pellicle type beam-splitter 648. Catadioptric imaging system 1010A further comprises mirror 648A that is placed in the measurement beam path of catadioptric imaging system 410A such as to redirect portions of the measurement beams that would otherwise be obstructed by lens 450. By the redirection of the portions of the measurement beams to catadioptric imaging system 1010A, both catadioptric imaging systems 410A and 1410A can be operational simultaneously.

The radii of curvature of adaptive reflective surfaces 442A-4, 442C-4, 446A-4, and 446C-4 are preferably the same as the nominal radii of curvature of the first and third single concave reflecting surfaces of catadioptric imaging system 410A. Also the radius of curvature and refractive media of convex lens 650 are preferably the same as the radius of curvature and refractive medial of convex lens 450. The positions and angular orientations of adaptive reflective surfaces 442A-4, 442C-4, 446A-4, and 446C-4 are controlled by transducers 3442A-4, 3442C-4, 3446A-4, and 3446C-4 shown schematically in FIG. 6b. Transducers 3442A-4, 3442C-4, 3446A-4, and 3446C-4 are controlled be servo signal 698 which corresponds to servo signal 498.

The addition of catadioptric imaging system 1410A makes in possible to operate the variant of the sixth embodiment of the present invention in an N-dimensional bi- or quad-homodyne detection method wherein the maximum value for N is 8.

The remaining description of the variant of the sixth embodiment is the same as corresponding portions of the description given for the sixth embodiment of the present invention.

Applications

The catadioptric imaging systems described above can be especially useful in alignment mark identification on a stepper or scanner of lithography applications used for fabricating large scale integrated circuits such as computer chips and the like and in a stand-alone metrology system for measuring overlay performance of the stepper or scanner. The catadioptric imaging systems described above can also be especially useful in inspection of masks used in the stepper or scanner and in the inspection of wafers at different stages of the fabrication of large-scale integrated circuits.

Lithography is the key technology driver for the semiconductor manufacturing industry. In particular, overlay improvement is one of the five most difficult challenges down to and below 100 nm line widths (design rules), see, for example, the *Semiconductor Industry Roadmap*, p82

(1997). Since a lithography tool may produce $50–100M/year of product, the economic value from improving (maintaining) performance of the lithography tool is substantial. Each 1% increase (loss) in yield of the lithography tool results in approximately $1M/year economic benefit (loss) to the integrated circuit manufacturer and a substantial competitive advantage or disadvantage to the lithography tool vendor.

Overlay is measured by printing one pattern on one level of a wafer and a second pattern on a consecutive level of the wafer and then measuring, on a stand-alone metrology system, the difference in the position, orientation, and distortion of the two patterns.

A stand-alone metrology system for measuring overlay comprises a microscope system for viewing the patterns, such as the catadioptric imaging systems described above, connected to laser gauge-controlled stage for measuring the relative positions of the patterns, and a wafer handling system.

The function of a lithography tool is to direct spatially patterned radiation onto a photoresist-coated wafer. The process involves determining which location of the wafer is to receive the radiation (alignment) and applying the radiation to the photoresist at that location.

To properly position the wafer, the wafer includes alignment marks on the wafer that can be measured by dedicated sensors such as the scanning interferometric near-field confocal systems described above. The measured positions of the alignment marks define the location of the wafer within the tool. This information, along with a specification of the desired patterning of the wafer surface, guides the alignment of the wafer relative to the spatially patterned radiation. Based on such information, a translatable stage supporting the photoresist-coated wafer moves the wafer such that the radiation will expose the correct location of the wafer.

During exposure, a radiation source illuminates a patterned reticle, which scatters the radiation to produce the spatially patterned radiation. The reticle is also referred to as a mask, and these terms are used interchangeably below. In the case of reduction lithography, a reduction lens collects the scattered radiation and forms a reduced image of the reticle pattern. Alternatively, in the case of proximity printing, the scattered radiation propagates a small distance (typically on the order of microns) before contacting the wafer to produce a 1:1 image of the reticle pattern. The radiation initiates photo-chemical processes in the resist that convert the radiation pattern into a latent image within the resist.

When a mask is made, it must be perfect. Any defects in the pattern will destroy the functionality of the semiconductor circuit that is printed with that mask. Before a mask is delivered to the semiconductor manufacturing line, it is passed through an automated mask inspection system that searches for any defects in the pattern. There are two possible strategies in mask inspection, known as die-to-database and die-to-die inspection. The first method involves an automated scanning microscope that compares the mask pattern directly with the computer data used to generate the mask. This requires a very large data handling capability, similar to that needed by the mask writer itself. Any discrepancy between the inspected mask pattern and the data set used to create it is flagged as an error. The catadioptric imaging systems described above are especially well suited for automated mask inspection with its advantages in background reduction and in the substantially simultaneous acquisition of one-dimensional line section images and two-dimensional section images.

In general, the lithography system, also referred to as an exposure system, typically includes an illumination system and a wafer positioning system. The illumination system includes a radiation source for providing radiation such as ultraviolet, visible, x-ray, electron, or ion radiation, and a reticle or mask for imparting the pattern to the radiation, thereby generating the spatially patterned radiation. In addition, for the case of reduction lithography, the illumination system can include a lens assembly for imaging the spatially patterned radiation onto the wafer. The imaged radiation exposes resist coated onto the wafer. The illumination system also includes a mask stage for supporting the mask and a positioning system for adjusting the position of the mask stage relative to the radiation directed through the mask. The wafer positioning system includes a wafer stage for supporting the wafer and a positioning system for adjusting the position of the wafer stage relative to the imaged radiation. Fabrication of integrated circuits can include multiple exposing steps. For a general reference on lithography, see, for example, J. R. Sheats and B. W. Smith, in *Microlithography: Science and Technology* (Marcel Dekker, Inc., New York, 1998), the contents of which is incorporated herein by reference.

Figure 7A:
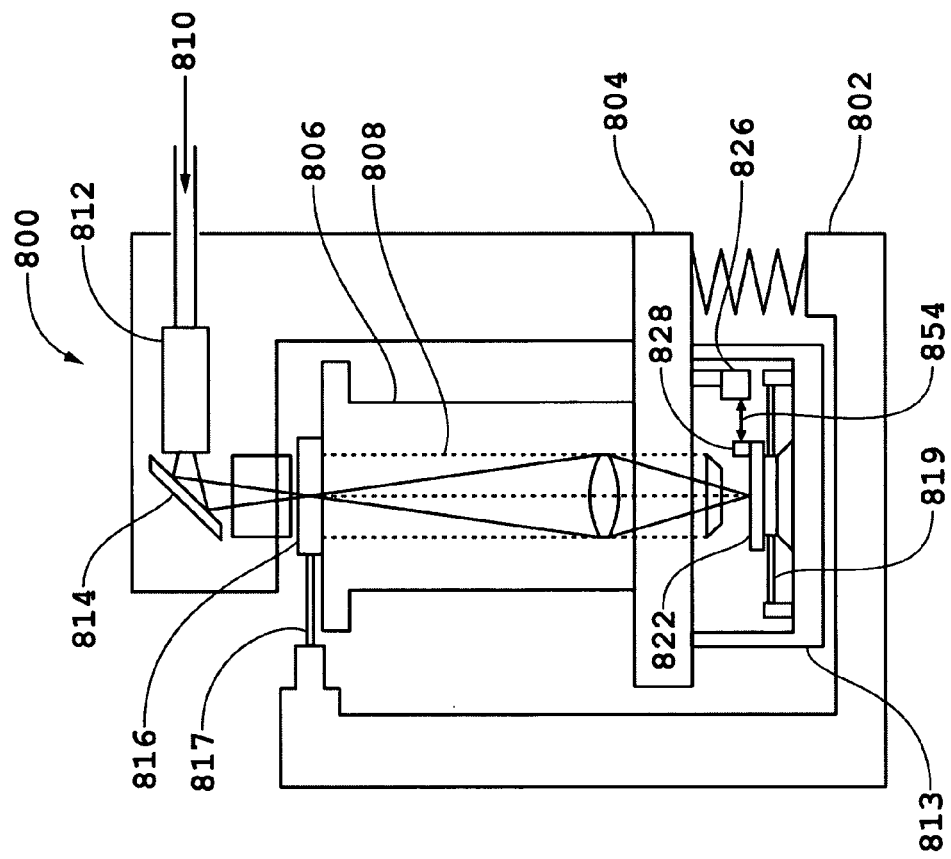
FIG. 7a is a schematic diagram of a lithography tool that uses catoptric and catadioptric imaging systems with pellicle or aperture array beam-splitters (not shown in figure).

An example of a lithography scanner 800 using a catadioptric imaging system (not shown) is shown in FIG. 7a. The catadioptric imaging system is used to precisely locate the position of alignment marks on the wafer (not shown) within an exposure system. Here, stage 822 is used to position and support the wafer relative to an exposure station. Scanner 800 includes a frame 802, which carries other support structures and various components carried on those structures. An exposure base 804 has mounted on top of it a lens housing 806 atop of which is mounted a reticle or mask stage 816, which is used to support a reticle or mask. A positioning system for positioning the mask relative to the exposure station is indicated schematically by element 817. Positioning system 817 can include, e.g., piezoelectric transducer elements and corresponding control electronics. Although, it is not included in this described embodiment, one or more interferometry systems are used to precisely measure the position of the mask stage as well as other moveable elements whose position must be accurately monitored in processes for fabricating lithographic structures (see supra Sheats and Smith *Microlithography: Science and Technology*).

Suspended below exposure base 804 is a support base 813 that carries wafer stage 822. Stage 822 includes a plane mirror 828 for reflecting a measurement beam 854 directed to the stage by interferometry system 826. A positioning system for positioning stage 822 relative to interferometry system 826 is indicated schematically by element 819. Positioning system 819 can include, e.g., piezoelectric transducer elements and corresponding control electronics. The measurement beam reflects back to the interferometry system, which is mounted on exposure base 804.

During operation, a radiation beam 810, e.g., an ultraviolet (UV) beam from a UV laser (not shown), passes through a beam shaping optics assembly 812 and travels downward after reflecting from mirror 814. Thereafter, the radiation beam passes through a mask (not shown) carried by mask stage 816. The mask (not shown) is imaged onto a wafer (not shown) on wafer stage 822 via a lens assembly 808 carried in a lens housing 806. Base 804 and the various components supported by it are isolated from environmental vibrations by a damping system depicted by spring 820.

Figure 7B:
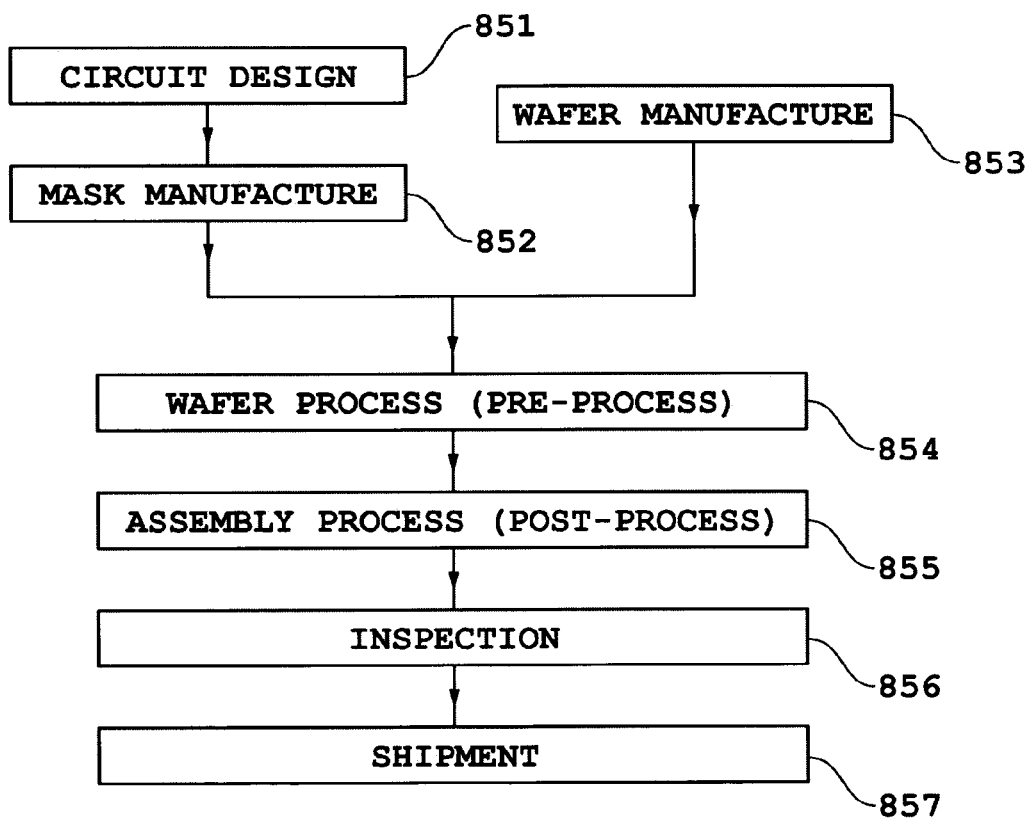
FIG. 7b is a flow chart of the sequence of manufacturing steps of a semiconductor device

As is well known in the art, lithography is a critical part of manufacturing methods for making semiconducting devices. For example, U.S. Pat. No. 5,483,343 outlines steps for such manufacturing methods. These steps are described below with reference to FIGS. 7b and 7c. FIG. 7b is a flow chart of the sequence of manufacturing a semiconductor device such as a semiconductor chip (e.g. IC or LSI), a liquid crystal panel or a CCD. Step 851 is a design process for designing the circuit of a semiconductor device. Step 852 is a process for manufacturing a mask on the basis of the circuit pattern design. Step 853 is a process for manufacturing a wafer by using a material such as silicon.

Step 854 is a wafer process, which is called a pre-process wherein, by using the so prepared mask and wafer, circuits are formed on the wafer through lithography. To form circuits on the wafer that correspond with sufficient spatial resolution those patterns on the mask, interferometric positioning of the lithography tool relative the wafer is necessary. The catadioptric imaging systems described herein can be especially useful to inspect the surface of the wafer and internal layers generate on the wafer by wafer processing to check and monitor the effectiveness of the lithography used in the wafer process. Step 855 is an assembling step, which is called a post-process wherein the wafer processed by step 854 is formed into semiconductor chips. This step includes assembling (dicing and bonding) and packaging (chip sealing). Step 856 is an inspection step wherein operability check, durability check and so on of the semiconductor devices produced by step 855 are carried out. With these processes, semiconductor devices are finished and they are shipped (step 857).

Figure 7C:
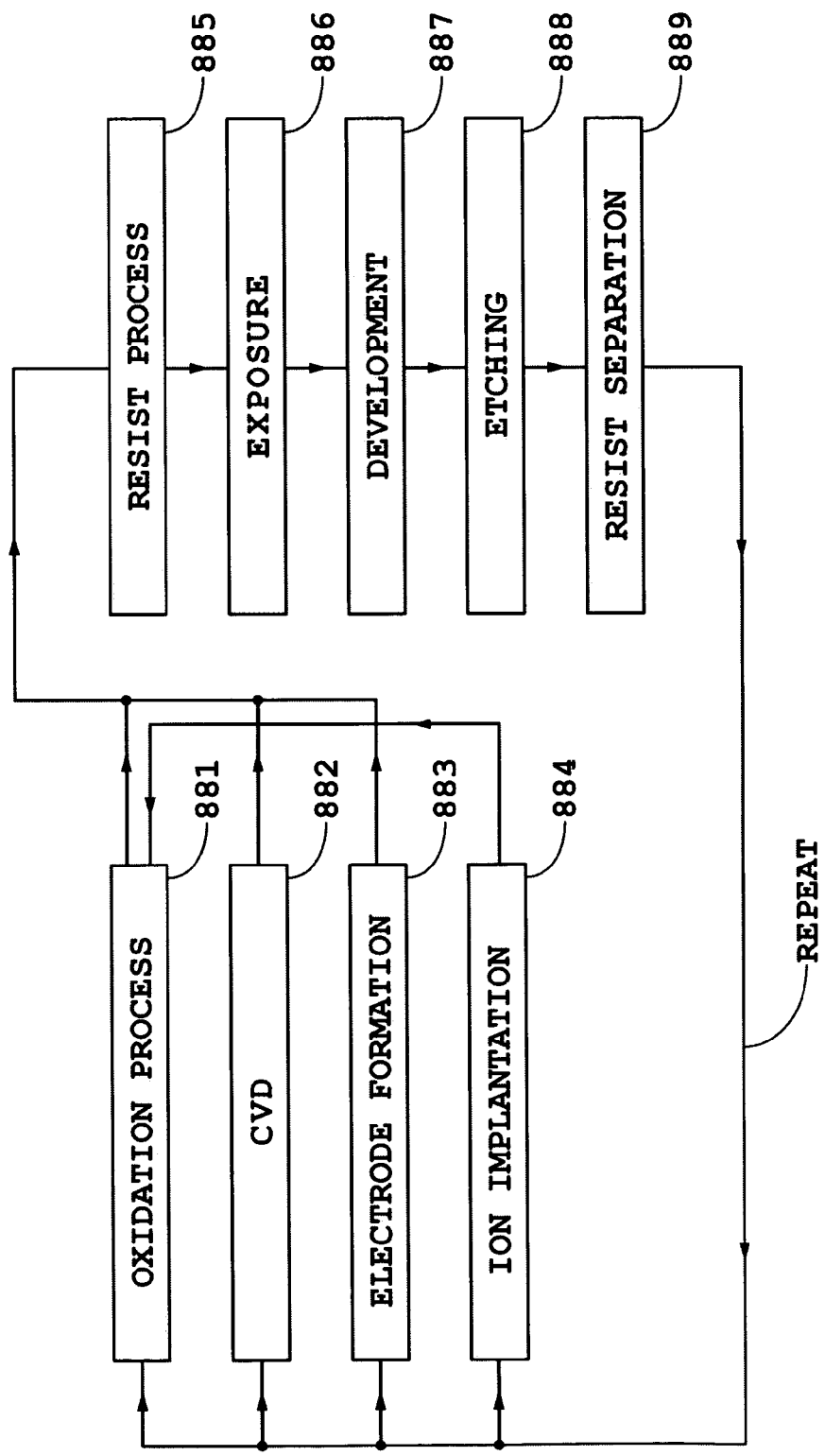
FIG. 7c is a flow chart showing steps of the wafer process.

FIG. 7c is a flow chart showing details of the wafer process. Step 881 is an oxidation process for oxidizing the surface of a wafer. Step 882 is a CVD process for forming an insulating film on the wafer surface. Step 883 is an electrode forming process for forming electrodes on the wafer by vapor deposition. Step 884 is an ion implanting process for implanting ions to the wafer. Step 885 is a resist process for applying a resist (photosensitive material) to the wafer. Step 886 is an exposure process for printing, by exposure (i.e., lithography), the circuit pattern of the mask on the wafer through the exposure apparatus described above. Once again, as described above, the use of the catadioptric imaging systems described herein improve the accuracy, resolution, and maintenance of such lithography steps.

Step 887 is a developing process for developing the exposed wafer. Step 888 is an etching process for removing portions other than the developed resist image. Step 889 is a resist separation process for separating the resist material remaining on the wafer after being subjected to the etching process. By repeating these processes, circuit patterns are formed and superimposed on the wafer.

Figure 8:
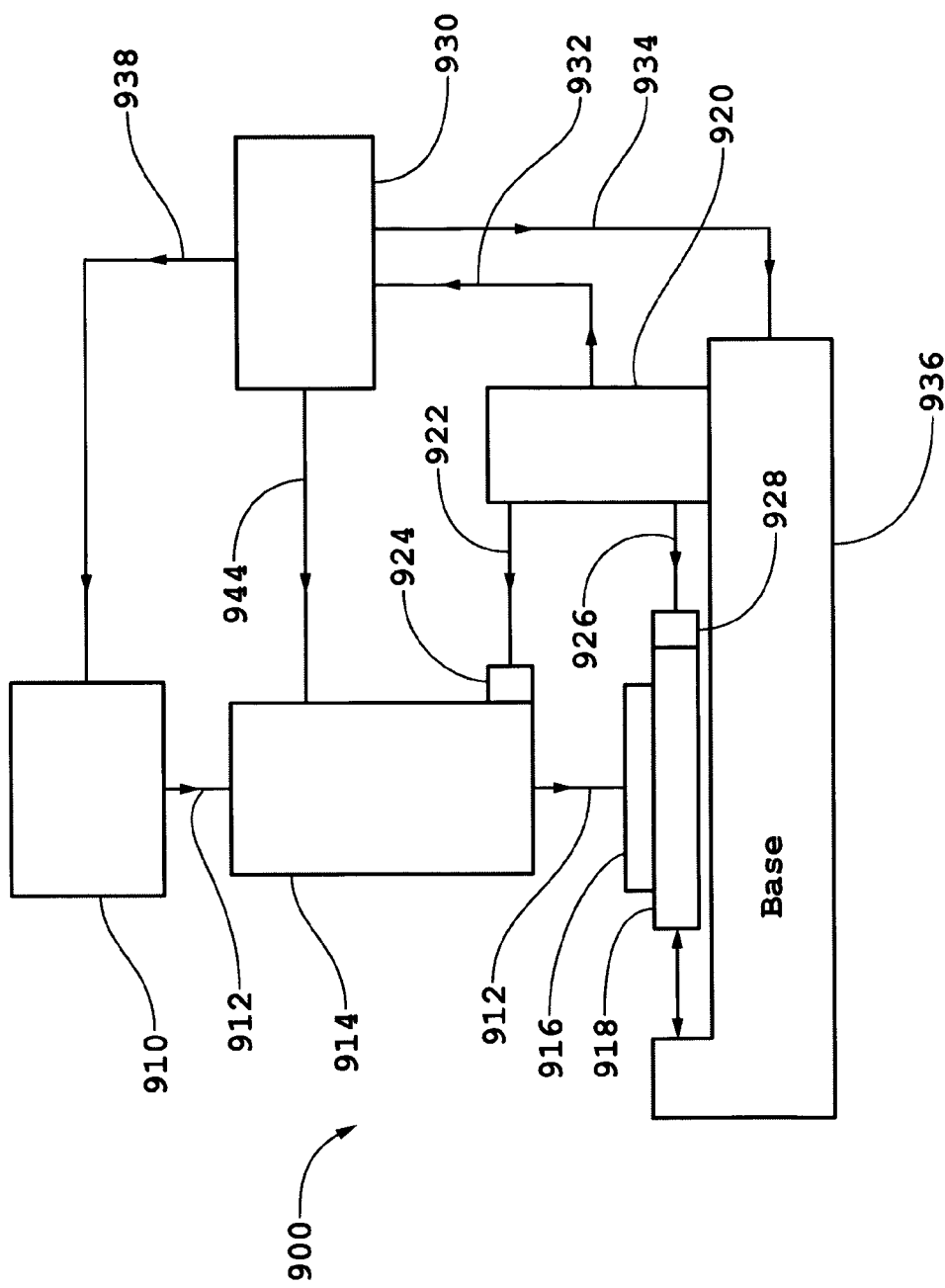
FIG. 8 is a schematic diagram of an inspection tool that uses catoptric and catadioptric imaging systems with pellicle or aperture array beam-splitters (not shown in figure).

An important application of the catadioptric imaging systems described herein is the inspection of masks and reticles used in the lithography methods described previously. As an example, a schematic of a mask inspection system 900 is shown in FIG. 8. A source 910 generates a source beam 912 and a catadioptric imaging system assembly 914 directs the radiation beam to a substrate 916 supported by a movable stage 918. To determine the relative position of the stage, an interferometry system 920 directs a reference beam 922 to a mirror 924 mounted on beam focusing assembly 914 and a measurement beam 926 to a mirror 928 mounted on stage 918. Changes in the position measured by the interferometry system correspond to changes in the relative position of write beam 912 on substrate 916. Interferometry system 920 sends a measurement signal 932 to controller 930 that is indicative of the relative position of inspection beam 912 on substrate 916. Controller 930 sends an output signal 934 to a base 936 that supports and positions stage 918.

Controller 930 can cause catadioptric imaging system assembly 914 to scan the inspection beam over a region of the substrate, e.g., using signal 944. As a result, controller 930 directs the other components of the system to inspect the substrate. The mask inspection compares the mask pattern directly with computer data used to generate the mask.

While the invention has been described with reference to particular embodiments thereof, those skilled in the art will be able to make the various modifications to the described embodiments without departing from the true spirit and scope of the present invention.

What is claimed is:

1. An interferometric system comprising:
an interferometer that directs a measurement beam at an object point to produce a return measurement beam, focuses the return measurement beam to an image point in an image plane, and mixes the return measurement beam with a reference beam at the image point to form a mixed beam;
a beam combining layer located at the image plane which is responsive to the mixed beam and produces an optical beam therefrom, wherein said layer comprises a thin film with an array of transmissive openings formed therein and further comprises a fluorescent material associated with each of the openings of the array of openings;
a detector that is responsive to the optical beam from the beam combining layer; and
an imaging system that directs the optical beam from the beam combining layer onto the detector.

2. The interferometric system of claim 1, wherein the beam combining layer comprises a first layer in which the array of openings is formed and a second layer behind the first layer and comprising the fluorescent material.

3. The interferometric system of claim 1, wherein the beam combining layer further comprises third layer comprising an array of microlenses, each of which is aligned with a different one of the openings in the array of openings.

4. The interferometric system of claim 1, wherein the fluorescent material is in each of the openings of the array of openings.

5. The interferometric system of claim 1, wherein each of the openings in the array of openings is conically shaped.

6. The interferometric system of claim 1, wherein the fluorescent material comprises lumogen.

7. The interferometric system of claim 1, wherein the fluorescent material is sensitive to UV or VUV.

8. The interferometric system of claim 1, wherein the fluorescent material is responsive to radiation at a first wavelength and the detector is responsive to light at a second wavelength, wherein the first and second wavelengths are different.

9. The interferometric system of claim 8, wherein the fluorescent material is responsive to radiation in the UV or VUV region and the detector is responsive to light in the visible region.

10. The interferometric system of claim 1, wherein the fluorescent material absorbs radiation at a first wavelength and emits radiation at a second wavelength, wherein the second wavelength is longer than the first wavelength.

11. The interferometric system of claim 1, wherein the imaging system is a low power microscope.

12. The interferometric system of claim 1, wherein the interferometer comprises a catadioptric imaging system.

13. The interferometric system of claim 1, wherein the interferometer comprises:
- a beam splitter positioned to receive the return measurement beam from the object point and separate each of a plurality of rays into a transmitted portion and a reflected portion, the transmitted portions defining a first set of rays and the reflected portions defining a second set of rays; and
- a reflecting surface positioned to receive one of the sets of rays from the beam splitter and focus that set of rays towards the image point via the beam splitter.

14. The interferometric system of claim 13, wherein the interferometer comprises an array of independently positionable reflecting elements forming the reflecting surface.

15. The interferometric system of claim 14, wherein the reflecting surface is positioned to receive the first set of rays and reflect the first set of rays back to the beam splitter, and wherein the beam splitter is positioned to reflect at least a portion of each ray received from the reflecting surface to the image point.

16. The interferometric system of claim 13, wherein the beam splitter has an array of transmitting apertures formed therein and wherein said one set of rays travels along a path contacting on one end the beam splitter and on another end the concave reflecting surface and at least most of which passes through a gas or vacuum.

17. An interferometric system comprising:
- an interferometer that directs a measurement beam at an object point to produce a return measurement beam, focuses the return measurement beam to an image point in an image plane, and mixes the return measurement beam with a reference beam at the image point to form a mixed beam; and
- a detector system that generates an electrical interference signal from the mixed beam, wherein the interferometer comprises a source for generating an input beam and an apodizing filter through which the input beams passes to generate a conditioned beam, and wherein the measurement beam is derived from the conditioned beam.

18. The interferometric system of claim 17, wherein the interferometer further comprises a focusing optic for focusing the measurement beam as a spot on the object.

19. The interferometric system of claim 17, wherein the apodizing filter comprises an aperture that is apodized.

20. The interferometric system of claim 17, wherein the apodizing filter comprises an aperture and a coating that has a transmission coefficient that depends on the position within the aperture.

* * * * *